United States Patent
Nishii et al.

(10) Patent No.: US 10,332,280 B2
(45) Date of Patent: Jun. 25, 2019

(54) INFORMATION PROCESSING APPARATUS, INFORMATION PROCESSING METHOD, AND CONTROL APPARATUS

(71) Applicant: CANON KABUSHIKI KAISHA, Tokyo (JP)

(72) Inventors: Yuichi Nishii, Kawasaki (JP); Nobu Miyazawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/099,936

(22) Filed: Apr. 15, 2016

(65) Prior Publication Data

US 2016/0232691 A1    Aug. 11, 2016

Related U.S. Application Data

(63) Continuation of application No. PCT/JP2014/005382, filed on Oct. 23, 2014.

(30) Foreign Application Priority Data

Oct. 24, 2013  (JP) .................................. 2013-221539
Apr. 28, 2014  (JP) .................................. 2014-092538

(51) Int. Cl.
*A61B 6/00*  (2006.01)
*G06T 11/00*  (2006.01)
(Continued)

(52) U.S. Cl.
CPC ............ *G06T 11/006* (2013.01); *A61B 6/025* (2013.01); *A61B 6/461* (2013.01); *A61B 6/547* (2013.01);
(Continued)

(58) Field of Classification Search
CPC combination set(s) only.
See application file for complete search history.

(56) References Cited

U.S. PATENT DOCUMENTS 6,075,256 A    6/2000  Kaifu et al.
6,512,279 B2   1/2003  Kaifu et al.
(Continued)

FOREIGN PATENT DOCUMENTS

CN    102793553 A    11/2012
CN    102846306 A    1/2013
(Continued)

OTHER PUBLICATIONS

International Search Report and Written Opinion issued in International Application No. PCT/JP2014/005382 dated Feb. 3, 2015.
(Continued)

*Primary Examiner* — Tsung Yin Tsai
(74) *Attorney, Agent, or Firm* — Venable LLP

(57) ABSTRACT

This invention provides a technique of appropriately managing a high-resolution tomographic image and effectively displaying an arbitrary cross section even under an environment where a 3D texture has a size limitation. An information processing apparatus includes a determination unit adapted to determine whether a size of a plurality of tomographic images acquired from a single object is not more than a predetermined size, a management unit adapted to, upon determining that the size is not more than the predetermined size, manage the plurality of tomographic images as three-dimensional voxel data, a decision unit adapted to decide a cross-sectional image as a display target of an object image managed as the three-dimensional voxel data, and a display control unit adapted to cause a display unit to display the decided cross-sectional image.

20 Claims, 35 Drawing Sheets

(51) Int. Cl.
*A61B 6/02* (2006.01)
*G06T 19/00* (2011.01)
*G06T 7/00* (2017.01)

(52) U.S. Cl.
CPC ............ *G06T 7/0012* (2013.01); *G06T 19/00* (2013.01); *A61B 6/463* (2013.01); *A61B 6/5223* (2013.01); *G06T 2200/04* (2013.01); *G06T 2207/10081* (2013.01); *G06T 2207/20004* (2013.01); *G06T 2211/421* (2013.01); *G06T 2219/008* (2013.01); *G06T 2219/028* (2013.01)

(56) References Cited

U.S. PATENT DOCUMENTS

| | | |
|---|---|---|
| 6,982,422 B2 | 1/2006 | Kaifu et al. |
| 7,022,997 B2 | 4/2006 | Kaifu et al. |
| 7,085,406 B2 | 8/2006 | Alyassin |
| RE39,780 E | 8/2007 | Kaifu et al. |
| 7,760,924 B2 | 7/2010 | Ruth et al. |
| RE42,157 E | 2/2011 | Kaifu et al. |
| 7,970,203 B2 | 6/2011 | Avinash et al. |
| 8,801,182 B2 | 8/2014 | Kurosaka |
| 8,942,450 B2 | 1/2015 | Riddell |
| 9,123,108 B2 | 9/2015 | Tajima |
| 2002/0167061 A1 | 11/2002 | Kaifu et al. |
| 2008/0019580 A1* | 1/2008 | Ohyu .................. G06K 9/3216 382/130 |
| 2011/0145693 A1* | 6/2011 | Mutic .................. G06F 19/321 715/233 |
| 2012/0053454 A1* | 3/2012 | Wang .................... A61B 6/463 600/425 |
| 2012/0249549 A1* | 10/2012 | Endo ................... A61B 8/4416 345/419 |
| 2012/0300899 A1* | 11/2012 | Tajima .................. G06T 7/337 378/19 |
| 2013/0003015 A1 | 1/2013 | Kurosaka |
| 2015/0138564 A1* | 5/2015 | Jung ..................... G01N 21/95 356/479 |
| 2016/0345925 A1* | 12/2016 | Westerhoff .......... A61B 6/5223 |

FOREIGN PATENT DOCUMENTS

| | | |
|---|---|---|
| JP | S62-229379 A | 10/1987 |
| JP | H06-215153 A | 8/1994 |
| JP | H08-116044 A | 5/1996 |
| JP | 2003-116825 A | 4/2003 |
| JP | 2003-210444 A | 7/2003 |
| JP | 2008-068032 A | 3/2008 |
| JP | 2008-229333 A | 10/2008 |
| JP | 2011-125698 A | 6/2011 |
| JP | 2012-512669 A | 6/2012 |
| NO | 2010/059920 A2 | 5/2010 |

OTHER PUBLICATIONS

Sep. 30, 2018 Chinese Official Action in Chinese Patent Appln No. 201480058111.6.

* cited by examiner

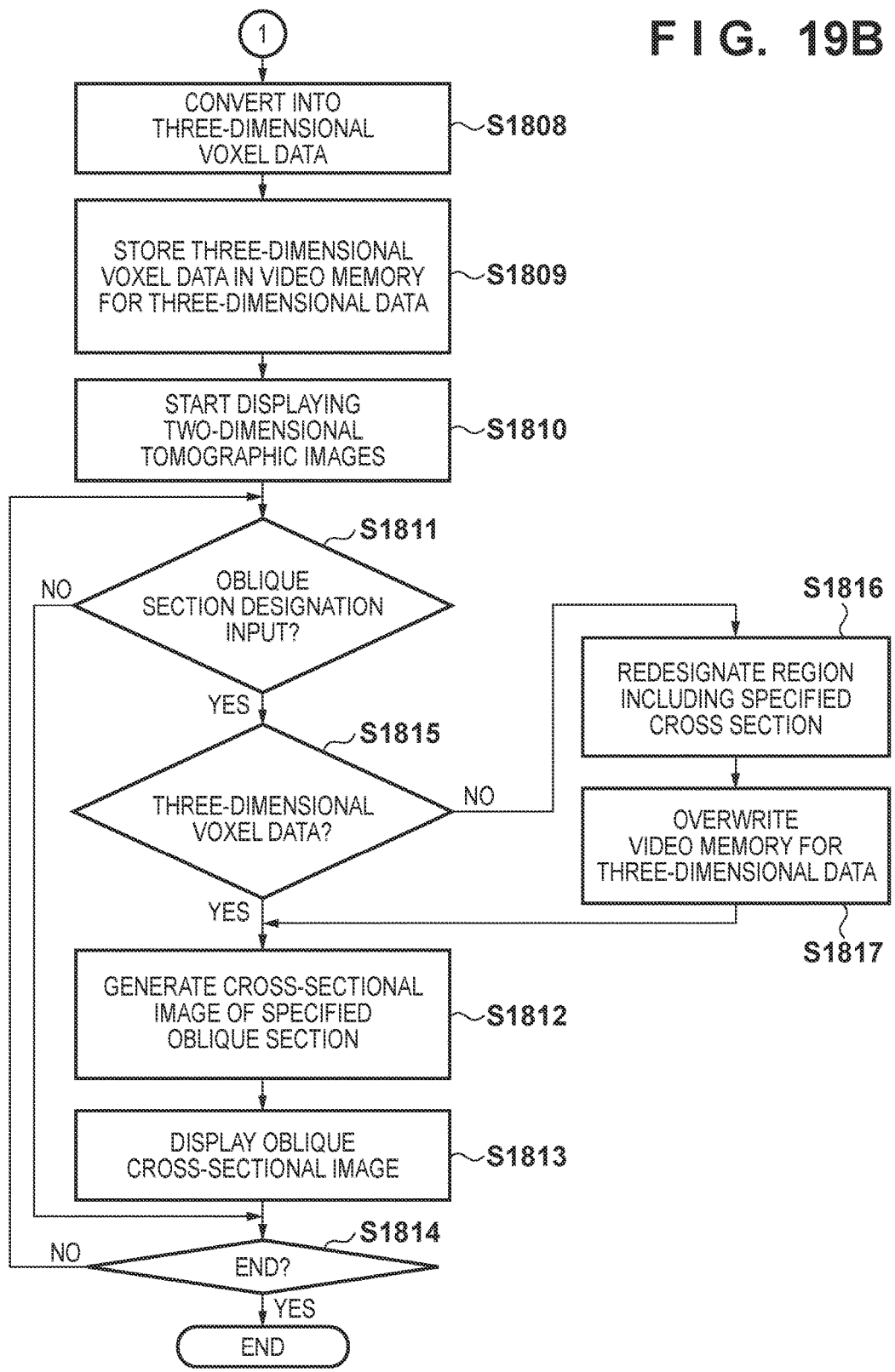

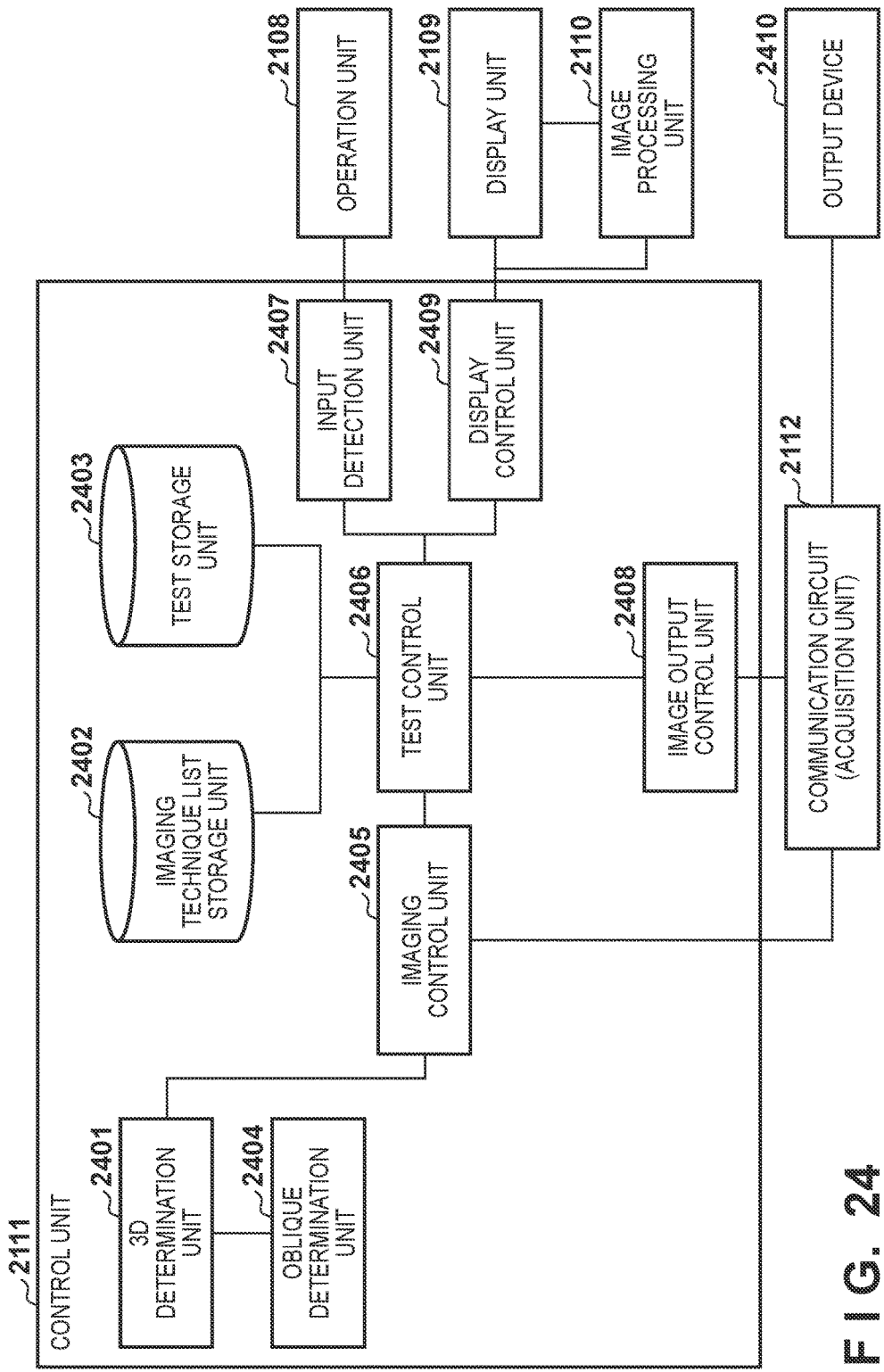
F I G. 24

FIG. 36

IMAGING TECHNIQUE SETTING — 3601

- PROTOCOL NAME: Hand Tomosynthesis — 3602
- SERIES DESCRIPTION: — 3603
- COMMENT: — 3604
- LATERALITY MARKER: — 3605
  - L
    - ARRANGEMENT POSITION: MIDDLE - CENTER ⋁
    - ☐ EMBED AT THE TIME OF IMAGING
  - R
    - ARRANGEMENT POSITION: MIDDLE - CENTER ⋁
    - ☐ EMBED AT THE TIME OF IMAGING

- DICOM ATTRIBUTE: — 3606
- TEST PART: ABDOMEN ⋁
- PATIENT DIRECTION: R/F ⋁
- FIELD POSITION: AP ⋁
- LATERALITY: U ⋁
- OBLIQUE SECTION DISPLAY LIMITATION: — 3607
  - ☑ APPLY DISPLAY LIMITATION
- DISPLAY LIMITING METHOD: CUT OUT PROJECTED IMAGES ⋁

[ CANCEL ] — 3608  [ DETERMINE ] — 3609

INFORMATION PROCESSING APPARATUS, INFORMATION PROCESSING METHOD, AND CONTROL APPARATUS

This application is a continuation of International Patent Application No. PCT/JP2014/005382 filed on Oct. 23, 2014, and claims priority to Japanese Patent Applications No. 2013-221539 filed on Oct. 24, 2013, and 2014-092538 filed on Apr. 28, 2014, the entire contents of which are incorporated herein by reference.

TECHNICAL FIELD

The present invention relates to an information processing apparatus, an information processing method, and a control apparatus. The present invention particularly relates to effective image management/display in a case in which a GPU (Graphics Processing Unit) is used for reconstruction and display of tomosynthesis image capturing.

BACKGROUND ART

There is a tomosynthesis image capturing method as an X-ray imaging method for obtaining volume data that is data representing a concentration or density distribution in a space. The tomosynthesis image capturing method is an imaging method that performs X-ray imaging a plurality of times using a digital detector while moving an X-ray tube relative to a subject. A plurality of collected images obtained by the tomosynthesis image capturing are reconstructed into a plurality of tomographic image data and displayed.

The tomosynthesis image capturing method has received attention because it can acquire volume data without needing a large-scale apparatus unlike CT (Computed Tomography), supported by proliferation of digital detectors. PTL 1 discloses using a GPU (Graphics Processing Unit) for reconstruction and display of tomosynthesis image capturing.

CITATION LIST

Patent Literature

PTL 1: Japanese Patent Laid-Open No. 2011-125698

SUMMARY OF INVENTION

Technical Problem

The above-described 3D texture is limited to a considerably small size, as compared to a 2D texture that is a two-dimensional region. For example, in Direct 3D 11 that is one of interfaces to a GPU in Windows®, the size of a 3D texture is limited to 2048×2048×2048 pixels. On the other hand, the size of a 2D texture is limited to 16384×16384×N (N depends on the capacity of a video memory mounted on a graphic board). As described above, concerning both the width and height of an image, there is a pixel size difference of eight times between the 3D texture and the 2D texture.

Such size limitation is probably sufficient in a game that often uses a GPU. Actually, a 2D texture is used in many cases. Even if a 3D texture is used, voxel data is normally handled as data of about 512×512×512 pixels or 1024×1024×1024 pixels at maximum.

However, the tomosynthesis image capturing method is often used in a field needing high-resolution images such as mammography, and voxel data beyond the size limitation may be used. In this case, the conventional arrangement cannot appropriately manage a high-resolution tomographic image obtained by tomosynthesis image capturing and display an arbitrary cross section.

The present invention has been made in consideration of the above-described problem, and has as its object to provide a technique of appropriately managing a high-resolution tomographic image and effectively displaying an arbitrary cross section even under an environment where a 3D texture has a size limitation.

Solution to Problem

An information processing apparatus according to the present invention has the following arrangement. That is, the information processing apparatus includes: a determination unit adapted to determine whether a size of a plurality of tomographic images acquired from a single object is not more than a predetermined size; a management unit adapted to, upon determining that the size is not more than the predetermined size, manage the plurality of tomographic images as three-dimensional voxel data; a decision unit adapted to decide a cross-sectional image as a display target of an object image managed as the three-dimensional voxel data; and a display control unit adapted to cause a display unit to display the decided cross-sectional image.

Advantageous Effects of Invention

According to the present invention, it is possible to provide a technique of appropriately managing a high-resolution tomographic image obtained by tomosynthesis image capturing and effectively displaying an arbitrary cross section even under an environment where a 3D texture has a size limitation.

Other features and advantages of the present invention will be apparent from the following descriptions taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIGS. 19A and 19B are flowcharts showing the procedure of processing by the system control unit;

FIG. 24 is a view showing the arrangement of an imaging control unit according to the embodiment of the present invention;

FIG. 36 is a view showing an imaging technique information setting screen according to the embodiment of the present invention.

DESCRIPTION OF EMBODIMENTS

Preferred embodiments of the present invention will now be described in detail with reference to the accompanying drawings.

Figure 1:
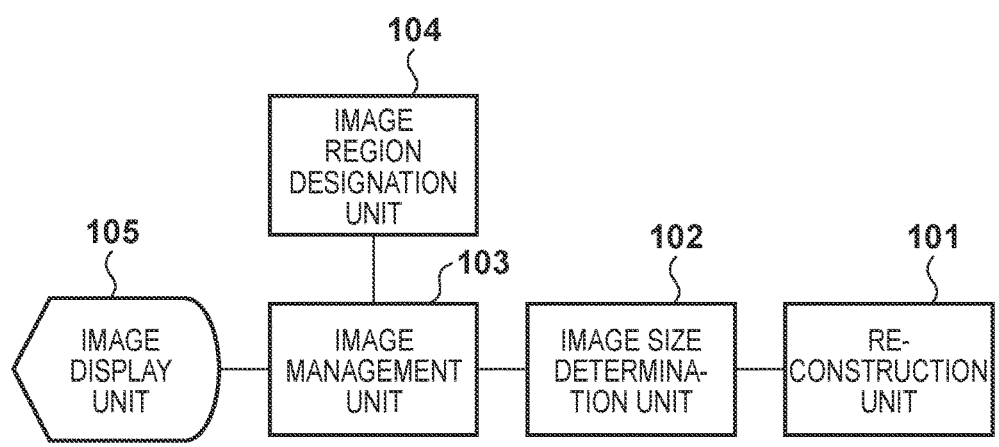
FIG. 1 is a block diagram showing a schematic arrangement of an X-ray image display apparatus.

First Embodiment (Arrangement of X-Ray Image Display Apparatus) FIG. 1 is a block diagram showing the arrangement of an X-ray image display apparatus as an information processing apparatus according to this embodiment. As shown in FIG. 1, the X-ray image display apparatus includes a reconstruction unit 101, an image size determination unit 102, an image management unit 103, an image region designation unit 104, and an image display unit 105.

The reconstruction unit 101 is a constituent element that reconstructs a plurality of tomographic images from a plurality of images collected by tomosynthesis image capturing. The image size determination unit 102 is a constituent element that determines the size of the plurality of tomographic images. The image management unit 103 is a constituent element that decides, based on the result of determination by the image size determination unit, whether to manage each image as two-dimensional data or three-dimensional data. The image region designation unit 104 is a constituent element that designates which region of an image managed by the image management unit should be displayed. The image display unit 105 is a constituent element that performs display control processing of processing the region designated by the image region designation unit and causing an external display device (display unit) such as a liquid crystal panel or an internal monitor to display it.

The X-ray image display apparatus according to this embodiment is implemented by a general-purpose information processing apparatus such as a personal computer (PC) including a CPU (Central Processing Unit). However, each constituent element of the X-ray image display apparatus may be constituted by dedicated hardware, or some constituent elements may be implemented by embedded devices.

Figure 2:
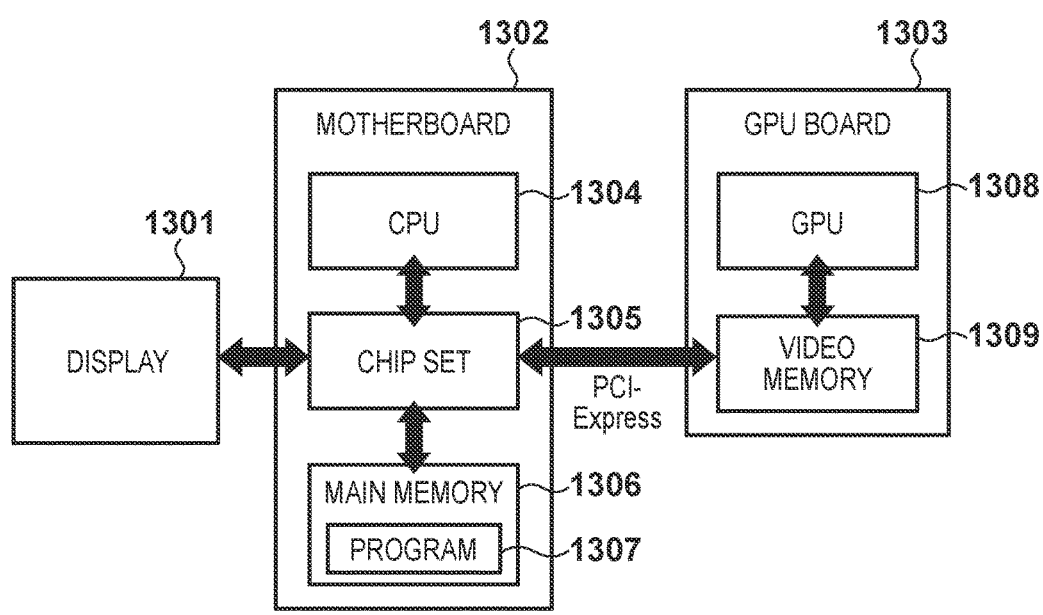
FIG. 2 is a view showing an example of the hardware arrangement of the X-ray image display apparatus.
Figure 3:
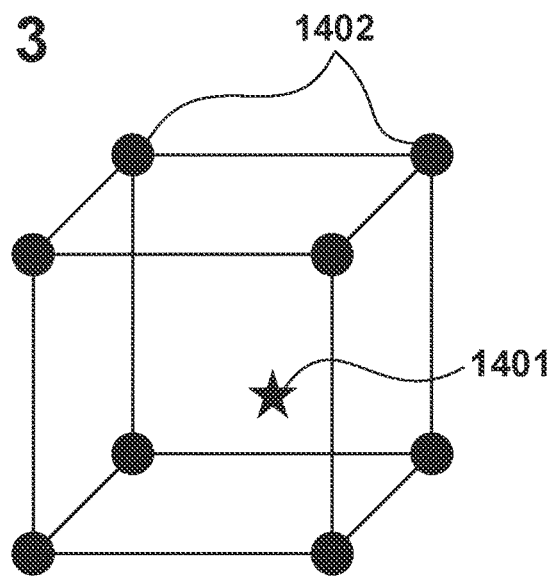
FIG. 3 is a view showing a state in which the pixel value of an arbitrary coordinate point by interpolating the pixel values of peripheral points.
Figure 4:
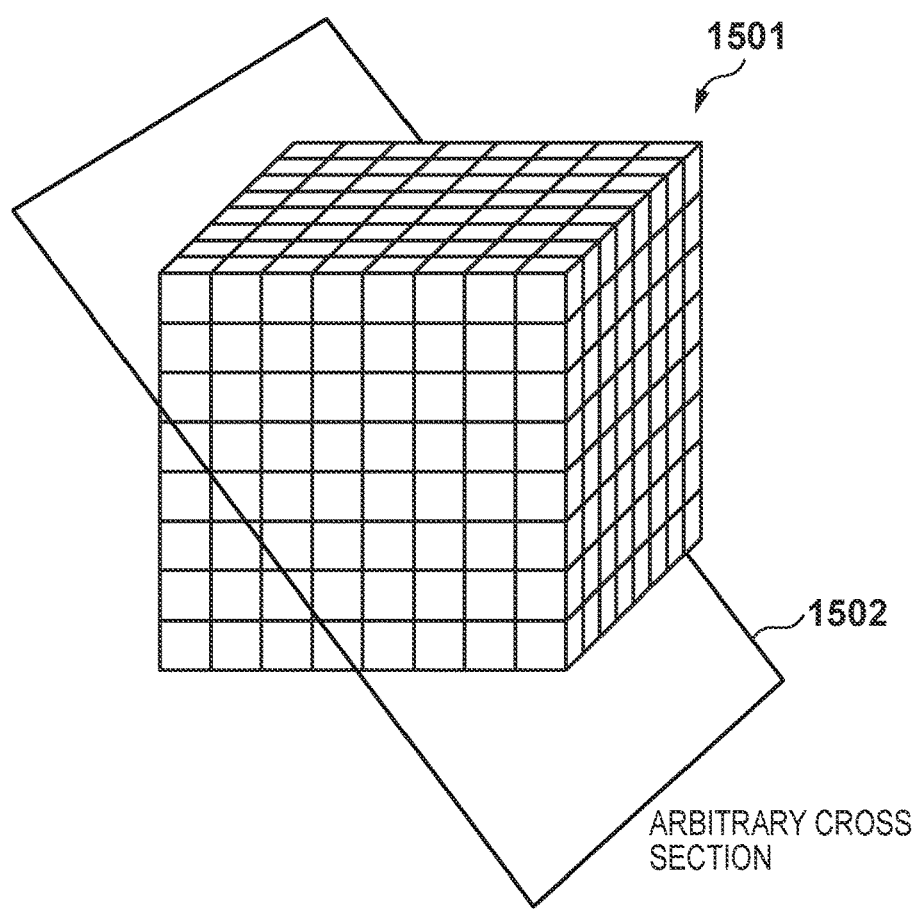
FIG. 4 is a view showing an arbitrary cross section designated on an image managed as three-dimensional voxel data.

FIG. 2 is a view showing an example of the hardware arrangement of the X-ray image display apparatus. As shown in FIG. 2, the X-ray image display apparatus includes a display 1301, a motherboard 1302, and a GPU board 1303. A GPU 1308 is an arithmetic unit provided in a general-purpose graphic board, and is formed in the GPU board 1303 together with a video memory 1309, as shown in FIG. 2. When such an arithmetic unit is used, high-speed operation and display can be done without using dedicated hardware. In particular, the GPU 1308 can manage a three-dimensional image on the video memory 1309 as three-dimensional voxel data called a 3D texture. When an image is managed as three-dimensional voxel data, as shown in FIG. 3, the GPU 1308 can automatically acquire the pixel value of a point of arbitrary coordinates (star symbol 1401) by interpolating the values of eight peripheral pixels (circles 1402). Hence, as shown in FIG. 4, the GPU 1308 has a function of greatly facilitating displaying the contents of image data 1501 on an arbitrary cross section 1502 only by designating the position and direction of the arbitrary cross section 1502 on the image data 1501 managed as three-dimensional voxel data.

As shown in FIG. 2, the motherboard 1302 includes a CPU 1304, a chip set 1305, and a main memory 1306. The main memory 1306 stores a program 1307. The program controls the GPU 1304. As shown in FIG. 2, the display 1301, the motherboard 1302, and the GPU board 1303 are connected via the chip set 1305 provided in the motherboard 1302.

The above-described image display unit 105 can be implemented by the display 1301 and a display control module included in the program 1307. The image management unit 103 and the reconstruction unit 101 can be implemented by the program 1307, the CPU 1304 that operates based on the program, the chip set 1305, and the GPU 1308. The image size determination unit 102 and the image region designation unit 104 can be implemented by the program 1307, the CPU 1304, and the chip set 1305.

(Processing Procedure)

If the size of a plurality of tomographic images acquired from the same object is equal to or smaller than a predetermined size, the X-ray image display apparatus according to this embodiment manages the tomographic images as three-dimensional voxel data. If the size exceeds the predetermined size, the tomographic images are managed as two-dimensional data. The detailed procedure of processing executed by the X-ray image display apparatus according to this embodiment will be described with reference to the flowchart of FIG. 5. Each step to be described below is executed when the CPU of the X-ray image display apparatus performs control based on a computer program.

When a plurality of tomographic images are prepared from a plurality of images collected by tomosynthesis image capturing, the reconstruction unit 101 executes reconstruction processing to generate a plurality of tomographic images (step S201). As the reconstruction processing, the shift-and-add method or filter back projection method is generally used. Normally, as a tomographic image of tomosynthesis, an image in the coronal (coronal section) direction (to be described later) is acquired.

Next, the image size determination unit 102 determines whether both the height and width of the plurality of tomographic images generated in the above process are equal to or smaller than a predetermined size (step S202). Note that in this embodiment, the predetermined size is the maximum value of the height and width of three-dimensional data that the GPU can cope with, and is set in advance in the X-ray image display apparatus before execution of processing. However, the predetermined size may be the size of a smaller height or width. Upon determining in step S202 that the size of the tomographic images exceeds the predetermined size, that is, the height or width of the tomographic images exceeds the height or width of the predetermined size (NO in step S202), the image management unit 103 advances to step S203. On the other hand, upon determining that the size of the tomographic images is equal to or smaller than the predetermined size, that is, both the height and width of the tomographic images are equal to or smaller than the height and width of the predetermined size (YES in step S202), the image management unit 103 advances to step S206.

Figure 6:
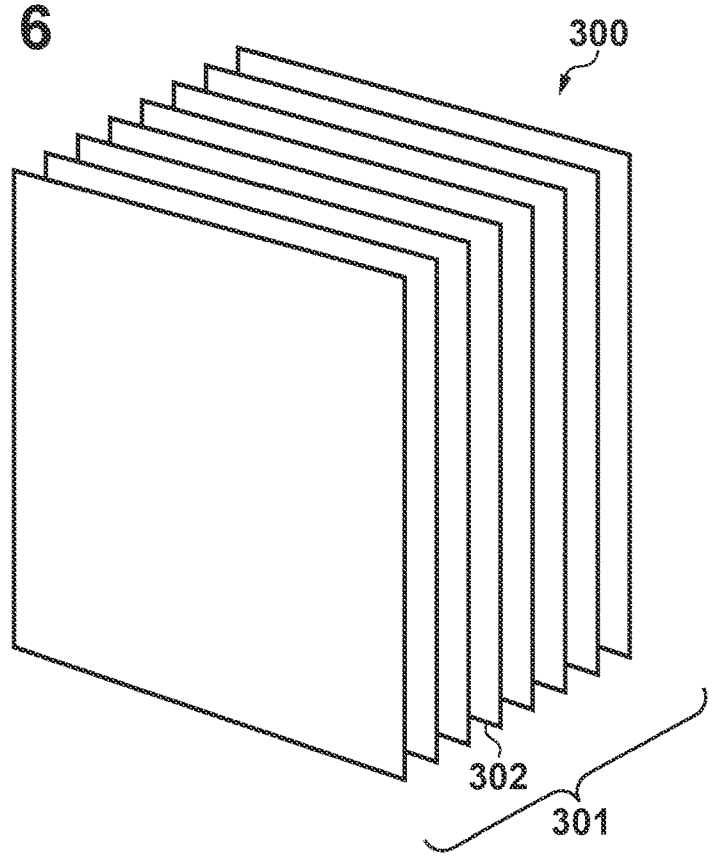
FIG. 6 is a view showing a state in which tomographic images are managed as a plurality of two-dimensional data.

In step S203, the image management unit 103 manages the tomographic images as a plurality of two-dimensional data. FIG. 6 schematically shows a state in which tomographic images are managed as a plurality of two-dimensional data. In FIG. 6, tomographic images 300 including three-dimensional information are managed as an aggregate 301 of a plurality of two-dimensional data (for example, 302). Each two-dimensional data corresponds to the image of a cross section of the tomographic images 300.

Next, in step S204, the image region designation unit 104 designates index information used to identify display target two-dimensional data (for example, 302) from the aggregate 301 of the two-dimensional data representing the tomographic images. Designation of the index information can be done by, for example, causing the user to select a cross section to be displayed.

Next, in step S208, the image display unit 105 performs acquisition/generation or image processing for the image represented by the two-dimensional data identified by the index information, and then displays it on an external display device or the like.

Figure 7:
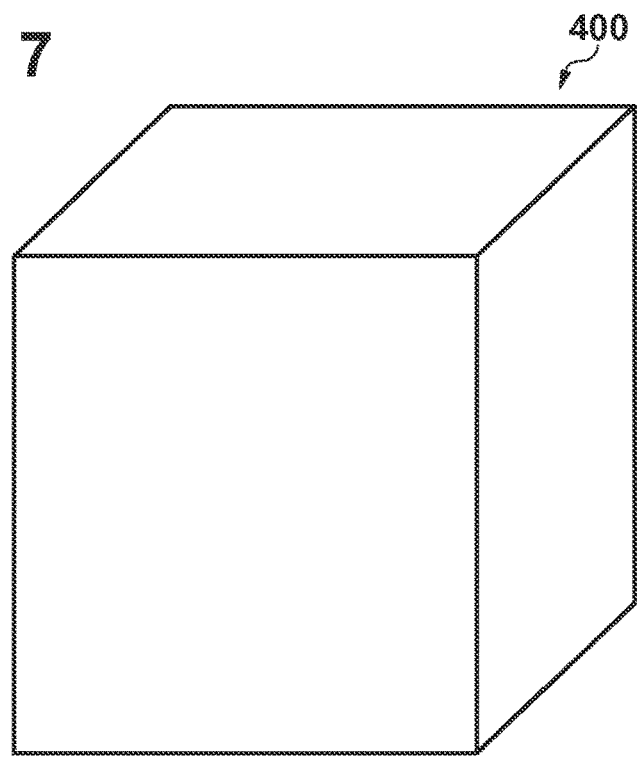
FIG. 7 is a view showing a state in which tomographic images are managed as a plurality of three-dimensional voxel data.

On the other hand, in step S206, the image management unit 103 converts the tomographic images into three-dimensional voxel data. The tomographic image group is thus managed as three-dimensional voxel data. FIG. 7 schematically shows a state in which tomographic images are managed as three-dimensional voxel data. In FIG. 7, tomographic images 400 are represented not as an aggregate of two-dimensional data but as one three-dimensional data.

In step S207, for the tomographic images managed as three-dimensional voxel data, the image region designation unit 104 determines coordinates in three directions along the X-, Y-, and Z-axes and rotation angles with respect to the axes as the center, thereby designating an arbitrary cross section as a display target. This designation can also be done by causing the user to select the coordinates and rotation angles.

In step S208, the image display unit 105 performs acquisition/generation or image processing for the image concerning the display target cross section, and then displays it on an external display device or the like.

Figure 8:
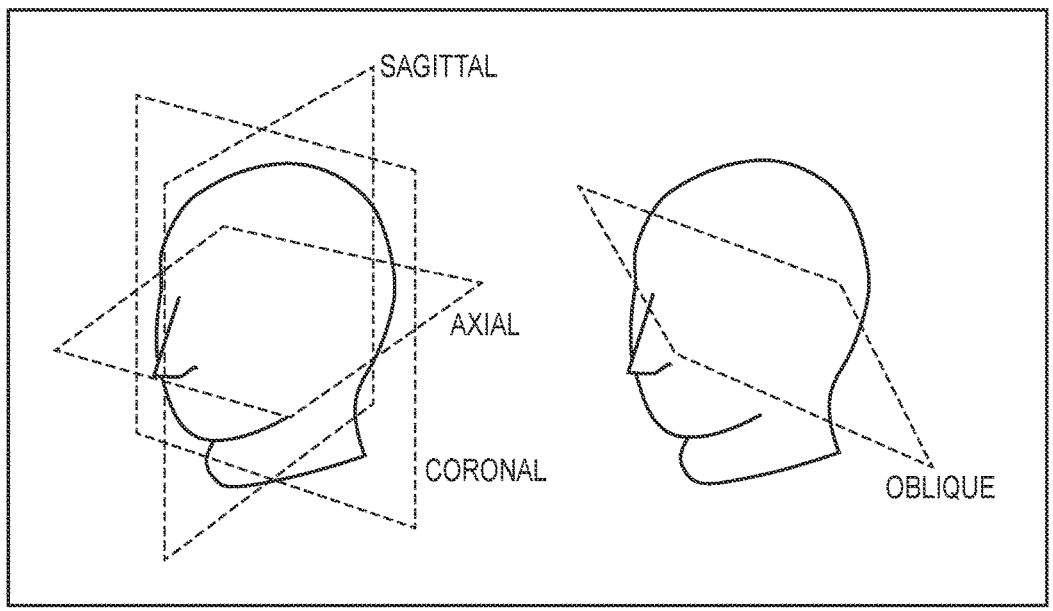
FIG. 8 is a view schematically showing an arbitrary cross section of a tomographic image.

Note that as the advantage of managing tomographic images as the above-described three-dimensional voxel data, when the tomographic images in the above-described coronal direction are mapped as three-dimensional data, the cross section of a tomographic image along an arbitrary direction in a three-dimensional space can be acquired. For example, arbitrary cross sections as shown in FIG. 8 can be acquired irrespective of whether the direction is the axial (transverse section) direction, coronal (coronal section) direction, or sagittal (sagittal section) direction. An arbitrary cross section can quickly be generated using an interpolation function provided as a standard by the GPU even for an image between a tomographic image A and a tomographic image B where no tomographic image exists originally. A tilted cross section called oblique (oblique section) as shown in FIG. 8 can also be generated using the interpolation function. Note that FIG. 8 shows an example in which the cross section is flat. However, when tomographic images are managed as three-dimensional voxel data, a curved cross section of the tomographic images can also be generated. On the other hand, when tomographic images are managed as a plurality of two-dimensional data, tomographic images including a plurality of coronal images are managed, as shown in FIG.

6. For this reason, the image of a cross section of unreconstructed coordinates or a cross section in a direction other than the coronal direction cannot be generated.

As described above, in this embodiment, it is determined whether the size of a plurality of tomographic images acquired from the same object is equal to or smaller than a predetermined size. Upon determining that the size is equal to or smaller than the predetermined size, the plurality of tomographic images are managed as three-dimensional voxel data. Then, a cross-sectional image as the display target of the object image managed as the three-dimensional voxel data is decided, and an external display device is caused to display the cross-sectional image. In this embodiment, the tomographic images are thus managed/displayed as three-dimensional voxel data only when their size falls within the size of a 3D texture. It is therefore possible to display a cross section of the tomographic images in an arbitrary direction as long as the GPU permits.

If the size of the plurality of tomographic images exceeds the predetermined size, the plurality of tomographic images are managed as a plurality of two-dimensional data. A tomographic image represented by one of the two-dimensional data is decided as a cross-sectional image. In this embodiment, if the size of the tomographic images falls outside the size of a 3D texture, the tomographic images are managed/displayed as a plurality of two-dimensional data. This enables browsing of minimum contents of the tomographic images even if they cannot be managed as three-dimensional data.

Additionally, in this embodiment, when the plurality of tomographic images are managed as three-dimensional voxel data, a cross-sectional image in an arbitrary direction is decided irrespective of the plane direction of the plurality of tomographic images. For this reason, according to this embodiment, it is possible to display an appropriate cross-sectional image by taking advantage of the characteristic of three-dimensional voxel data.

(Operation Example)

A detailed example of the operation of the X-ray image display apparatus will be described assuming that the predetermined size used by the image size determination unit 102 is 2048×2048 pixels.

Tomographic images are reconstructed in step S201. First, assume that the reconstructed tomographic images are two-dimensional data made of 10 32-bit slice images with respect to the object center, which have a thickness of 1 mm and a size of 3000×3000 pixels in the coronal direction (FIG. 6). In this case, since the size of the tomographic images exceeds the predetermined size in step S202 (NO in step S202), they are managed as 10 two-dimensional data (step S203). The bits are only normalized, and the two-dimensional data structure does not change. Hence, pieces of information that the image region designation unit 104 can designate are pieces of index information 1 to 10 which identify the two-dimensional images in the coronal direction.

Next, assume that the tomographic images reconstructed in step S201 are two-dimensional data made of 10 32-bit slice images with respect to the object center, which have a thickness of 1 mm and a size of 2000×2000 pixels in the coronal direction (FIG. 6). In this case, since the size of the tomographic images falls below the predetermined size in step S202 (YES in step S202), they are managed as three-dimensional voxel data having a sizes of 2000×2000×10 pixels (step S206). Since the tomographic images are managed as three-dimensional voxel data, the image region designation unit 104 can designate a region in an arbitrary direction as a display target region. For example, a coronal image located 0.5 mm from the center or an oblique image obtained by tilting, by 10°, a coronal image located 1.5 mm from the center can be generated and displayed.

Figure 9:
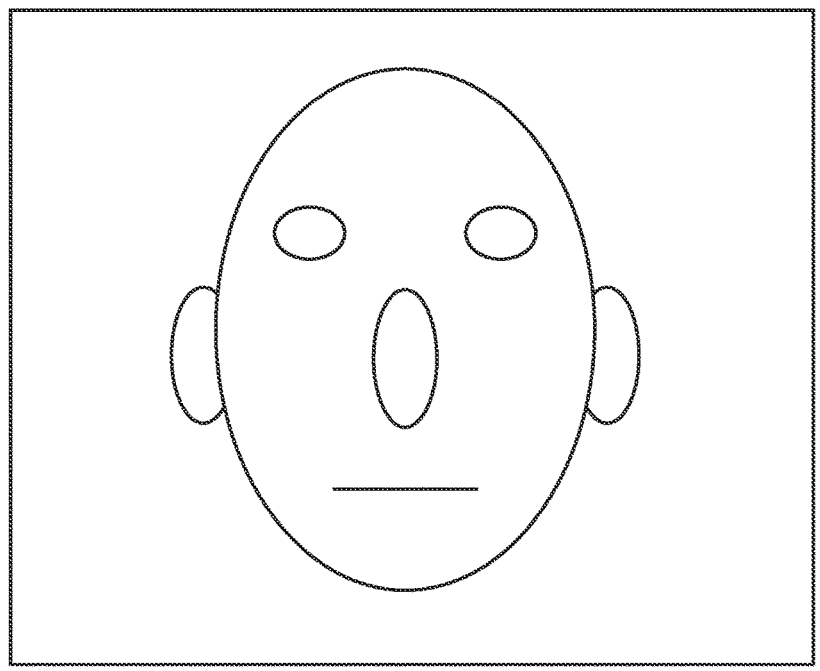
FIG. 9 is a view showing an example in which a single image in the coronal direction is displayed.
Figure 10:
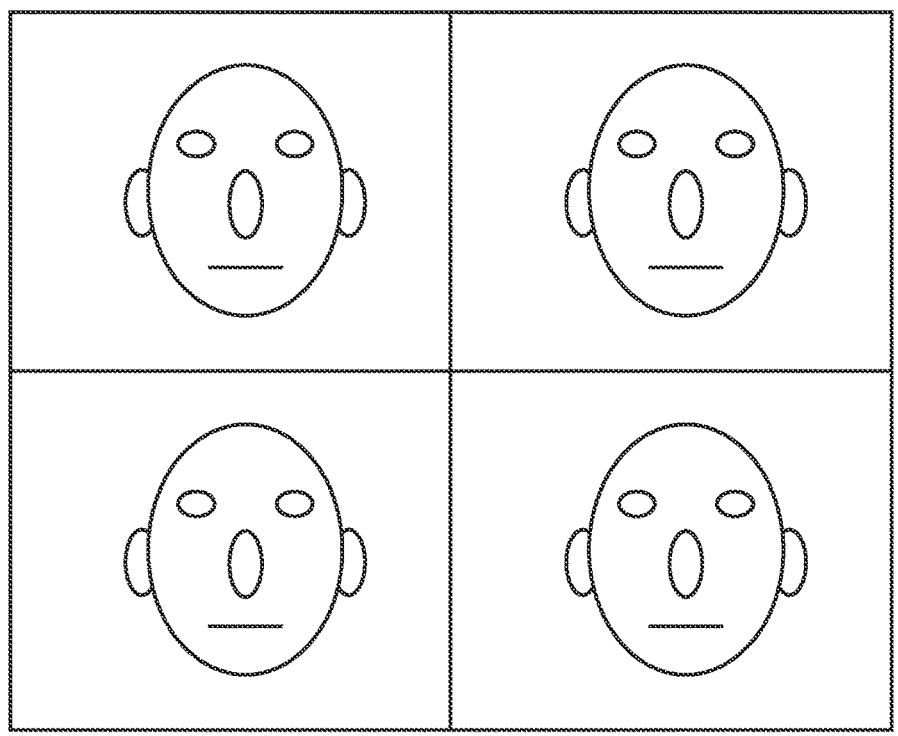
FIG. 10 is a view showing an example in which a plurality of images in the coronal direction are displayed.

The image display unit 105 can simultaneously display a plurality of cross sections. When the tomographic images are managed as plurality of two-dimensional data, it is possible to display only one image in the coronal direction, as shown in FIG. 9, or a plurality of identical coronal images, as shown in FIG. 10. It is also possible to display a plurality of index images of coronal images, for example, the first image at the upper left, the second image at the upper right, the third image at the lower left, and the fourth image at the lower right.

Figure 11:
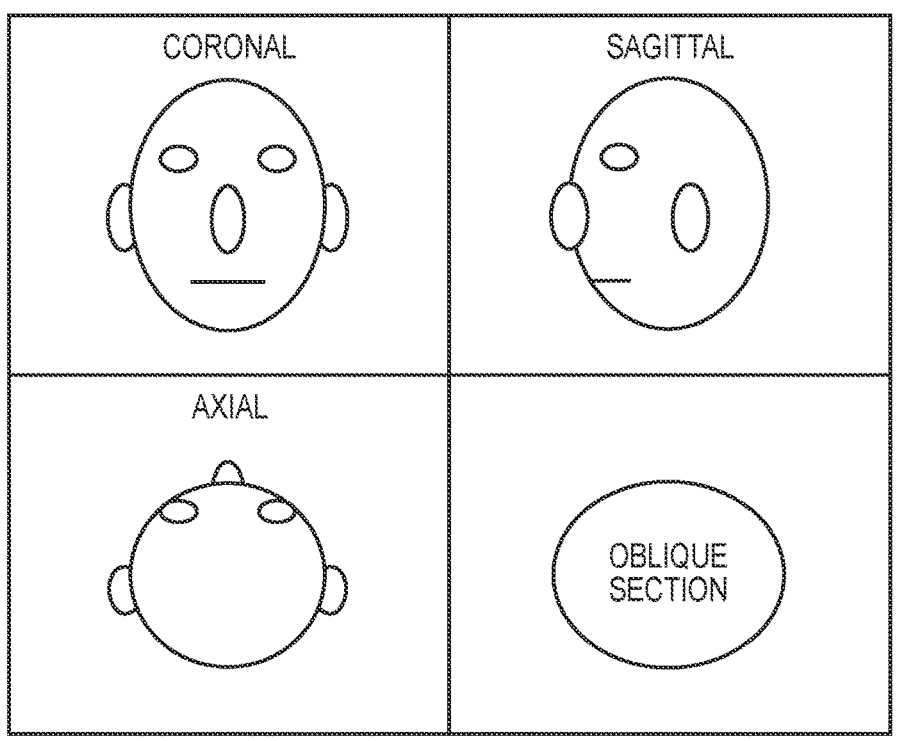
FIG. 11 is a view showing an example in which a plurality of images in different directions are displayed.

When data are managed as three-dimensional voxel data, display can be done in the same way as in the case in which the tomographic images are managed as a plurality of two-dimensional data. In addition, it is also possible to simultaneously display multiple cross sections in the axial, coronal, sagittal, and oblique directions, as shown in FIG. 11. Simultaneously displaying many reconstructed cross sections is generally called MPR (Multi-Planar Reconstruction). This display enables automatic switching depending on the size of tomographic images so as to display a single coronal image if the image size is equal to or smaller than a predetermined size or perform MPR display if the image size is equal to or larger than the predetermined size. When an external display device or the like is caused to display a plurality of cross-sectional images of tomographic images in this way, the tomographic images can easily be analyzed.

Second Embodiment

In the first embodiment, the arrangement that manages tomographic images as a plurality of two-dimensional data if their size is equal to or smaller than a predetermined size in step S202 has been described. In this embodiment, an arrangement that manages tomographic images as three-dimensional voxel data even if their size is equal to or smaller than a predetermined size will be described. Note that many of the operations and arrangements of this embodiment are common to the first embodiment, and arrangements unique to this embodiment will mainly be described.

(Processing Procedure)

Figure 12:
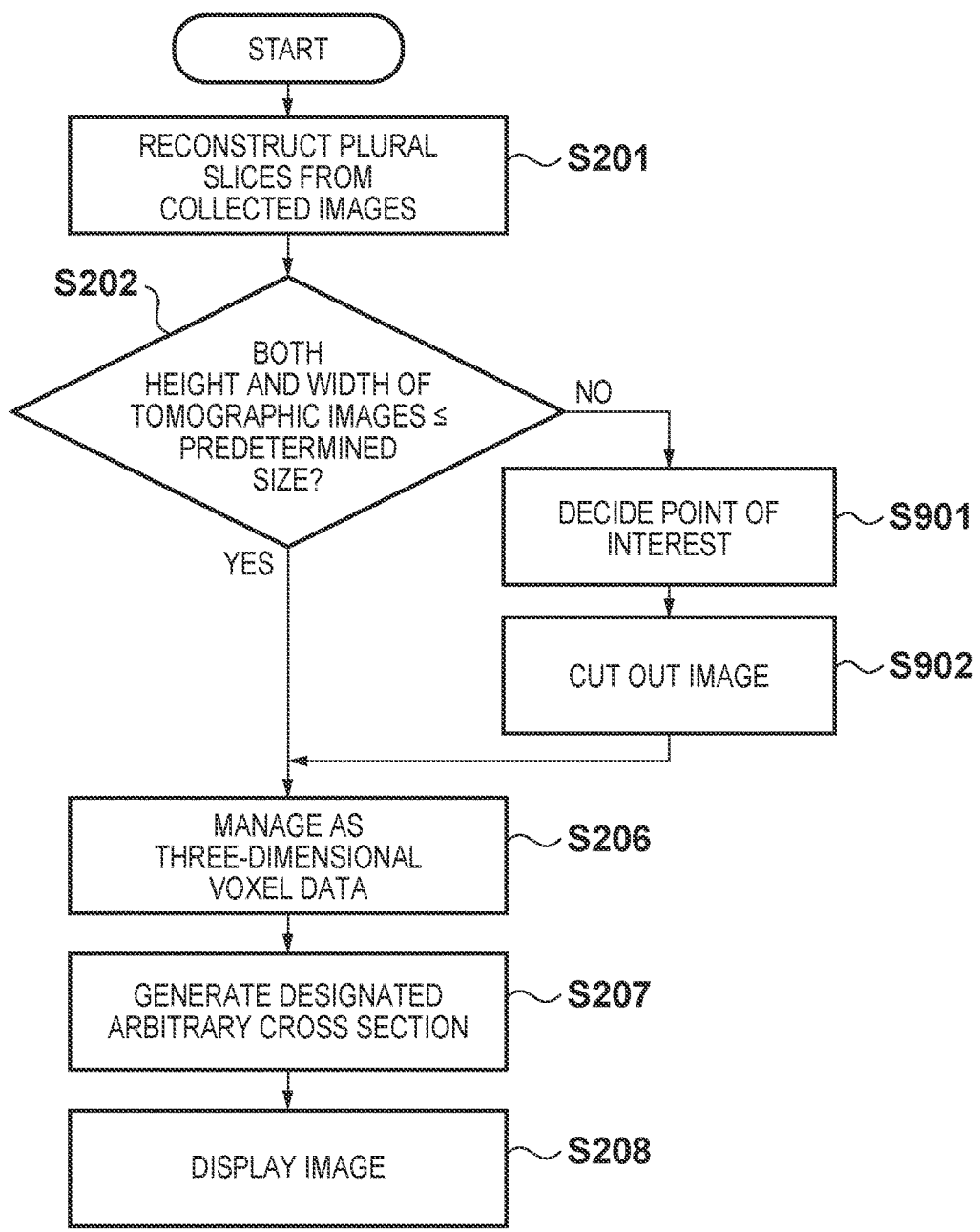
FIG. 12 is a flowchart showing the procedure of processing executed by the X-ray image display apparatus.

The procedure of processing executed by an X-ray image display apparatus according to this embodiment will be described below with reference to the flowchart of FIG. 12. The process contents of steps S201 and S202 and process contents in a case in which the size of tomographic images does not exceed a predetermined size (steps S206 to S208) are the same as in the first embodiment.

In this embodiment, upon determining in step S202 that the size of tomographic images exceeds a predetermined size (NO in step S202), the process advances to step S901. In step S901, an image management unit 103 decides one or more points of interest representing the tomographic images. For example, image analysis is performed using all tomographic images, a plurality of tomographic images, or a specific tomographic image, thereby calculating one or more points of interest in the tomographic images. Alternatively, the point of interest may be decided by displaying a specific tomographic image on an external display device or the like and causing the user to select a point of interest.

Figure 13:
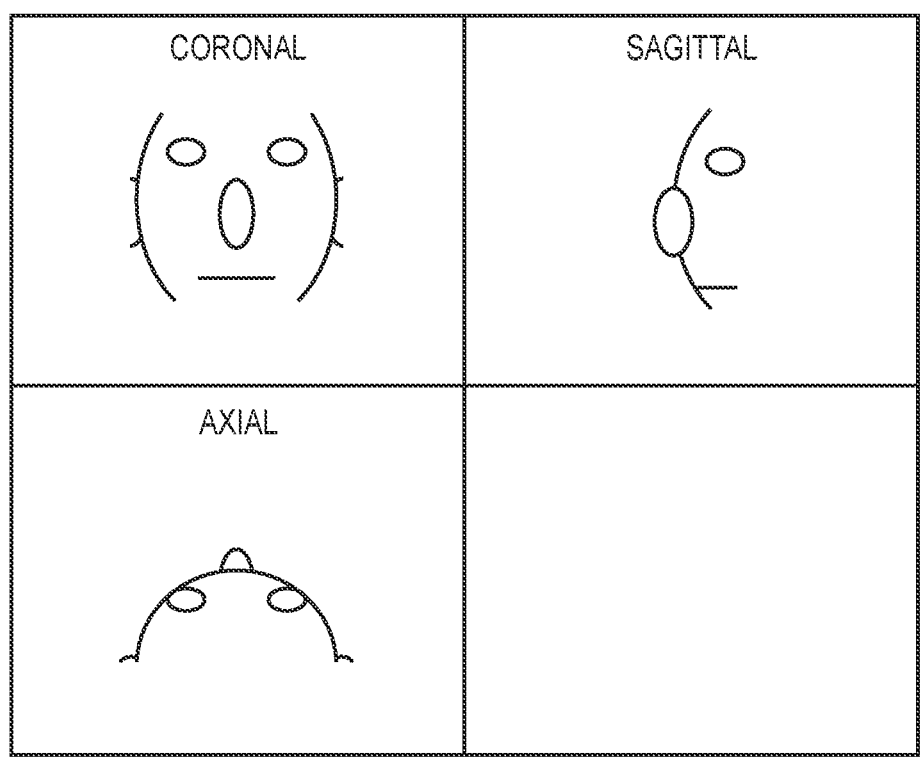
FIG. 13 is a view showing an example in which a plurality of images in different directions are displayed.

Next, the image management unit 103 cuts the tomographic images into the predetermined size such that the point of interest is included or located at the center (step S902), thereby making the tomographic images expandable to three-dimensional voxel data. The processes of steps S206 to S208 are then executed. FIG. 13 shows an example of MPR display in a case in which when the size of tomographic images is equal to or larger than a predetermined size, a region of interest is set at the tip of the nose.

As described above, in this embodiment, if the size of tomographic images exceeds a predetermined size, a partial region of the tomographic images is managed as three-dimensional voxel data. For this reason, according to this embodiment, it is possible to display a cross section in an arbitrary direction for a partial region of the tomographic images even if the size of a 3D texture is limited. Additionally, in this embodiment, since a point of interest is set based on a user specification to decide a region to be managed a three-dimensional voxel data, the user can easily perform detailed analysis for a desired region. Note that in this embodiment, a case has been described in which when the size of tomographic images exceeds a predetermined size, a partial region of the tomographic images is managed as three-dimensional voxel data. However, all the tomographic images may be managed as three-dimensional voxel data by lowering the resolution of the tomographic images.

Third Embodiment

In the first embodiment, the arrangement that manages tomographic images as a plurality of two-dimensional data if their size is equal to or smaller than a predetermined size has been described. In the second embodiment, the arrangement that manages a region of interest as three-dimensional voxel data has been described. In this embodiment, an arrangement that designates a point of interest in an image displayed as two-dimensional data even if the size of tomographic images is equal to or smaller than a predetermined size, and after that, manages the tomographic images as three-dimensional voxel data will be described. Note that many of the operations and arrangements of this embodiment are common to the first embodiment, and arrangements unique to this embodiment will mainly be described.

(Processing Procedure)

Figure 14:
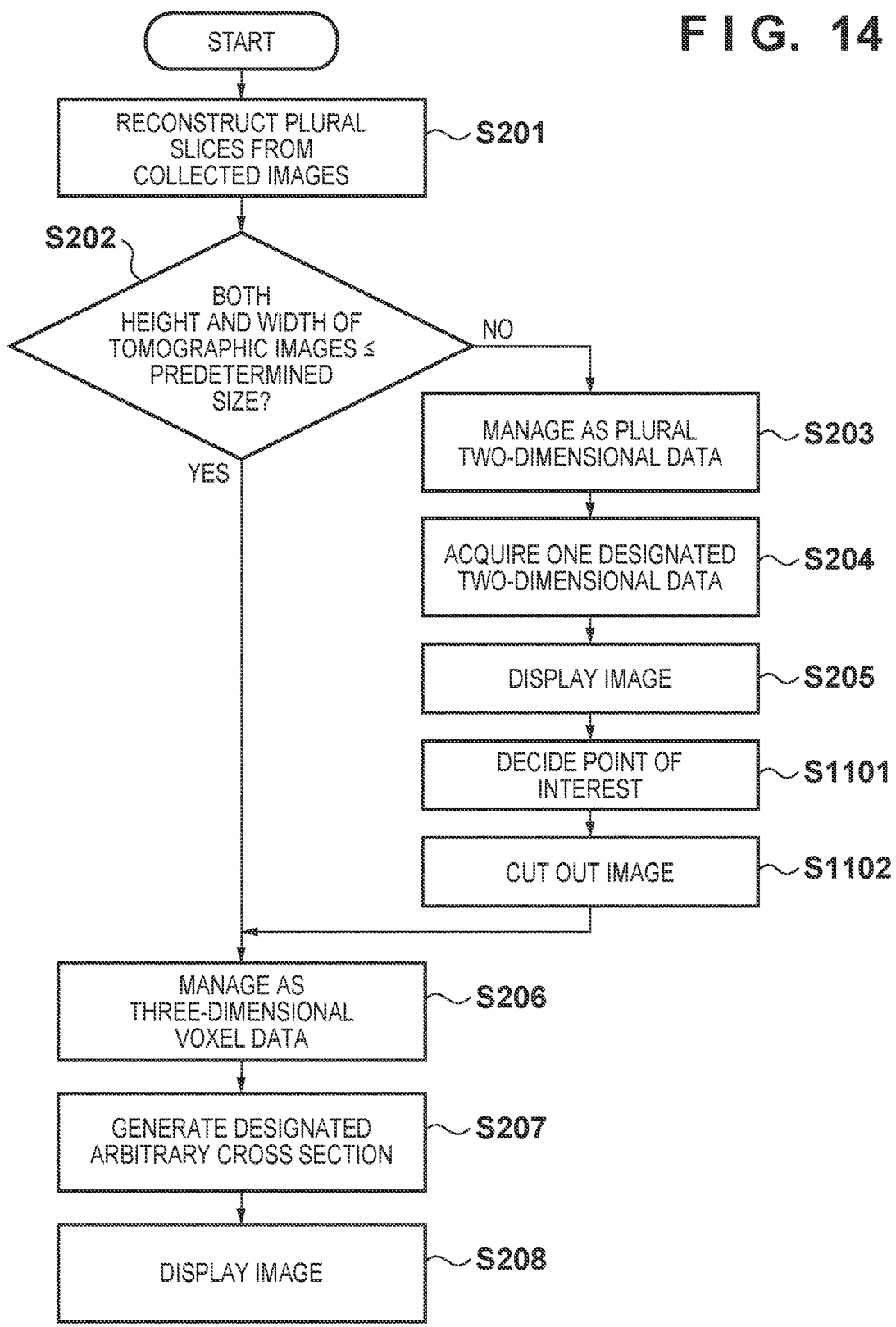
FIG. 14 is a flowchart showing the procedure of processing executed by the X-ray image display apparatus.

The procedure of processing executed by an X-ray image display apparatus according to this embodiment will be described below with reference to the flowchart of FIG. 14. The process contents of steps S201 and S202 and process contents in a case in which the size of tomographic images does not exceed a predetermined size (steps S206 to S208) are the same as in the first embodiment.

Figure 15:
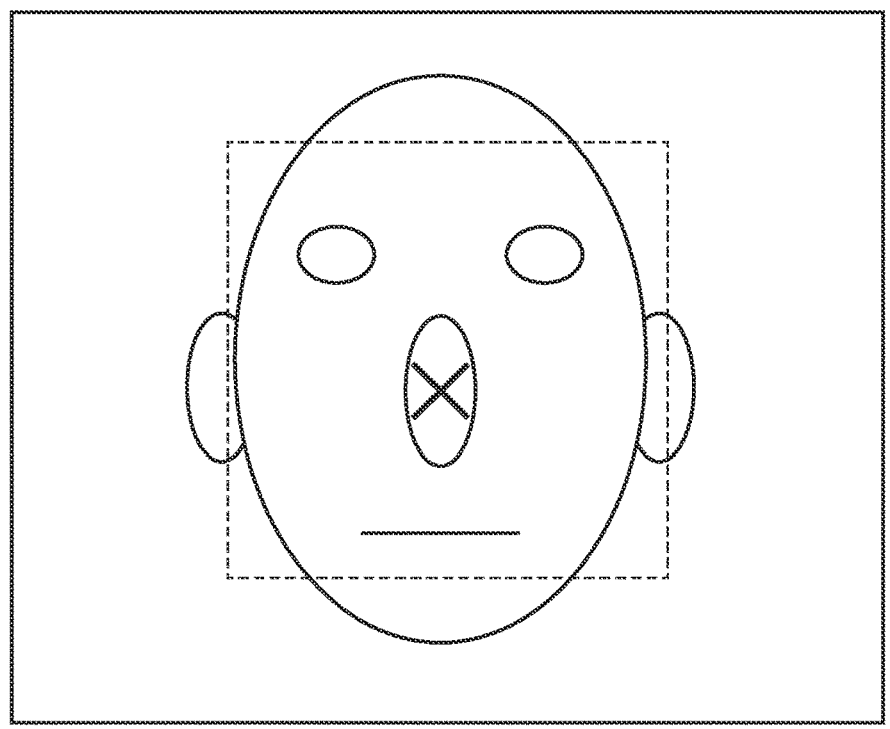
FIG. 15 is a view showing a state in which a point of interest is designated in an image in the coronal direction.

In this embodiment, upon determining in step S202 that the size of tomographic images exceeds a predetermined size (NO in step S202), a coronal image is displayed in steps S203 to S205, as described in the first embodiment. Next, in the display of the coronal image, one or more region of interests are designated on the screen, as shown in FIG. 15 (step S1101). The images are cut into the predetermined size such that the region of interest is included or located at the center (1102). This makes the cut partial region manageable as three-dimensional voxel data. The process advances to step S206. The same processes as in the procedure (steps S206 to S208) in a case in which the size is equal to or smaller than the predetermined size are executed from step S206.

According to this embodiment, it is possible to perform MPR display for tomographic images having a size equal to or smaller than a predetermined size, as shown in FIG. 13, as in the second embodiment. FIG. 13 shows an example of MPR display in a case in which when a region of interest is set at the tip of the nose.

Another Embodiment

The arrangements in which the image management unit 103 manages only one type of a plurality of two-dimensional data and three-dimensional voxel data have been described in the first to third embodiments. However, the two types of data described above may simultaneously be managed.

Figure 16:
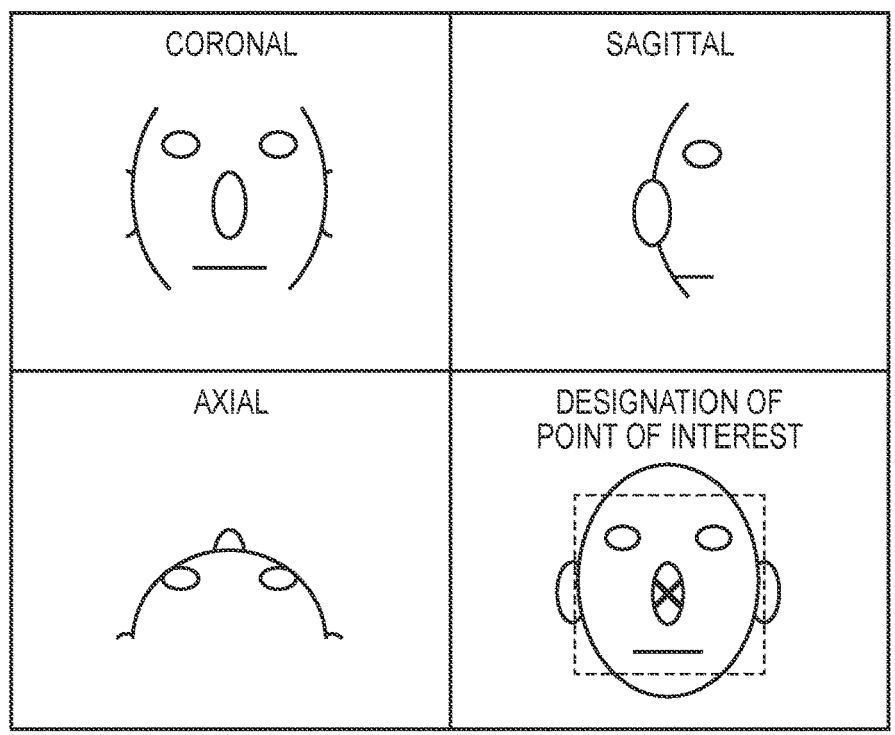
FIG. 16 is a view showing an example in which a plurality of images in different directions are displayed.

When simultaneously managing two-dimensional data and three-dimensional voxel data, if the image size is equal to or smaller than a predetermined size in step S202, there is no particular merit because a plurality of two-dimensional data can be acquired from three-dimensional voxel data. However, if the image size is equal to or larger than the predetermined size, coronal display of two-dimensional data and arbitrary cross section display of cut three-dimensional data can simultaneously be executed. It is therefore possible to simultaneously execute arbitrary cross section display and designation of a region of interest described in the third embodiment, as shown in FIG. 16. Hence, the point of interest can be decided in real time. That is, the user can set a point of interest at an appropriate position while confirming cross section display in the respective directions such as coronal, sagittal, and axial directions, and easily analyze tomographic images.

As described above, in a case in which the image size exceeds a limitation size, each of the above arrangements executes image management/display of two-dimensional data or executes image cutout so as to include a point of interest or locate it at the center such that the point of interest is included in three-dimensional voxel data. Hence, when executing display of an arbitrary cross section using the function of the GPU to display tomographic images of tomosynthesis image capturing, even if the tomographic images have a high resolution and a size more than the limitation size of three-dimensional voxel data of the GPU, effective image display such as arbitrary cross section display can be performed.

(X-Ray Imaging Apparatus)

An X-ray imaging apparatus according to another embodiment of the present invention will be described with reference to FIG. 17.

Figure 17:
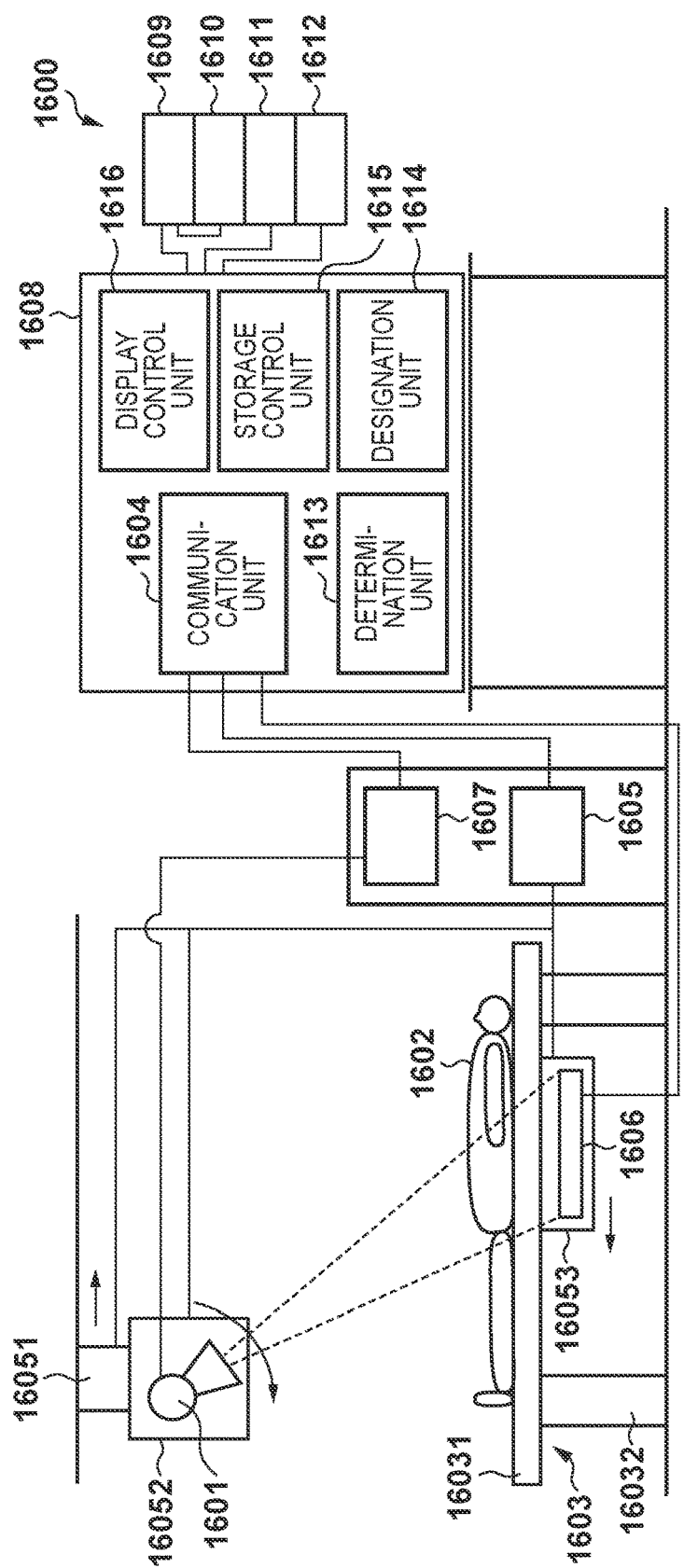
FIG. 17 is a view showing an example of the functional arrangement of an X-ray imaging apparatus.

FIG. 17 shows an example of the functional arrangement of an X-ray imaging apparatus 1600 according to the embodiment. The X-ray imaging apparatus 1600 is an imaging modality including a plurality of elements. The X-ray imaging apparatus 1600 includes an X-ray tube (radiation generator) 1601, an X-ray detector 1606, a mechanism control unit 1605, an X-ray generation control unit 1607, a system control unit 1608, an image processing unit 1609, a display unit 1610, an operation unit 1611, and an image storage unit 1612.

The X-ray tube 1601 includes a target that generates X-rays when electrons collide against it, and a collimator that shapes the generated X-ray beam. The X-ray tube 1601 is fixed to a generator rotation mechanism 16052 and fixed to, for example, the ceiling via a generator moving mechanism 16051 that supports the generator rotation mechanism 16052. The generator moving mechanism 16051 includes a motor that changes the position of the X-ray tube 1601, and the generator rotation mechanism 16052 includes a motor that changes the orientation of the X-ray tube 1601. The X-ray tube 1601 can thus irradiate a subject from a plurality of irradiation angles.

A bed 1603 includes a top plate 16031 on which a subject 1602 lies, and legs 16032 that are fixed to the top plate 16031 and arrange the top plate 16031 at a predetermined height from the floor surface. The top plate 16031 according to the embodiment is arranged in parallel to the floor surface by the legs 16032 so as to capture the subject 1602 in a lying position. Note that when capturing the subject 1602 in a standing position in another embodiment, the bed 1603 is unnecessary.

The X-ray detector (radiation sensor) 1606 includes an X-ray sensor, a driving circuit, an amplifier, an A/D converter, a communication circuit, and a controller. The X-ray sensor has sensitivity in, for example, a region of 14 inches×17 inches. The driving circuit controls the X-ray sensor to a charge accumulation state or read state. The amplifier amplifies the analog output from the X-ray sensor. The A/D converter converts the amplified output into a digital value. The controller is a constituent element that generally controls these elements and is implemented by at least one CPU or FPGA. The X-ray image indicates a digital data group corresponding to one plane of the X-ray sensor or one frame obtained by the A/D converter. Alternatively, the X-ray image indicates an image after the controller has executed correction of an influence of the characteristics of the X-ray sensor, for example, dark correction, gain correction, or defect correction for the digital data. The X-ray image will also be referred to as an X-ray projected image or a projected image in the following explanation.

The X-ray detector 1606 thus detects X-rays and acquires an X-ray image. The X-ray detector 1606 is fixed to an imaging unit moving mechanism 16053. The imaging unit moving mechanism 16053 includes a holding portion for the X-ray detector 1606, and a motor that moves the X-ray detector 1606 along the subject 1602 together with the holding portion.

The mechanism control unit 1605 transmits control signals to the motors of the generator moving mechanism 16051, the generator rotation mechanism 16052, and the imaging unit moving mechanism 16053, and controls the positions of the X-ray tube 1601 and the X-ray detector 1606. Note that in another embodiment, only one of the X-ray detector 1606 and the X-ray tube 1601 may be moved or rotated. When moving or rotating only one unit, the moving mechanism and the rotation mechanism for the other unit are unnecessary.

The X-ray generation control unit 1607 includes a voltage generation unit configured to generate a predetermined voltage to be supplied to the X-ray tube 1601, and a control unit configured to control the operation timing and the magnitude of the voltage be supplied, and causes the X-ray tube 1601 to generate X-rays under predetermined conditions.

The system control unit 1608 generally controls the mechanism control unit 1605, the X-ray detector 1606, and the X-ray generation control unit 1607, and performs tomosynthesis image capturing. The system control unit 1608 includes a communication unit 1604, a determination unit 1613, a designation unit 1614, a storage control unit 1615, and a display control unit 1616. The determination unit 1613 corresponds to the image size determination unit 102, the designation unit 1614 corresponds to the image region designation unit 104, and the storage control unit 1615 corresponds to the image management unit 103.

In addition, the image processing unit 1609, the operation unit 1611 that accepts an operation input by the user, and the image storage unit 1612 that stores a projected image or a tomographic image are connected to the system control unit 1608. The display unit 1610 is connected to the image processing unit 1609. The image processing unit 1609 corresponds to the reconstruction unit 101.

The communication unit 1604 transmits control signals to electrically control the driving circuit, the amplifier, and the A/D converter of the X-ray detector 1606, and receives an X-ray image from the X-ray detector 1606. The communication circuit of the X-ray detector 1606 receives the control signals, and the controller controls the operation timings of the units in accordance with the control signals, thereby acquiring an X-ray image.

Under the control of the system control unit 1608, the mechanism control unit 1605 moves the X-ray tube 1601 in the direction of an arrow in FIG. 17, that is, rightward on the drawing, and moves the X-ray detector 1606 in the direction of another arrow in FIG. 17, that is, leftward on the drawing. During the movement of these units, the X-ray tube 1601 irradiates the subject with X-rays from a plurality of positions, and the X-ray detector 1606 detects the X-rays. X-ray images from a plurality of X-ray irradiation angles are thus acquired.

The system control unit 1608 provides a plurality of X-ray images (to be referred to as projected images) to the image processing unit 1609. The projected images undergo defect correction, gain correction, logarithmic conversion, and the like in advance. Additionally, geometric information including the position of the X-ray tube 1601 and the position information of the X-ray detector 1606 captured for each X-ray image is transmitted from the mechanism control unit 1605 and input to the image processing unit 1609. The image processing unit 1609 reconstructs the acquired projected images based on the geometric information in accordance with a specification from the system control unit 1608, thereby generating tomographic images. The tomographic images or oblique cross-sectional images processed by the image processing unit 1609 are displayed on the display unit 1610 according to the control of the display control unit 1616. The captured projected images are also displayed.

(Example of Hardware Arrangement)

Figure 18:
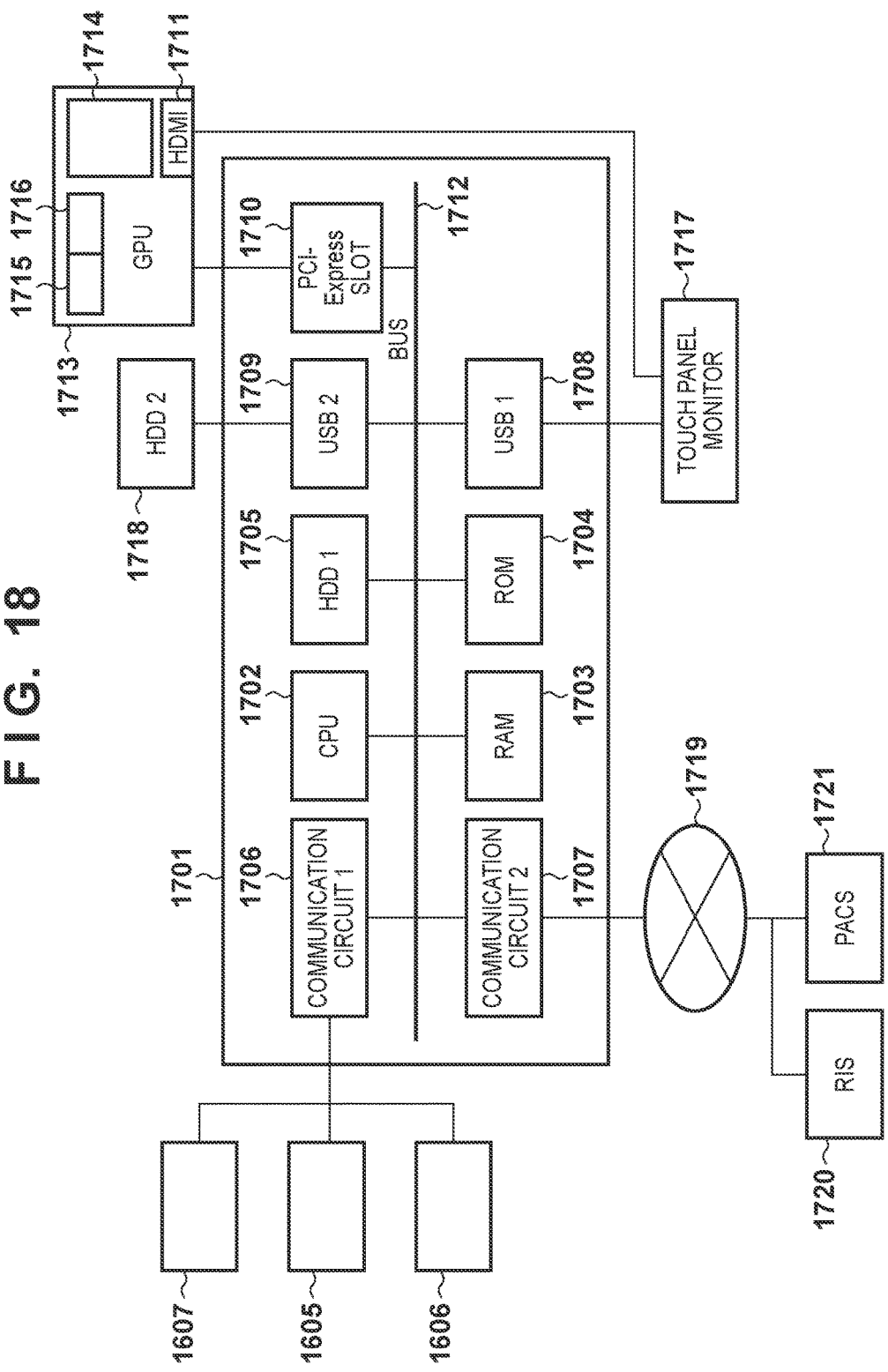
FIG. 18 is a view showing an example of the hardware arrangement of a system control unit.

An example of the hardware arrangement the system control unit 1608 constructed as one physical apparatus will be described with reference to FIG. 18. A control apparatus 1701 will be described below as an arrangement example of the system control unit 1608. The control apparatus 1701 includes a CPU 1702, a RAM 1703, a ROM 1704, a first HDD 1705, a first communication circuit 1706, a second communication circuit 1707, a first USB 1708, a second USB 1709, a PCI-Express slot 1710, and a BUS 1712 that connects these components.

Figure 5:
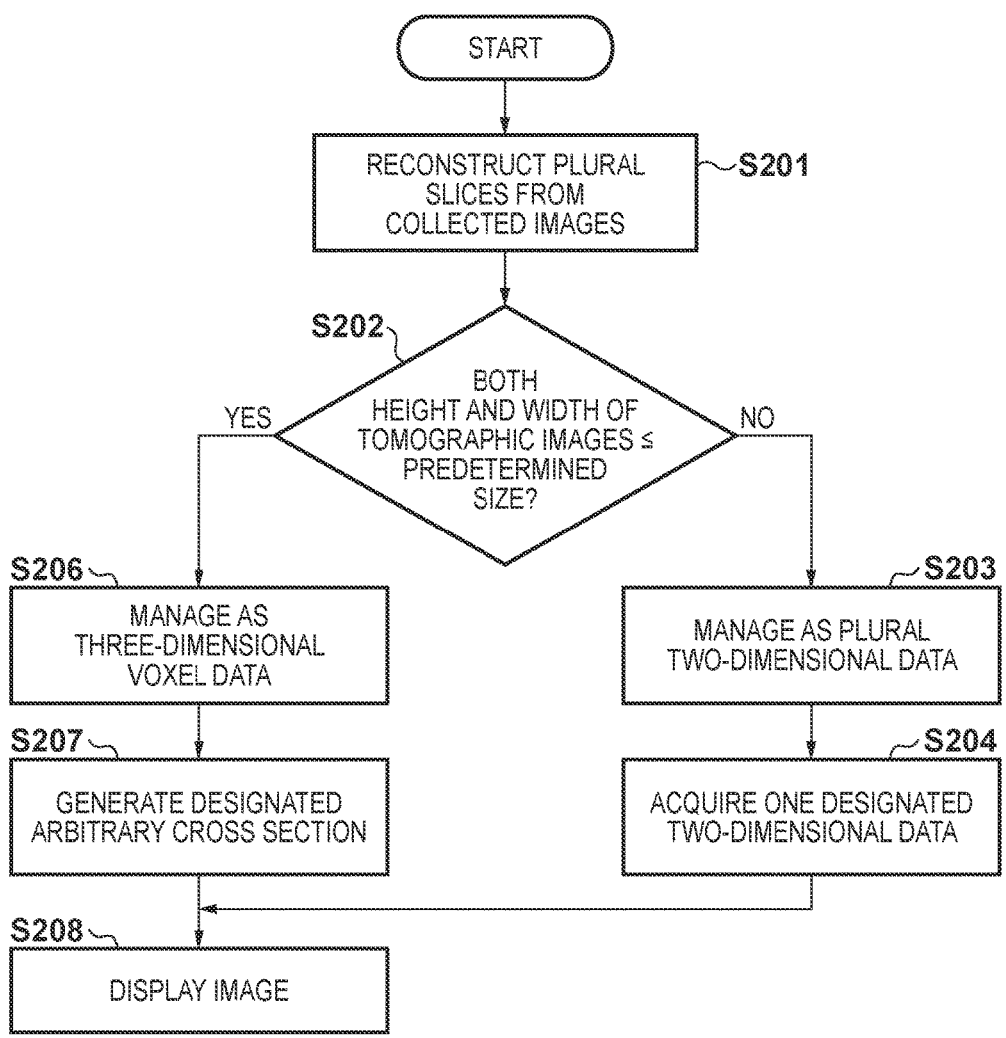
FIG. 5 is a flowchart showing the procedure of processing executed by the X-ray image display apparatus.
Figure 19A:
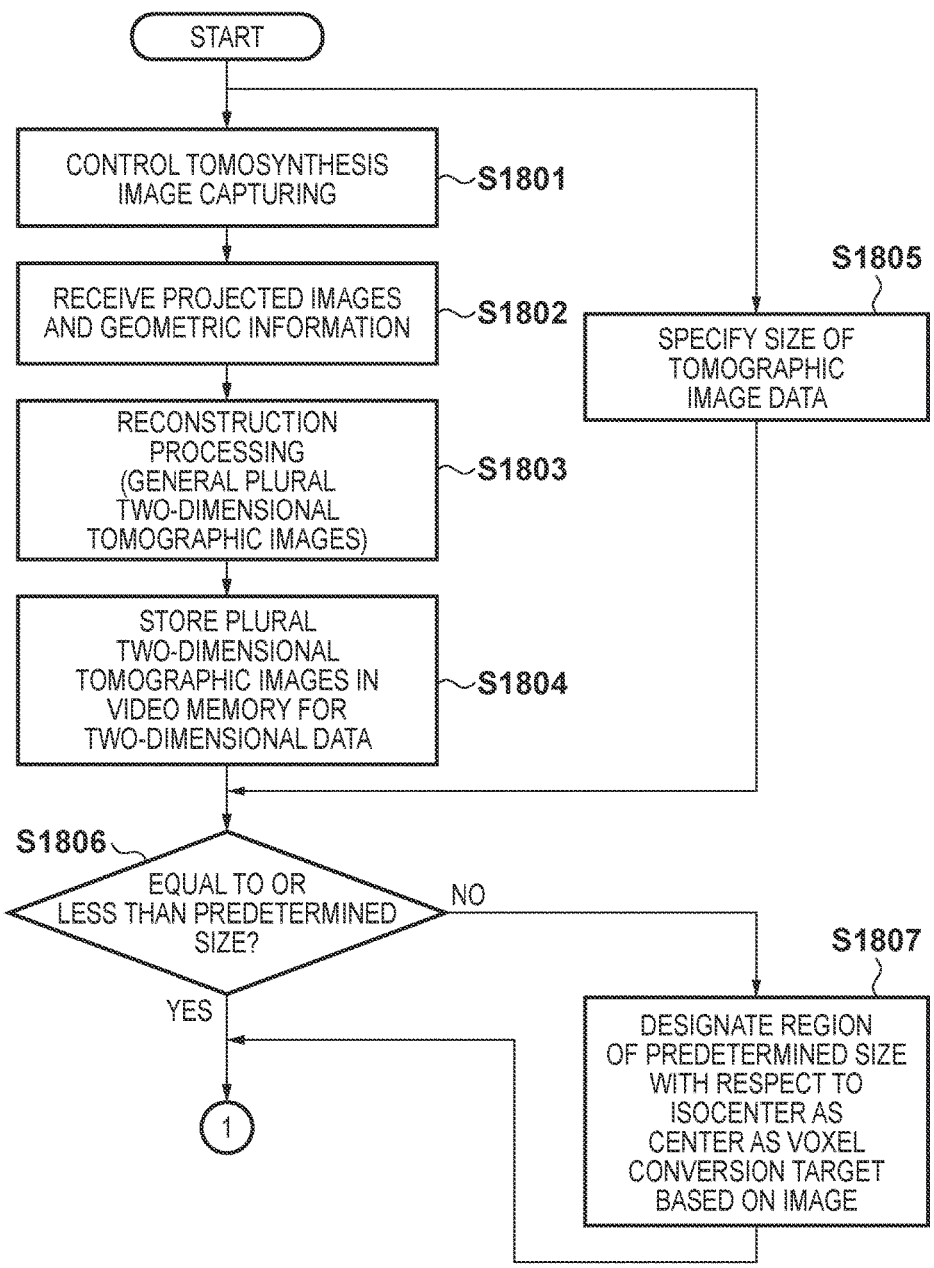

The first HDD 1705 stores a program configured to implement, for example, the processes of the flowcharts of FIGS. 5, 12, and 14 and the processes of the flowcharts of FIGS. 19A and 19B to be described later. When the program is expanded on the RAM 1703 and executed by the CPU 1702, the above-described processes and processes to be described below are implemented. The CPU 1702 controls the units in the control apparatus 1701 and the units connected to the control apparatus 1701 based on the program. With this arrangement, the functions of the communication unit 1604, the determination unit 1613, the designation unit 1614, the storage control unit 1615, and the display control unit 1616 of the system control unit 1608 are implemented.

The first communication circuit 1706 is a communication circuit that communicates with the mechanism control unit 1605, the X-ray detector 1606, and the X-ray generation control unit 1607 according to the control of the CPU 1702 based on the above-described program, and corresponds to the communication unit 1604. The first communication circuit 1706 transmits a control signal to the X-ray detector 1606, receives a plurality of projected images obtained by tomosynthesis image capturing from the X-ray detector 1606, and receives geometric information representing the positional relationship of the imaging system upon capturing each of the plurality of received projected images. The imaging system indicates the X-ray tube 1601 and the X-ray detector 1606.

A GPU 1713 is an image processing circuit that performs reconstruction processing of tomographic image data according to the control of the CPU 1702 based on the above-described program, and corresponds to the image processing unit 1609. The GPU 1713 includes an HDMI® 1711, an image processor 1714, a video memory 1715 for 2D data, and a video memory 1716 for 3D data, and is connected to the PCI-Express slot 1710.

The GPU 1713 reconstructs tomographic image data based on a plurality of projected images and geometric information according to the control of the CPU 1702. Here, the tomographic image data may be generated as three-dimensional voxel data or a plurality of two-dimensional tomographic images. The pixel pitch, slice pitch, slice count, voxel size, and reconstruction range of the tomographic image data are set by operation inputs from the operation unit 1611 as image processing conditions. Alternatively, they are set by the CPU 1702 in association with imaging conditions.

The CPU 1702 operates under the control of the above-described program. The CPU 1702 functions as the determination unit 1613 that determines, based on the size of reconstructed tomographic image data, whether the size of the tomographic image data reconstructed based on a plurality of projected images obtained by tomosynthesis image capturing exceeds a predetermined size.

The predetermined size is determined by, for example, the GPU 1713 or an API that provides an instruction set to the GPU 1713. In Direct 3D 11 that is one of interfaces to a GPU in Windows®, a 3D texture has a size limitation to 2048×2048×2048 pixels. Note that a 2D texture also has a size limitation to 16384×16384×N. N depends on the capacity of a video memory mounted on a graphic board. For example, N is 511 in Quadro 5000 available from NVIDIA, and 144 in Geforce GTX 660.

The CPU 1702 also functions as the designation unit 1614 that designates a partial region of reconstructed tomographic image data based on the tomographic image data under the control of the above-described program. The CPU 1702 acquires the information of the isocenter of tomosynthesis image capturing from the geometric information received by the first communication circuit 1706, and designates a partial region based on the isocenter. In one embodiment, a three-dimensional partial region whose center is set at the isocenter and whose side in the height direction in FIG. 17 has a length corresponding to twice longer than the distance between the isocenter and the top plate is designated. As for the remaining sides, for example, one side in the depth direction in FIG. 17 has a length equal to the short side length of the top plate 16031, and the length of the other remaining side is determined within the range of the size limitation. If the image size becomes larger than the predetermined size even by the above-described method, a region within the size limitation with respect to the isocenter as the center may be designated. Note that the isocenter is a point located on a line that connects the X-ray focus of the X-ray tube 1601 and the central position of the detection region of the X-ray detector 1606, and indicates a position as the center of tomosynthesis image capturing. During tomosynthesis image capturing, the mechanism control unit 1605 controls the positional relationship between the X-ray tube 1601 and the X-ray detector 1606 such that the line that connects the X-ray focus and the central position of the detection region always passes through the isocenter.

In another embodiment, the CPU 1702 or the GPU 1713 extracts an object region from projected images by a known method, obtains an object region in tomographic images by back projection processing, and designates a partial region including the object region. This can eliminate regions unnecessary for diagnosis and contribute to efficient oblique display or 3D display. In another embodiment, the CPU 1702 or the GPU 1713 extracts an exposure field, and designates a partial region including the exposure field. This makes it possible to more reliably perform oblique display or 3D display suitable for diagnosis by using a result of exposure field extraction that is generally more accurate than object region extraction, considering the risk of a failure in object region extraction.

The CPU 1702 also stores the tomographic image data of the designated partial region in the video memory 1716 for 3D data in the GPU 1713 as three-dimensional voxel data. This function corresponds to the storage control unit 1615. If tomographic image data are reconstructed as two-dimensional tomographic image data, the data of the designated partial region out of the two-dimensional tomographic image data is converted into three-dimensional voxel data. Note that if the tomographic image data are reconstructed as three-dimensional voxel data from the beginning, the designated partial region is extracted and stored in the video memory 1716 for 3D data.

The first USB 1708 and the HDMI® 1711 are connected to a touch panel monitor 1717. The first USB 1708 acquires an operation input to the touch panel. The HDMI® 1711 outputs display data to the monitor. Under the control of the CPU 1702 and the above-described program, the touch panel monitor 1717 functions as the display unit 1610 and the operation unit 1611.

The CPU 1702 acquires an operation input that specifies an oblique section that crosses a cross section (a coronal section in the example of FIG. 17) along the object at an angle other than 90° as a display target out of the reconstructed tomographic image data. Based on the information of the operation input, the CPU 1702 specifies the position and orientation of the oblique section as the generation target.

The CPU 1702 outputs a command to cause the GPU 1713 to display the oblique image of the designated oblique section. The GPU 1713 generates the oblique image in accordance with the command, and causes the touch panel monitor 1717 to display the oblique image via the HDMI® 1711. Concerning this point, the CPU 1702, the program, and the GPU 1713 correspond to the display control unit 1616.

In addition, a second HDD 1718 is connected to the second USB 1709. The second HDD 1718 corresponds to the image storage unit 1612.

In another embodiment, the control apparatus 1701 includes the second communication circuit 1707 connected to an intra-hospital network 1719. The CPU 1702 causes the second communication circuit 1707 to output projected image data, tomographic image data, or oblique image data to a PACS (image management server) 1721 to present the images to diagnosis on a PACS viewer. The second communication circuit 1707 also receives an imaging order of tomosynthesis image capturing from an RIS (Radiology Information System) 1720 via the intra-hospital network 1719. An imaging part, a reconstruction range, and the like are set based on the imaging order.

(Processing Procedure)

The procedure of processing of the system control unit 1608 (control apparatus 1701) will be described with reference to the flowchart of FIGS. 19A and 19B.

In step S1801, the system control unit 1608 transmits control signals to the mechanism control unit 1605, the X-ray detector 1606, and the X-ray generation control unit 1607 via the communication unit 1604 or mediates control signals, thereby executing tomosynthesis image capturing. By the tomosynthesis image capturing, the X-ray detector 1606 outputs a plurality of projected images, and the mechanism control unit 1605 outputs geometric information representing the positional relationship of the imaging system upon capturing each projected image. The control signals as the inputs are, for example, the preset number of projected images to be captured, imaging angle, and X-ray irradiation conditions. The imaging angle is set in a form of ±0° (X<90) by setting 0° to a vertical downward direction from the X-ray tube 1601.

In step S1802, the communication unit 1604 receives a plurality of projected images from the X-ray detector 1606 and geometric information representing the positional relationship of the imaging system upon capturing each projected image from the mechanism control unit 1605.

In step S1803, the image processing unit 1609 reconstructs a plurality of two-dimensional tomographic image data based on the plurality of projected image sand geometric information. If the object is set in a lying position, as shown in FIG. 17, coronal images that are cross sections parallel to the detector are obtained. The pitch of the coronal images (the interval between adjacent coronal images) and the number of coronal images to be generated are set in advance or in association with the information of the imaging part and the like.

In step S1804, the storage control unit 1615 stores the plurality of generated two-dimensional tomographic image data in the video memory 1715 for two-dimensional data in the GPU 1713 that constructs the image processing unit 1609.

If the video memory 1715 for two-dimensional data is short, the designation unit 1614 designates some image data including two-dimensional tomographic image data at the isocenter, and stores them in the video memory 1715. This is because the isocenter is a position at which a tomosynthesis image is considered to attain the highest image quality, and is normally arranged at a position necessary for diagnosis.

The process of step S1805 is performed in parallel to the processes of steps S1801 to S1804 or after the processes of steps S1801, S1802, S1803, and S1804. In step S1805, the determination unit 1613 specifies the data size of the tomographic image data. The data size is represented by the bit depth of each pixel value, the numbers of rows and columns of pixels, and the number of pixels in the depth direction. The bit depth and the numbers of rows and columns of pixels are determined based on the information of reconstruction conditions such as the original image size and the reconstruction range. The number of pixels in the depth direction can be set to, for example, the number of slices. When performing interpolation between slices, the number of pixels in the depth direction increases by the number of interpolated slices. The number of pixels in the depth direction is determined based on the number of slices and the number of interpolated slices.

In step S1806, the determination unit 1613 determines whether the specified data size is equal to or smaller than a predetermined size. Upon determining that the specified data size is not equal to or smaller than the predetermined size (NO in step S1806), the process advances to step S1807, and the designation unit 1614 designates an image region to be converted into three-dimensional voxel data. For example, a partial region of a predetermined size is designated with respect to the isocenter as the center.

In another embodiment, the determination unit 1613 determines, in step S1806, which one of the number of rows, the number of columns, and the size in the depth direction out of the two-dimensional tomographic image data exceeds the predetermined size. Upon determining that at least one of the number of rows and the number of columns exceeds the predetermined size, the determination unit 1613 further determines whether the size of the region of exposure field or the region of the object region out of the two-dimensional tomographic image data exceeds a predetermined number of rows or columns.

When performing such processing, the image processing unit 1609 extracts at least one of the exposure field and the object region from each projected image by a known method, and compares it with a tomographic image, thereby extracting at least one of the region of exposure field and the object region of the tomographic image. For example, the image processing unit 1609 specifies at least one of region of exposure field and the object region based on the projected images and the geometric information. Separately, the image processing unit 1609 generates volume data from the two-dimensional tomographic image data. The volume data is aligned and compared with the specified at least one of the region of exposure field and the object region, thereby specifying at least one of the region of exposure field and the object region in the volume data.

The determination unit 1613 determines whether the specified at least one of the region of exposure field and the object region has a size equal to or smaller than the predetermined size of the number of rows or columns. Upon determining that the size is equal to or smaller than the predetermined size, the at least one of the region of exposure field and the object region is designated as a partial region. In a case in which both the region of exposure field and the object region are extracted, if the size of the region of exposure field is equal to or smaller than the predetermined size, the region of exposure field is designated as a partial region. Upon determining that the size of the region of exposure field is larger than the predetermined size, but the size of the object region is equal to or smaller than the predetermined size, the object region is designated as a partial region.

In a case in which the size in the depth direction exceeds a predetermined size as well, at least one of the region of exposure field and the object region is designated as a partial region, as in the above-described process. In another embodiment, the determination unit 1613 determines whether the size in the depth direction is equal to or smaller than a predetermined size if interpolation processing is not performed.

In this way, it is possible to appropriately display an oblique section while decreasing adverse effects on diagnosis as much as possible. That is, the arrangement according to this embodiment designates a partial region of tomographic image data upon determining that the size of the tomographic image data is not equal to or smaller than a predetermined size, stores only the data of the partial region as three-dimensional voxel data, and displays the tomographic image of an oblique section. It is therefore possible to appropriately display cross sections that need 3D display even if the memory capacity is limited.

On the other hand, upon determining in step S1806 that the data size is equal to or smaller than the predetermined size (YES in step S1806), the process advances to step S1808, and the storage control unit 1615 converts all the reconstructed tomographic image data into three-dimensional voxel data. This conversion processing may be performed by, for example, the image processor 1714 of the GPU 1713 that constructs the image processing unit 1609. In step S1809, the storage control unit 1615 stores the converted three-dimensional voxel data in the video memory 1716 for three-dimensional data.

In step S1810, the display control unit 1616 causes the display unit 1610 to display the two-dimensional tomographic image data. Note that this processing is enabled when the two-dimensional tomographic image data is stored in the video memory 1715 for two-dimensional data in step S1804. Hence, when this processing is performed in parallel to the processes of steps S1805 to S1809, the delay time from tomosynthesis image capturing to tomographic image display can be made shorter. The display control unit 1616 causes the display unit to, for example, selectively display arbitrary tomographic image data in accordance with a first operation input from the operation unit 1611 or adjacently display a plurality of tomographic image data in accordance with a second operation input.

In step S1811, the system control unit 1608 determines whether a specification input (third operation input) that specifies an oblique section as a display target has been done. The third operation input includes the information of the position and orientation of the cross section of the display target, and the system control unit 1608 acquires the information from the third operation input. Upon determining that the third operation input has been done (NO in step S1811), the process advances to step S1814.

There is a possibility that an oblique section that is not included in the partial region converted into three-dimensional voxel data is designated. In one embodiment, when an oblique section can be specified on a GUI, limitations are imposed on the input range on the GUI. To do this, the display control unit 1616 imposes limitations on the GUI so as to prohibit an oblique section outside the designated partial region from being designated. For example, consider a case in which an oblique section passing through the isocenter is designated. Assume that an oblique section crossing a coronal plane at an angle larger than ±30° does not fall within the partial region converted into three-dimensional voxel data. In this case, an upper limit value of 30° and a lower limit value of −30° are set for a slider bar configured to specify an oblique section. The display control unit 1616 controls to prohibit an angle larger than ±30° from being designated by an operation input. In this way, limitations are imposed on the input range on the GUI, thereby allowing the user to designate a desired oblique section within the displayable range without selecting any cross section that the apparatus cannot display.

Note that in this case, upon determining in step S1811 that a specification input of an oblique section has been done, the process advances to the process of step S1812.

Other embodiments will be described as the processes of steps S1815 to S1817. Upon determining in step S1811 that a specification input of an oblique section has been done (YES in step S1811), the process from step S1815 is performed.

In step S1815, the system control unit 1608 determines whether an oblique section within a range included in the partial region designated by the designation unit 1614 and converted into three-dimensional voxel data by the storage control unit 1615 has been specified as the third operation input. Upon determining that the oblique section exists, that is, three-dimensional voxel data corresponding to the oblique section exists (YES in step S1815), the process advances to step S1812.

On the other hand, upon determining that three-dimensional voxel data corresponding to the specified oblique section does not exist or is short (NO in step S1815), in step S1816, the designation unit 1614 designates a partial region including the specified oblique section anew. In this way, if a cross section including a region outside the partial region of the tomographic image data is supported, a new partial region is designated again from the tomographic image data.

As one form of redesignation, the system control unit 1608 determines whether a partial region including both the specified cross section and the isocenter exists. Upon determining that such a partial region exists, the designation unit 1614 designates the partial region. On the other hand, upon determining that such a partial region does not exist, a partial region including at least the specified cross section is designated.

Note that in some cases, particularly, when the angle of the oblique section with respect to the coronal section is too large, the image size may exceed the predetermined size in the height direction, and it may be impossible to designate a partial region including the specified oblique section. In this case, the partial region designated in advance is maintained without performing redesignation. Alternatively, a partial region having, at the center, the central position of the specified cross section is designated. In this case, an oblique cross-sectional image is designated only within the range of the designated partial region.

In step S1817, the storage control unit 1615 overwrites the newly designated partial region in the video memory 1716 for three-dimensional data in the GPU 1713. After that, the process advances to step S1812.

In step S1812, the display control unit 1616 specifies generation and display of the designated oblique section to the image processing unit 1609. The image processing unit 1609 generates the cross-sectional image of the specified oblique section. At this time, the image processing unit 1609 can generate the oblique section from the three-dimensional voxel data stored in the video memory 1716 for three-dimensional data in the GPU 1713. For this reason, the oblique section can be generated at a higher speed as compared to a case in which the oblique section is generated from the video memory 1715 for two-dimensional data or an external storage unit.

In step S1813, the image processing unit 1609 outputs the oblique cross-sectional image to the display unit 1610 in accordance with a specification from the display control unit 1616, thereby causing the display unit 1610 to display the oblique section cross-sectional image.

On the other hand, upon determining in step S1811 that a specification input of an oblique section has not been done, the process advances to step S1814.

In step S1814, the system control unit 1608 determines whether an end specification is input. If an end specification is input (YES in step S1814), the processing ends. If an end specification is not input (NO in step S1814), the process returns to the determination process of step S1811.

Figure 20:
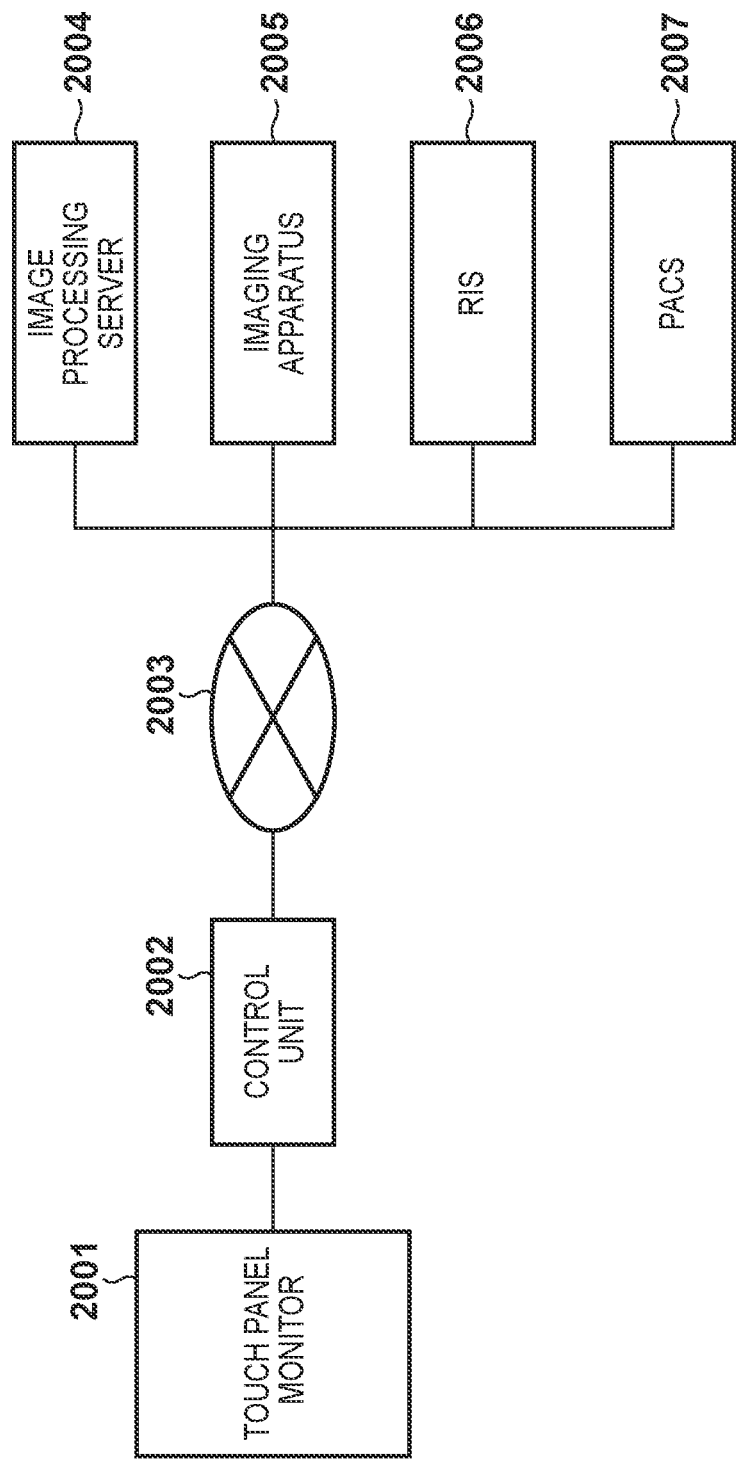
FIG. 20 is a view showing an example of an X-ray imaging system formed from systems distributed on a network.

As another embodiment, a system including a plurality of apparatuses that communicate via a communication network will be described with reference to FIG. 20. The system shown in FIG. 20 is an X-ray imaging system formed from systems distributed on a network. In the system shown in FIG. 20, a control unit 2002 connected to a touch panel monitor 2001 serving as both a display unit and an operation unit is connected to an image processing server 2004, an imaging apparatus 2005, an RIS 2006, and a PACS 2007 via a network 2003. Reconstruction processing by the reconstruction unit 101 shown in FIG. 1 and processing by the image size determination unit 102 are performed by the image processing server 2004. Processing of the image management unit 103 or image region designation unit 104 may also be performed by the image processing server 2004. The image display unit 105 corresponds to the touch panel monitor 2001. The control unit 2002 transmits/receives information to/from the image processing server 2004, the imaging apparatus 2005, the RIS 2006, the PACS 2007, and the like, and also performs display control to cause the touch panel 2001 to display received information. The network 2003 can be either an intranet in a hospital or a network such as a VPN including the Internet. The imaging apparatus 2005 is an imaging apparatus for performing tomosynthesis as shown in FIG. 17. Note that the apparatuses need only be connected via a network and may exist in different countries.

Figure 21:
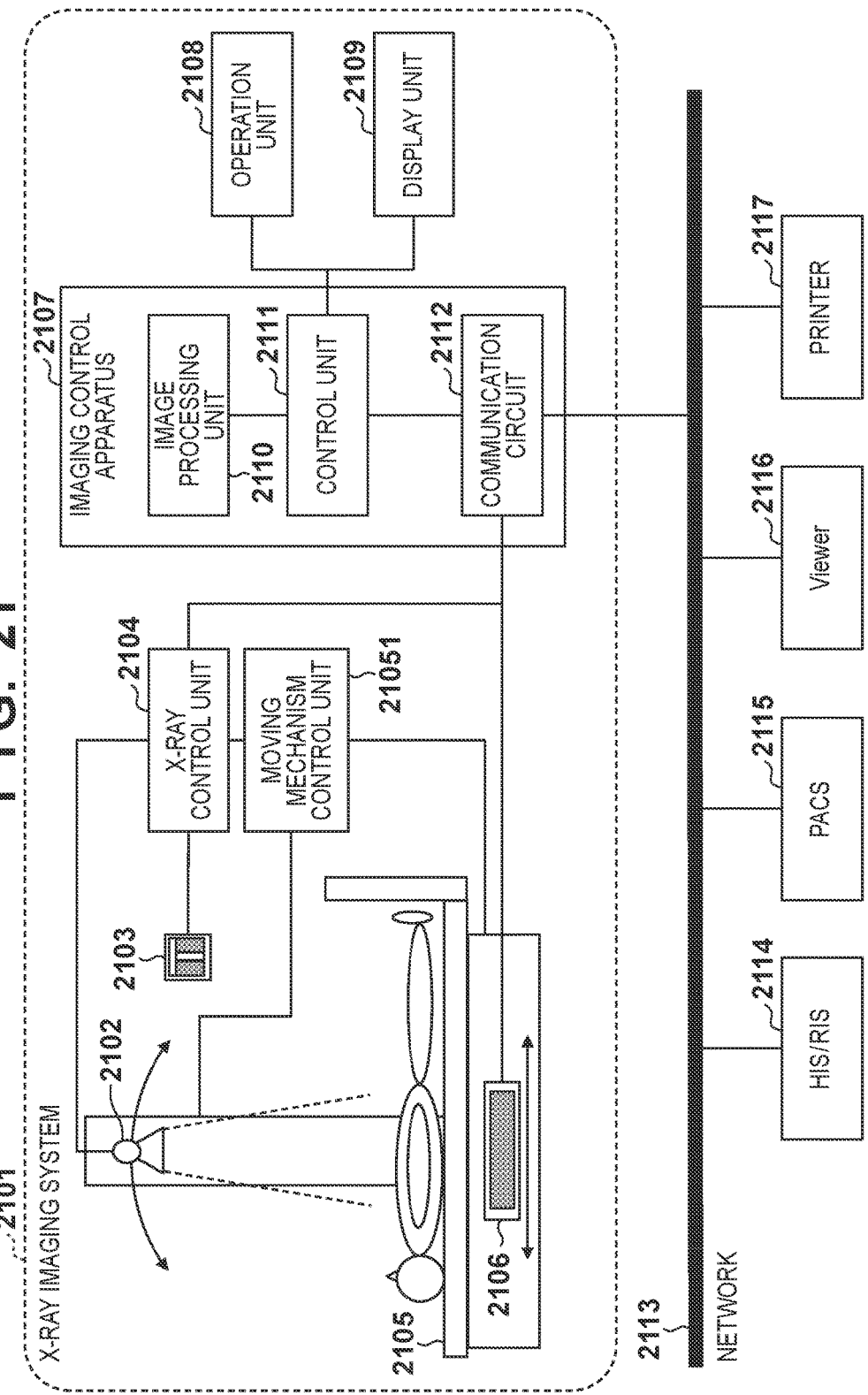
FIG. 21 is a view showing the arrangement of an X-ray imaging system according to an embodiment of the present invention.

The arrangement and operation of an X-ray imaging system that is an example of a radiation imaging system according to an embodiment of the present invention will be described with reference to FIG. 21. Note that the X-ray imaging system will sometimes be referred to as an X-ray imaging apparatus.

An X-ray imaging system 2101 is an imaging system which includes an X-ray generation apparatus 2102, an X-ray detector 2106, and an imaging control apparatus 2107 and is capable of performing tomosynthesis image capturing. The imaging control apparatus 2107 is a control apparatus that controls tomosynthesis image capturing, and includes a communication circuit 2112 that communicate with the radiation detector 2106, an image processing unit 2110 including a graphic processing unit (GPU), and a control unit 2111 including at least one central processing unit. The control unit 2111 is a control circuit (control unit) that controls the radiation detector 2106, image processing by the GPU, and display contents to be displayed by a display unit 2109. The communication circuit 2112 acquires, from the radiation detector 2106, a plurality of projected images of a subject obtained by tomosynthesis image capturing. The control unit 2111 can cause the image processing unit 2110 to execute a plurality of reconstruction methods. One of the reconstruction methods is a first reconstruction method of reconstructing three-dimensional voxel data based on a plurality of projected images. The other is a second reconstruction method of reconstructing a plurality of two-dimensional tomographic image data based on a plurality of projected images.

The control unit 2111 selects one of the first reconstruction method and the second reconstruction method corresponding to a plurality of projected images. When the first reconstruction method is selected, the control unit 2111 causes the image processing unit 2110 to generate a two-dimensional tomographic image along the detection plane of the radiation detector 2106 and an oblique image crossing the detection plane based on three-dimensional voxel data reconstructed by the image processing unit 2111. When the first reconstruction method is selected, the control unit 2111 causes the display unit to display the two-dimensional tomographic image and the oblique image generated by the image processing unit 2110. When the second reconstruction method is selected, the control unit 2111 causes the display unit to display at least one of the plurality of two-dimensional tomographic image data reconstructed by the image processing unit 2110. Accordingly, in the first reconstruction method, since three-dimensional voxel data is generated, a necessary cross-sectional image can appropriately be generated in accordance with a user specification. In the second reconstruction method, since two-dimensional tomographic images are reconstructed, for example, an oblique image of higher image quality can be generated.

The X-ray generation apparatus 2102 includes a target that generates X-rays when electrons collide against it, and a stop that shapes the generated X-ray beam, and irradiates an object with X-rays shaped into a conical beam or quadrangular pyramidal beam. The X-ray generation apparatus 2102 is fixed to an imaging table 2105 and irradiates the object with X-rays while being moved by a moving mechanism controlled by a moving mechanism control unit 21051. Along with X-ray irradiation, the moving mechanism control unit 21051 transmits, to an X-ray control unit 2104, imaging execution conditions such as a tube voltage and a tube current and position information such as an imaging angle and an X-ray source moving distance. The X-ray control unit 2104 is connected to the X-ray generation apparatus 2102, an X-ray irradiation switch 2103, and the imaging control apparatus 2107, and controls the start of X-ray irradiation and the end of irradiation and transmits the imaging execution conditions and the position information.

The X-ray generation apparatus 2102 may receive default imaging conditions and default position information from the X-ray control unit 2104 and perform imaging preparation processing. The X-ray irradiation switch 2103 may be connected to the X-ray generation apparatus 2102, and transmits an irradiation start notification or an irradiation end notification to the X-ray control unit 2104. When the operator presses the switch, the X-ray irradiation switch 2103 transmits an irradiation start notification. When the operator releases the switch, the X-ray irradiation switch 2103 transmits an irradiation end notification. The X-ray control unit 2104 may receive default imaging conditions and default position information from the imaging control apparatus 2107 and notify the X-ray generation apparatus 2102 of them.

The X-ray detector 2106 is an X-ray sensor that detects X-rays transmitted through a subject and converts then into X-ray image data, and includes a scintillator that converts X-rays into visible light, and a sensor array that converts the visible light into an electrical signal. The X-ray detector 2106 is connected to the imaging control apparatus 2107 via a cable or wirelessly, and changes, for example, the supply state of power to the sensor array according to the control of the imaging control apparatus 2107. The X-ray detector 2106 transmits the X-ray image data to the imaging control apparatus 2107. For example, the communication circuit 2112 transmits an X-ray irradiation preparation request or an X-ray irradiation preparation cancel request to the X-ray control unit 2104 and the X-ray detector 2106 via a communication I/F. The communication circuit 2112 also receives X-ray image data, imaging information, and position information from the X-ray control unit 2104 and the X-ray detector 2106.

The X-ray detector 2106 may transmit the converted X-ray image data and imaging execution information such as a read area and a binning size to the imaging control apparatus 2107. In addition, position information such as an X-ray detector moving distance may be transmitted to the imaging control apparatus 2107 together with the X-ray image data. Furthermore, the X-ray detector 2106 may perform imaging preparation processing upon receiving default position information from the imaging control apparatus 2107.

An operation unit 2108 accepts an operation input to set a user's desired imaging condition or an image processing condition such as a reconstruction condition, confirm a projected image or a reconstructed image, or transmit an image to an external device. The operation unit 2108 is formed by a keyboard, a mouse, a touch panel integrated with, for example, the display unit 2109, and the like or a combination thereof. The display unit 2109 may display a user interface of X-ray imaging control software. The display unit 2109 can be a single monitor or a monitor built in the X-ray imaging apparatus. A plurality of monitors configured to display captured images may be connected to one imaging control apparatus 2107. Captured images and past images may be preview-displayed on different monitors. At this time, the display unit 2109 determines which image is to be displayed on which monitor based on a notification from the imaging control apparatus 2107, and displays the image on the determined monitor.

In addition, the X-ray imaging system 2101 may be connected from the imaging control apparatus 2107 to an HIS/RIS 2114, a PACS 2115, a Viewer 2116, and a printer 2117 via a network 2113. The HIS/RIS 2113 is a hospital/radiology information system that manages information such as subject information and test request information in the radiology. The PACS 2115 is a server mainly aiming at image storage. The Viewer 2116 is connected to the PACS 2115 to mainly execute an image examination operation or detailed post-processing of images captured by the X-ray imaging system 2101 or diagnostic operation using a high-resolution monitor. The printer 21117 prints X-ray image data or tomosynthesis image data. In this case, the communication circuit 2112 of the imaging control apparatus 2107 receives test request information, transmits test execution information, or outputs X-ray image data or tomosynthesis image data via the network 2113.

The X-ray imaging system may include the imaging table 2105 that is a rest to place a subject. The table is unnecessary for, for example, tomosynthesis image capturing in a standing position. The imaging table 2105 may include a storage portion that stores the X-ray detector 2106, and a moving mechanism configured to move the X-ray detector 2106 by moving the position of the storage portion. Note that the moving mechanism is unnecessary for, for example, tomosynthesis image capturing without moving the X-ray detector.

Figure 22:
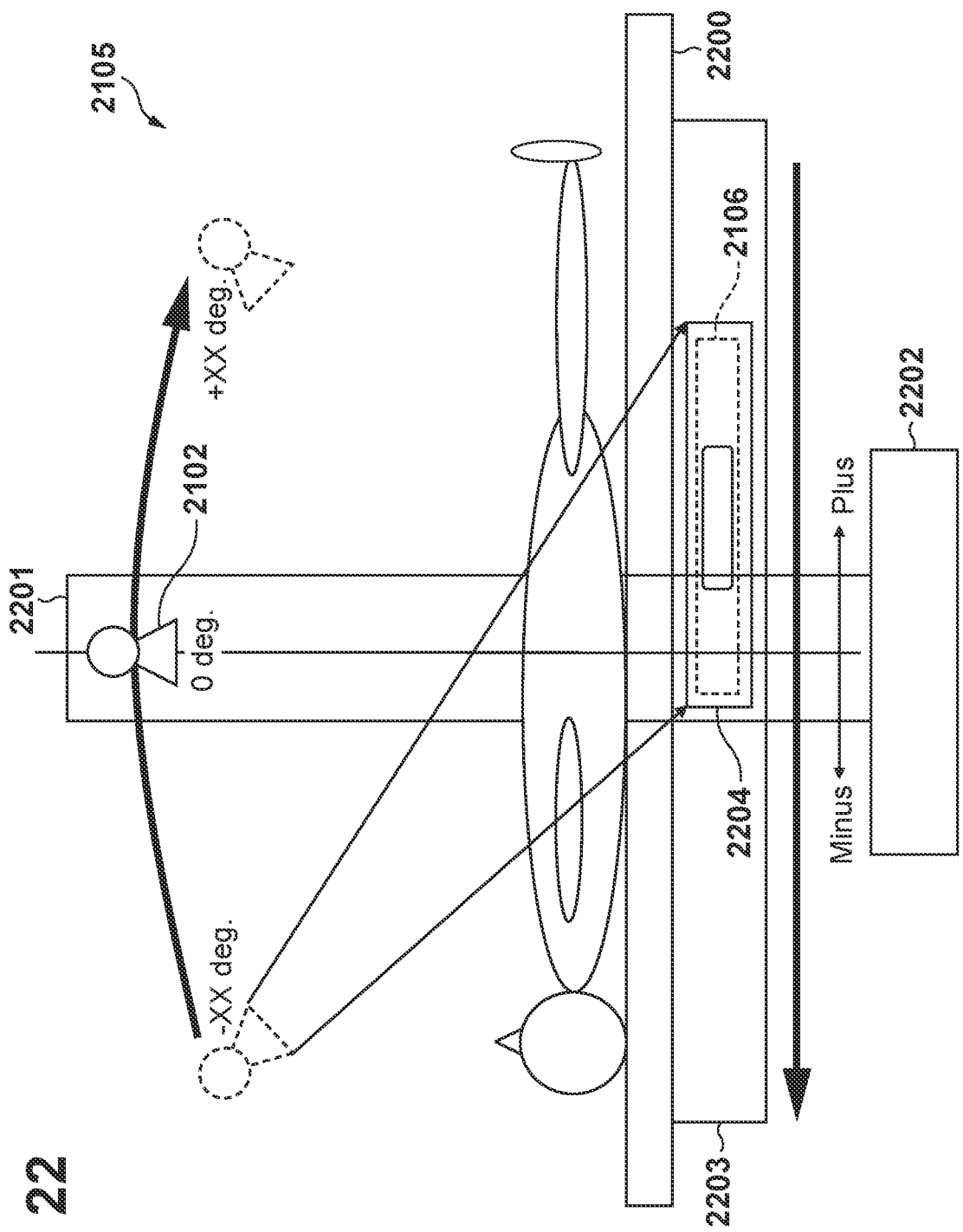
FIG. 22 is a view showing a system arrangement at the time of tomosynthesis image capturing according to the embodiment of the present invention.

An example of the arrangement of the imaging table used in tomosynthesis image capturing will be described with reference to FIG. 22. The imaging table 2105 includes a top plate 2200 that holds a subject, a column 2201 that holds the X-ray generation apparatus 2102, a base 2202 of the column 2201, a first moving mechanism that moves the X-ray generation apparatus 2102, and the moving mechanism control unit 21051 that controls the moving mechanism. The column 2201 can tilt with respect to the base 2202. The X-ray generation apparatus 2102 is fixed to the column 2201. When collecting projected image data in tomosynthesis image capturing, the X-ray generation apparatus 2102 moves in the longitudinal direction of the top plate 2200 with respect to a position as the center, where the base 2202 and the column 2201 are perpendicular to each other before the start of irradiation.

In addition, the imaging table 2105 may include a holding portion 2204 that holds the X-ray detector 2106, a guide portion 2203 of the holding portion 2204, and a second moving mechanism that moves the X-ray detector. In this case, the holding portion 2204 moves along the guide portion 2203 by a preset distance in the longitudinal direction of the top plate reverse to the X-ray generation apparatus 2102. In this way, when irradiation starts, projected image data as the base of reconstruction processing are collected, and position information is acquired while moving the X-ray generation apparatus 2102 and the X-ray detector 2106 in opposite directions.

Note that the X-ray detector 2106 makes a linear orbit, and the X-ray generation apparatus 2102 makes an arc orbit. However, the X-ray generation apparatus 2102 may also be moved to make a linear orbit. In this case, the X-ray generation apparatus 2102 may be moved in a direction perpendicular to the longitudinal direction of the column 2201 while appropriately changing the position of the X-ray generation apparatus 2102 with respect to the longitudinal direction of the column 2201.

The first and second moving mechanisms that move the column 2201 and the holding portion 2204 of the X-ray detector 2106 are controlled by the moving mechanism control unit 21051. According to input control parameters, the moving mechanism control unit 21051 moves the X-ray generation apparatus 2102 and the X-ray detector 2106 so as to arrange them in predetermined positions at predetermined speeds and timings.

The angle of the top plate 2200 of the imaging table 2105 with respect to the direction of gravity may be changeable. When performing imaging in a standing position, the top plate 2200 is tilted in the direction of gravity, and functions as a holding portion that holds a subject.

The imaging table used for tomosynthesis image capturing may take another embodiment that enables movement of the X-ray generation apparatus 2102.

Figure 23:
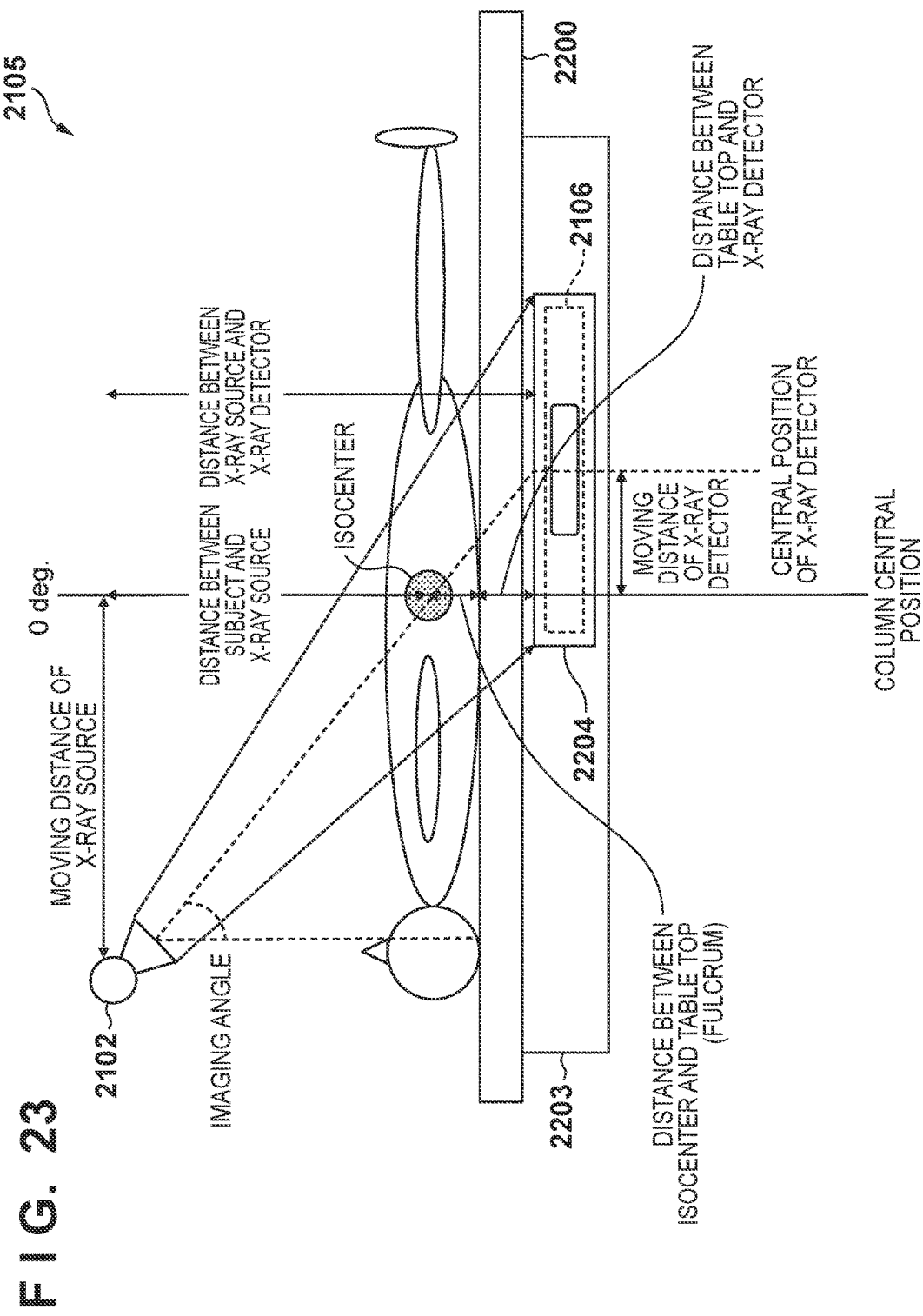
FIG. 23 is a view showing position information acquired at the time of tomosynthesis image capturing.

FIG. 23 explains information representing the geometry of tomosynthesis image capturing. This information is acquired when, for example, collecting projected image data and transmitted from the above-described moving control unit to the imaging control apparatus 2107.

The isocenter is a position as the center of tomosynthesis image capturing. The isocenter is preferably determined before imaging so as to pass through a region of interest of a subject because a coronal image passing through the isocenter normally attains the highest image quality, although depending on the reconstruction method. The X-ray generation apparatus 2102 and the X-ray detector 2106 move such that the center (detector central position) between the X-ray focus of the X-ray generation apparatus 2102 and the detection plane of the X-ray detector 2106 always passes through the isocenter. The isocenter is set by, for example, the distance (the fulcrum or the distance between the isocenter and the table top) from the upper surface of the top plate of the imaging table.

The imaging angle or projection angle is an angle made by a line that connects the isocenter and the X-ray generation apparatus 2102 and the normal to the detection plane of the X-ray detector 2106. This angle is a parameter associated with image quality, and is therefore determined before imaging.

Another parameter that affects the geometry of tomosynthesis image capturing is an imaging region or reconstruction region. Concerning a direction parallel to the detection plane, the region is determined by a collimated light irradiation region in a case in which the X-ray generation apparatus 2102 is located at the column central position. Concerning a direction perpendicular to the detection plane, the region may be determined by a height from the isocenter or a height from the table top. Alternatively, the display unit 2109 may be caused to display a schematic depiction of the subject placed on the table, and a three-dimensional region of the subject may be designated to determine the reconstruction region. Note that FIG. 23 assumes that the front surface of the X-ray detector 2106 is irradiated with X-rays. However, the present invention is not limited to this, and the imaging region may be limited in accordance with the imaging target region.

The range of the X-ray source moving distance and the range of the detector moving distance are determined based on the thus determined isocenter, imaging angle (projection angle), and reconstruction region. The distance between the table top and the X-ray detector is determined in advance but may be changeable. These pieces of information are, for example, determined by the imaging control apparatus 2107 or input to the imaging control apparatus 2107 via the operation unit 2108 and held.

The number of projected images to be captured is determined in advance before imaging. Accordingly, the moving amounts of the X-ray generation apparatus 2102 and the X-ray detector 2106 per cycle of imaging are determined. The irradiation interval of the X-ray generation apparatus 2102 is thus determined.

The imaging angle, the X-ray source moving distance, and the X-ray detector moving distance change upon capturing each projected image. When the X-ray generation apparatus 2102 makes a curved orbit, the distance between the subject and the X-ray source and the distance between the detector and the X-ray source change as well. The moving mechanism control unit 21051 records these parameters at the timing of imaging each projected image, that is, in every X-ray irradiation, and transmits them to the imaging control apparatus 2107 as geometric information corresponding to each projected image.

Note that FIG. 23 shows, as the moving method of the X-ray generation apparatus 2102, an example in which the column 2201 tilts at the contact with respect to the base 2202. However, the column 2201 may make a horizontal displacement.

An example of the arrangement of the control unit 2111 of the X-ray imaging system 2101 according to the embodiment will be described with reference to FIG. 24.

The control unit 2111 includes an imaging technique list storage unit 2402, a test storage unit 2403, an imaging control unit 2405, a test control unit 2406, an input detection unit 2407, an image output control unit 2408, and a display control unit 2409. The communication circuit 2112, the image processing unit 2110, the operation unit 2108, and the display unit 2109 are connected to the control unit 2111.

The imaging technique list storage unit 2402 stores, updates, deletes, and searches for imaging technique information. The imaging technique information here includes all items settable for each imaging technique from imaging execution to post-processing and image output setting. The imaging technique information includes, for example, information used to specify an imaging technique such as an imaging part and an imaging direction, default imaging conditions, default image processing parameters, default reconstruction parameters, storage transfer settings, print output settings, and the like.

The imaging technique list storage unit 2402 is formed from a database. The test storage unit 2403 registers, updates, deletes, and searches for test information of test information. The test storage unit 2403 is formed from a database.

The test control unit 2406 generally controls the progress of an entire test of a subject including at least one unit of tomosynthesis image capturing. For example, according to data reception or an operation input, the test control unit 2406 performs control of the whole procedure of test execution such as updating/registration control of subject information, execution-scheduled test information, and imaging technique information, screen transition control, tomosynthesis image data storage, and tomosynthesis image addition processing.

The imaging control unit 2405 performs control to execute one unit of tomosynthesis image capturing. The imaging control unit 2405 transmits/receives imaging enable/disable information, imaging execution conditions, and geometry data to/from the X-ray generation apparatus 2102 and the X-ray detector 2106 via the communication circuit 2112. The imaging control unit 2405 also performs control concerning reconstruction processing execution and control of one X-ray imaging procedure such as X-ray image data storage and the whole procedure of reconstruction processing execution.

The input detection unit 2407 detects the information of an operation input from the operation unit 2108 and inputs it to a control unit such as the imaging control unit 2405, the test control unit 2406, the image output control unit 2408, or the display control unit 2409. The display control unit 2409 performs output control to the display unit 2109 based on a screen transition specification notified from each control unit from the test control unit 2406 or the information of an operation input from the input detection unit 2407.

The image output control unit 2408 determines whether output of an image included in received test information is possible, and specifies image output to the communication circuit 2112.

The imaging control unit 2405 selects a reconstruction method. As the reconstruction method, at least one method is selected for one unit of tomosynthesis image capturing. Reconstruction methods as selection candidates include the first reconstruction method of reconstructing three-dimensional voxel data and the second reconstruction method of directly reconstructing two-dimensional tomographic images. For example, according to an operation input from the operation unit 2108, the imaging control unit 2405 selects a reconstruction method according to a situation and causes the image processing unit 2110 to execute reconstruction by the selected reconstruction method.

In one embodiment, the control unit 2111 further includes a 3D determination unit 2401 that determines whether the size of three-dimensional volume data determined by the three-dimensional volume data reconstruction conditions when reconstructing the image processing unit 2110 exceeds a threshold.

For example, using a projected image size and a three-dimensional texture limiting value notified from the imaging control unit 2405, the 3D determination unit 2401 determines whether a two-dimensional tomographic image parallel to the detection plane of the X-ray detector 2102 at the isocenter exceeds the three-dimensional texture limiting value when three-dimensional volume data of the same size as the projected image size is generated. Note that in tomosynthesis image capturing, the projection angle is limited. Hence, in this embodiment, a region through which all X-ray beams from the respective projection angles pass is defined as the maximum region of the reconstruction region. Reconstruction processing is actually performed for a part or entire region to reconstruct three-dimensional volume data. The maximum region of the reconstruction region has an octahedral shape in which a plane parallel to the detection plane is always rectangular and decreases its area as the plane moves away from the isocenter in the vertical direction. As the size information of the projected image, any of the information of the imaging condition of the projected image and the information of the projected image captured by the X-ray detector 2106 and received by the control unit 2111 via the communication circuit 2112 can be used. The 3D determination unit 2401 can use a more appropriate value for determination by calculating the size from the set imaging condition when executing determination processing before imaging or by using an acquired X-ray image data size when executing determination processing after imaging. The three-dimensional texture limiting value is a value determined by a processing module included in the image processing unit 2111, and is, for example, 2048×2048×2048 pixels. If one of the values in the X, Y, and Z directions out of the sizes of the three-dimensional volume data exceeds the limiting value, it is determined that the size of the three-dimensional volume data exceeds the threshold. Note that in a tomosynthesis image, the resolution in the direction perpendicular to the top plate 2200 is not so high as compared to the resolution in the direction parallel to the top plate 2200. Hence, when a projected image that determines the resolution in the direction parallel to the top plate 2200 is used for determination, sufficiently appropriate determination can be done.

Additionally, if the size of the three-dimensional volume data is defined irrespective of the projected image size, the size of the three-dimensional volume data and the three-dimensional texture limiting value are directly compared.

Based on the above-described determination, the imaging control unit 2405 switches between the first reconstruction method and the second reconstruction method based on whether the size of three-dimensional volume data determined by the reconstruction conditions of three-dimensional volume data exceeds the threshold. With this processing, the image processing unit 2110 generates an oblique cross-sectional image under generation conditions based on information about the data size of three-dimensional volume data determined by the reconstruction conditions of three-dimensional volume data. In one embodiment, if the data size of three-dimensional volume data determined by the reconstruction conditions does not exceed the threshold, the image processing unit 2110 generates an oblique cross-sectional image based on three-dimensional volume data constituted by a plurality of voxel data. If the data size exceeds the threshold, the image processing unit 2110 generates an oblique cross-sectional image based on a plurality of two-dimensional cross-sectional images. Accordingly, when oblique cross-sectional image generation is performed in a state in which a plurality of coronal images are reconstructed, an oblique cross-sectional image is generated based on the plurality of coronal images. This makes it possible to generate an oblique cross-sectional image at a high speed even without three-dimensional volume data.

In one embodiment, the imaging control unit 2405 further selects a method to be used out of a first generation method of generating an oblique cross-sectional image based on the three-dimensional volume data constituted by a plurality of voxel data, a second generation method of generating an oblique cross-sectional image based on a plurality of two-dimensional tomographic images, and a third generation method of generating an oblique cross-sectional image by reconstructing it based on a plurality of projected images. The first generation method is a generation method selected when the first reconstruction method is executed. This method can generate an oblique cross-sectional image from three-dimensional volume data at a high speed using a GPU.

The second generation method and the third generation method are generation methods selected when the second reconstruction method is used. In the second generation method, for example, in a state in which a plurality of coronal images are reconstructed, the plurality of coronal images are interpolated, thereby generating an oblique image. There is an advantage of high-speed processing. If the pitch between the plurality of coronal images is sufficiently small, an accurate oblique image can be generated.

In the third generation method, a desired oblique image is generated by reconstructing it from a plurality of projected images. As compared to the first and second generation methods, a high-quality oblique image can be generated. When reconstructing using the third generation method, an oblique section is designated by an operation input or the like. According to this designation, the imaging control unit 2405 extracts an X-ray beam contributing to the oblique section, that is, an X-ray beam that passes through the oblique section. The imaging control unit 2405 then causes the image processing unit 2110 to perform reconstruction processing using only projected images including the image region corresponding to the contributing X-ray beam. This can generate an oblique image at a high speed as compared to a case in which three-dimensional volume data is reconstructed. Which one of the second and third generation methods is to be used may be determined in advance as, for example, a setting for each imaging technique before a plurality of projected images are obtained or before reconstruction processing is performed. Alternatively, in reconstruction processing, the display control unit 2409 may cause the display unit 2109 to display a plurality of icons used to select a generation method, and the imaging control unit 2405 may select an icon in accordance with an operation force of the user. Otherwise, the display unit 2109 may be caused to display a plurality of icons used to select the first to third generation methods, and the imaging control unit 2405 may select an icon in accordance with an operation force of the user. This enables generation of an oblique image using a method desired by the user.

At least one of the number and the pitch angle of oblique images to be generated by the third generation method is made smaller than at least one of the number and the pitch angle of oblique images to be generated based on three-dimensional volume data. Theoretically, an infinite number of oblique cross-sectional images can be generated from three-dimensional volume data. However, the number or pitch angle of oblique sections that can be designated is limited on the user interface displayed on the display unit 2109 by the display control unit 2409. When generating oblique cross-sectional images by the third generation method, the number or pitch angle of oblique cross-sectional images is limited still further. That is, the number is made smaller, and the pitch angle is made larger. This can shorten the oblique cross-sectional image generation time. In a case in which an oblique cross-sectional image is sequentially reconstructed every time the display target oblique cross-sectional image is changed on the user interface, if the pitch angle is small, almost the same cross-sectional image is generated in every operation, and the time required to obtain an overview of the tendency becomes too long. When the pitch angle is made large, an overview of the tendency can easily be obtained.

In one embodiment, the control unit 2111 further includes an oblique determination unit 2404 that determines whether to limit display of an oblique image. The oblique determination unit 2404 determines a limiting method for oblique section display using a three-dimensional texture limitation determination result notified from the 3D determination unit 2401 via the X-ray control unit 2104 and an oblique section display limitation setting included in imaging technique information. Various methods are considerable as the limiting method. An example of the limiting method is a method of reducing a data size. In this case, if the size of three-dimensional volume data determined by the reconstruction conditions exceeds the threshold, the image processing unit 2110 reconstructs three-dimensional volume data of a data size smaller than the size. The data size of a generated oblique image is thus limited. By the above-described processing, if the data size of three-dimensional volume data determined by the reconstruction conditions exceeds the threshold as the result of determination by the three-dimensional texture determination unit 2401, the display control unit 2409 causes the display unit to display an oblique image smaller than the data size determined by the reconstruction conditions of the three-dimensional volume data. This enables high-speed oblique cross-sectional image generation based on three-dimensional volume data even under a size limitation.

As the method of reducing the size of three-dimensional volume data, the image processing unit 2110 reduces the size of a region determined by three-dimensional volume data as three-dimensional volume data of a small data size. There also exist a method of reconstructing three-dimensional volume data in which at least one of the number of voxels is made smaller by addition or the like without changing the region itself and a method of generating volume data of a small data size using both region reduction and addition processing. This makes it possible to obtain three-dimensional volume data and generate an arbitrary oblique section at a high speed, although the region or resolution lowers. With this processing, the display control unit 2409 causes the display unit to display, as an oblique image of a data size smaller than the data size determined by the reconstruction conditions, an oblique image for which at least one of the size of a region represented by the oblique image determined by the reconstruction conditions and the number of pixels of the oblique image is small. If the region is narrowed, a high-quality oblique image as in a case in which a size limitation is not imposed in the region can be displayed at a high speed. For example, if the number of pixels is reduced without narrowing the region, an oblique image representing the same region as in a case in which a size limitation is not imposed can be displayed at a high speed. If both the region and the pixel values are reduced, an oblique cross-sectional image can be displayed at a higher speed.

If the size of three-dimensional volume data exceeds the threshold, to reduce the size of the three-dimensional volume data, the image processing unit 2110 generates the three-dimensional volume data using a plurality of reduced projected images obtained by reducing the data size of the plurality of projected images. This can reduce the data size of the processing target and speed up reconstruction processing.

In addition, if the size exceeds the threshold, the display control unit 2409 can limit display of an oblique cross-sectional image.

Figure 25:
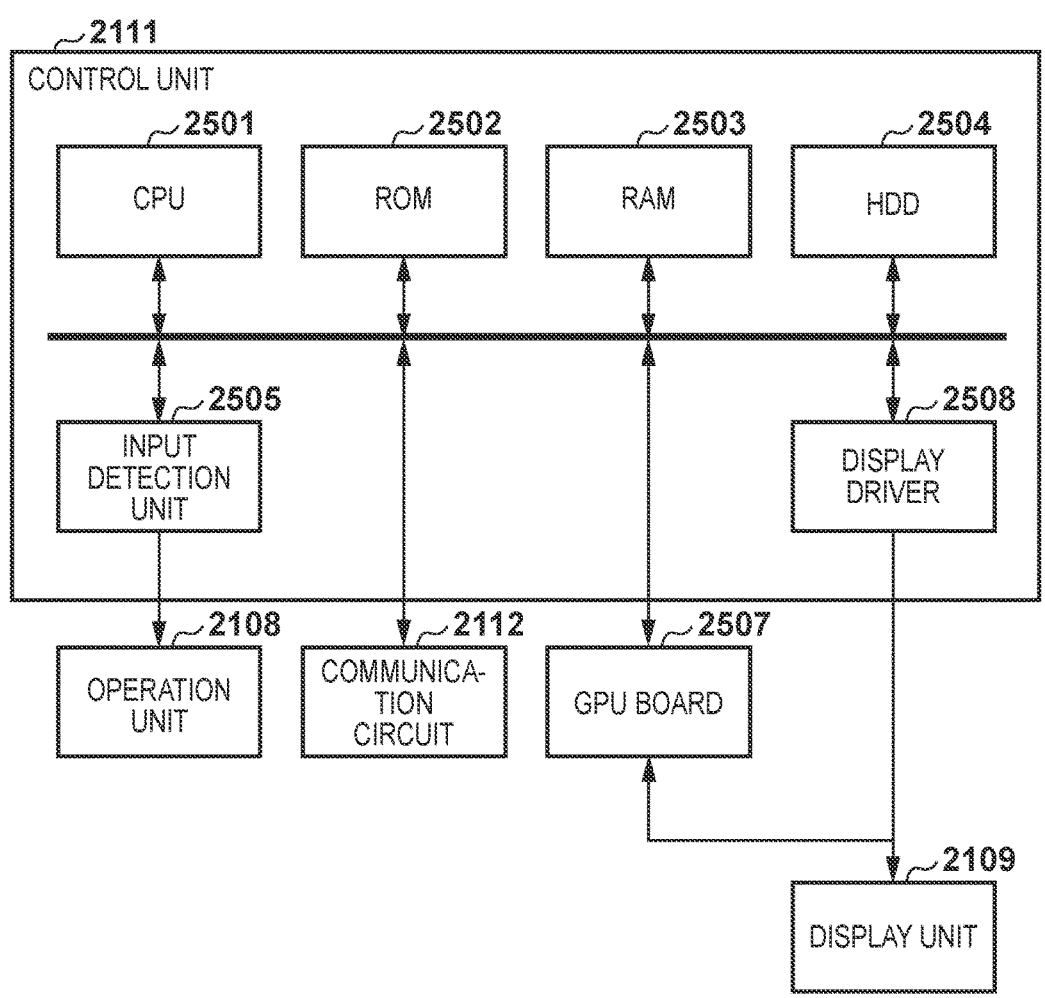
FIG. 25 is a view showing the hardware arrangement of the imaging control unit according to the embodiment of the present invention.

An example of the hardware arrangement of the control unit 2111 according to the embodiment of the present invention will be described with reference to FIG. 25. The control unit 2111 includes a CPU 2501, a ROM 2502, a RAM 2503, an HDD 2504, an input detection unit 2505, and a display driver 2508. The control unit 2111 is connected to the communication circuit 2112 and a GPU board 2507. The GPU board 2507 may be connected to the display unit 2109. These units are connected to each other via a bus such as a data bus. The CPU 2501 controls the entire control unit 2111 and executes a program stored in the ROM 2502, thereby implementing the functions of the units of the control unit 2111 shown in FIG. 25 and implementing control shown in the flowcharts of FIGS. 27A, 27B, 29, 32A, 32B, and 35 (to be described later). The CPU 2501 also performs input/output control to the display unit 2109 via the display driver 2508 and input/output control to the operation unit 2108 via the input detection unit 2505. The RAM 2503 allocates a storage area for an operation when the CPU 2501 controls based on an instruction program. The HDD 2504 is an auxiliary storage device that stores various kinds of data such as X-ray image data. The communication circuit 2112 is a communication interface and performs data transmission/reception between the control unit 2111 and the X-ray control unit 2104, the X-ray detector 2106, and the network 2113.

The display driver 2508 is software configured to control the display unit 2109 from the control unit 2111. When display image data is output from the GPU board 2507 to the display unit 2109, the GPU board 2507 provides the function of the display driver 2508.

The GPU board 2507 is a general-purpose graphics board including a GPU and a video memory. The GPU board 2507 constitutes the image processing unit 2110 and performs reconstruction processing and image processing of tomographic images.

Figure 26A:
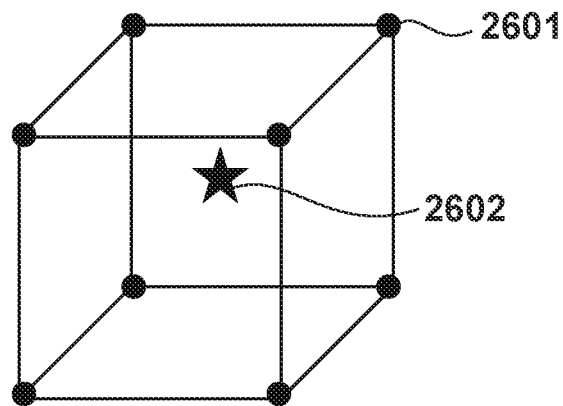
FIGS. 26A and 26B are views showing interpolation of peripheral pixels at an arbitrary coordinate point and an arbitrary cross section on three-dimensional voxel data.
Figure 26B:
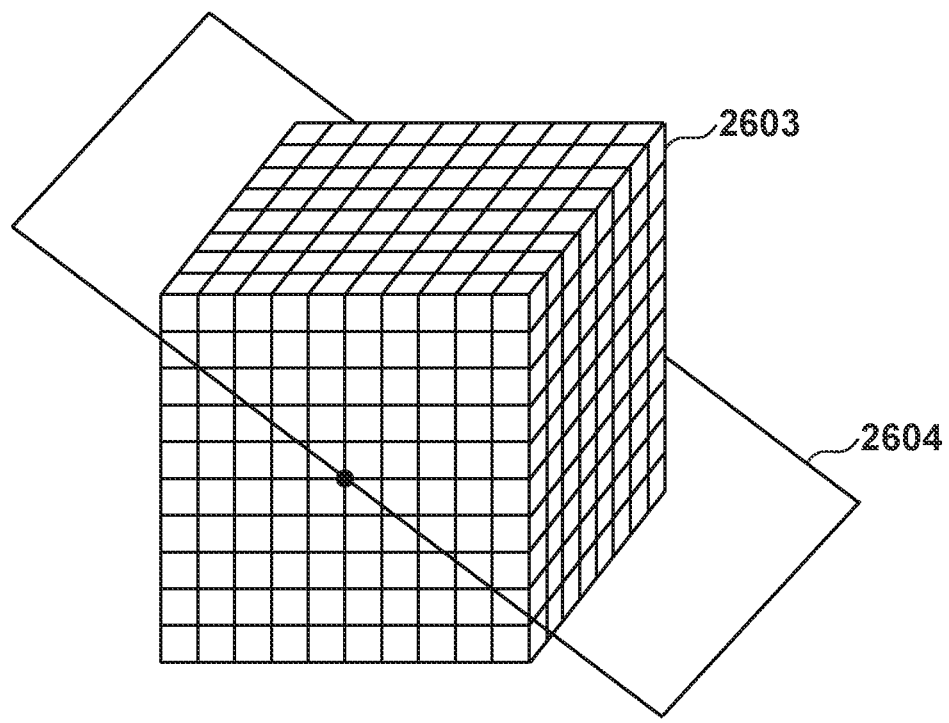

The GPU board 2507 manages a three-dimensional image on the video memory as three-dimensional voxel data called a three-dimensional texture. When the GPU board 2507 manages an image on the video memory as three-dimensional voxel data, as shown in FIG. 26A, the GPU board 2507 can acquire the pixel value of a pixel at arbitrary coordinates 2602 by interpolating the pixel values of eight peripheral pixels 2601. Hence, when an arbitrary position and angle are designated for image data 2603 managed as three-dimensional voxel data, as shown in FIG. 26B, an arbitrary oblique section 2604 can be displayed. When such an arithmetic unit is used, an operation such as reconstruction processing and image display can be done at a high speed without using dedicated hardware.

Figure 27A:
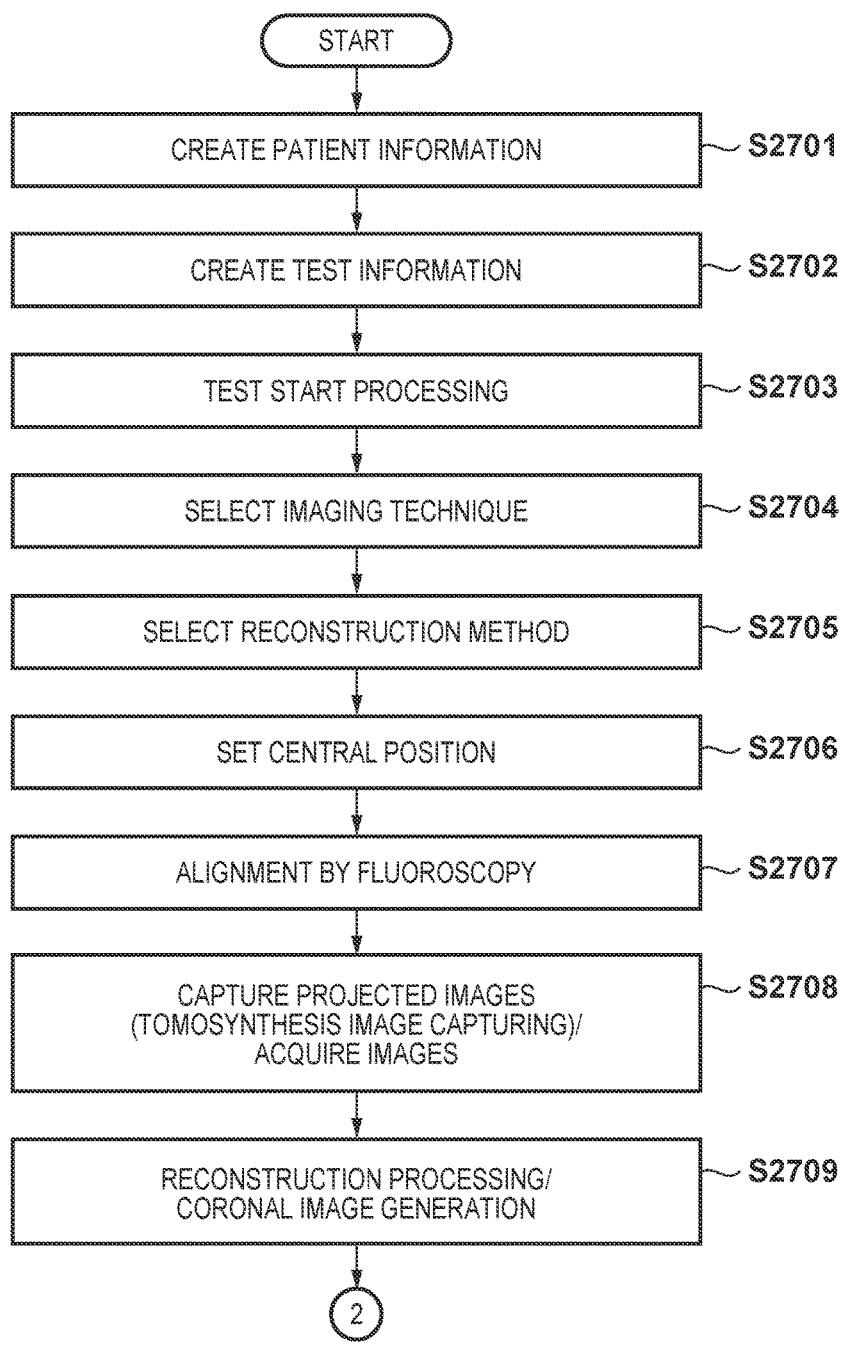
FIGS. 27A and 27B are flowcharts showing the procedure of processing from the start to the end of a test at the time of tomosynthesis image capturing according to the embodiment of the present invention.
Figure 27B:
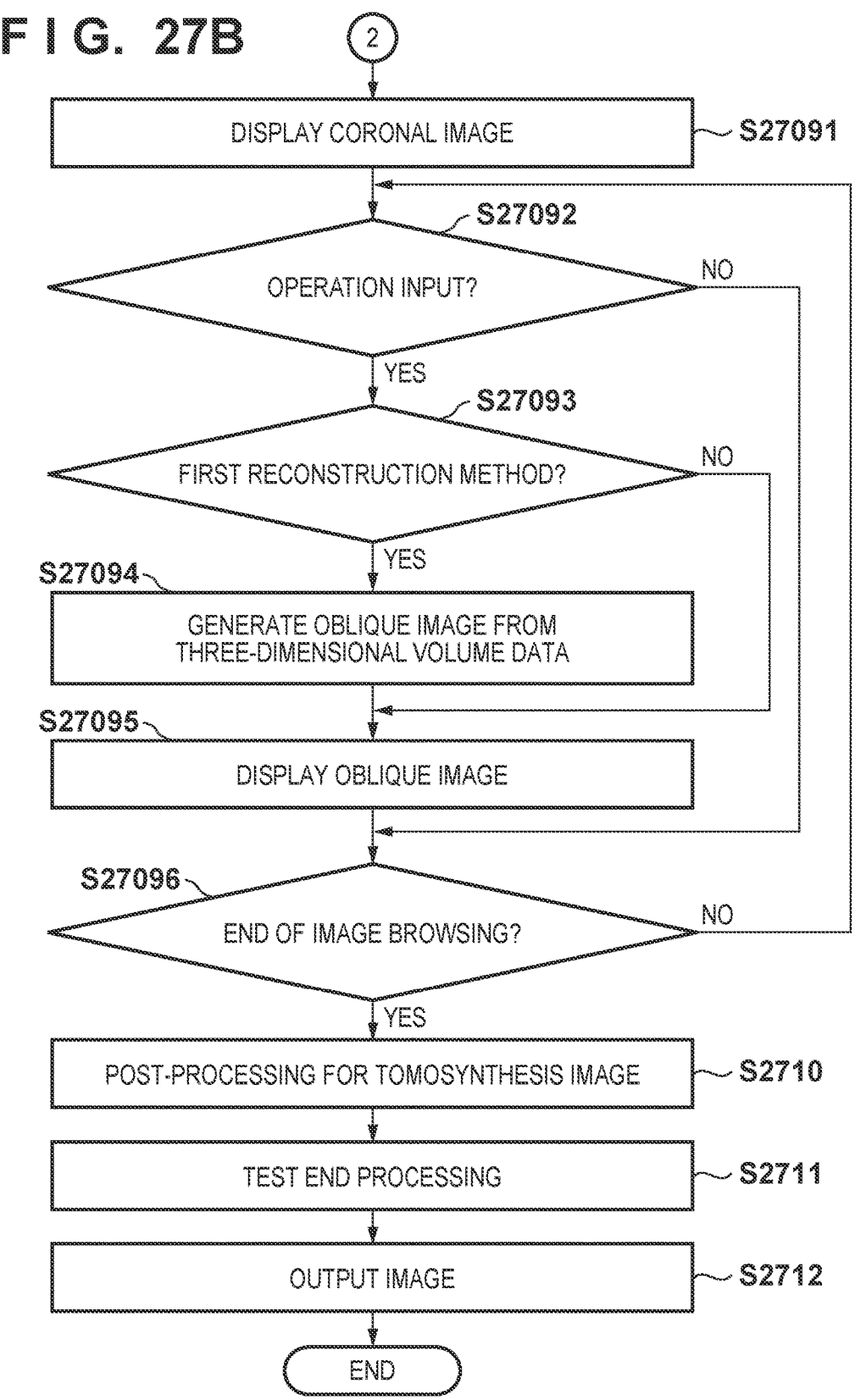

An example of the procedure from the start to the end of tomosynthesis image capturing according to the embodiment of the present invention will be described next with reference to the flowcharts of FIGS. 27A and 27B.

In step S2701, the identification information of a subject is created before the start of a test. The identification information of the subject here includes at least the information of a subject ID, and may additionally include information to specify the subject such as a subject name, age, date of birth, gender, height, weight, and pregnancy state. In step S2701, the display control unit 2409 displays a subject information input screen. When an operation input to determine the identification information of the subject is done on the operation unit 2108, the input detection unit 2407 outputs a signal that notifies that the identification information of the subject is determined. Upon receiving the notification signal, the test control unit 2406 newly generates execution-scheduled test information. The execution-scheduled test information here includes the above-described identification information of the subject, test identification information including identification information to specify a test such as a test ID and a test date/time, and imaging technique information including information to specify an imaging technique such as an imaging part. The test control unit 2406 inputs the identification information of the subject included in the signal that notifies that the subject information is determined to the execution-scheduled test information. After that, the test control unit 2406 transmits a notification to request all registered imaging techniques to the imaging technique list storage unit 2402. Upon receiving the notification, the imaging technique list storage unit 2402 acquires all pieces of registered imaging technique information and transmits them to the test control unit 2406. Upon receiving the imaging technique information, the test control unit 2406 transmits, to the display control unit 2409, a signal that notifies that a transition to an imaging technique selection screen should be made and image data representing the imaging technique selection screen together with the imaging technique information. Upon receiving the signal that notifies that a transition should be made, the display control unit 2409 causes the display unit 2109 to display the imaging technique selection screen. The display unit 2109 displays the received imaging technique information on the imaging technique selection screen.

Next, in step S2702, test information is created. Test information creation processing here includes processing of selecting an imaging technique to be executed. When the input detection unit 2407 detects an operation input to select an imaging technique, the test control unit 2406 holds the information of the selected imaging technique. Upon detecting an operation input to specify the start of a test, the input detection unit 2407 transmits, to the test control unit 2406, a signal that notifies that the test information and test information including the selected execution-scheduled imaging techniques are determined. Upon receiving the signal that notifies that the test information is determined, the test control unit 2406 stores the imaging techniques held as the selected imaging techniques, the already determined subject identification information, and the test identification information in the test storage unit 2403 in association with each other as test information.

Note that in steps S2701 and S2702 described above, the subject information, the test identification information, and the execution-scheduled imaging techniques are manually created. In another embodiment, the communication circuit 2112 receives work list information including at least one piece of test information from the HIS/RIS 2114. According to an operation input of the user to select the test information included in the work list information, the test control unit 2406 stores the subject information, the test identification information, and the imaging techniques included in the selected test information in the test storage unit 2403.

Next, in step S2703, test start processing is executed. When creation of the test execution information ends in step S2702, the test control unit 2406 transmits a test start notification to the test storage unit 2403 and the display control unit 2409. To the display control unit 2409, together with the test start notification, image data representing an imaging screen 2801 used to display test information stored in the test information storage unit and execute imaging is transmitted to the display control unit 2409. Upon receiving the test start notification, the test storage unit 2403 newly registers the execution-scheduled test information as test information. The test storage unit 2403 updates the test status of the newly registered test information to "execution underway". Test statuses include "yet to be started", "execution underway", "suspended", and "ended". Upon receiving the test start notification and the image data representing the imaging screen 2801, the display control unit 2409 causes the display unit 2109 to display the image data representing the imaging screen 2801. The display unit 2109 displays the subject information, the test information, and the imaging technique information included in the received test information on the imaging screen 2801.

In step S2704, an imaging technique to execute imaging next is designated out of the execution-scheduled imaging techniques included in the started test information. The imaging technique is designated by the test control unit 2406 in accordance with the pressing of at least one imaging technique region 2809 displayed on the imaging screen 2801. If the imaging technique is an imaging technique corresponding to tomosynthesis, the test control unit 2406 designates a tomosynthesis imaging technique and designates imaging conditions included in the imaging technique. The information of a tomosynthesis imaging technique includes reconstruction conditions based on projected images, image processing conditions after that, and output conditions as well as the imaging conditions of (projected images of) tomosynthesis image capturing including the imaging conditions of the X-ray detector 2106 and the irradiation condition of the X-ray generation apparatus 2102.

The reconstruction conditions include conditions such as a reconstruction method of determining whether to reconstruct three-dimensional volume data or two-dimensional tomographic images, a reconstruction algorithm, a reconstruction filter, and the degree of noise reduction processing. As the reconstruction algorithm here, algorithms such as filter back projection, shift-and-add method, and successive approximation reconstruction are used.

Upon detecting that the operation unit 2108 has accepted the pressing of the imaging technique region 2809, the input detection unit 2407 transmits a signal that notifies that the imaging technique is designated and information used to specify the designated imaging technique to the test control unit 2406. According to the designation of the imaging technique, the imaging control unit 2405 controls tomosynthesis image capturing based on the imaging conditions included in the designated imaging technique. The imaging control unit 2405 transmits imaging conditions corresponding to the designated imaging technique to the X-ray detector 2106 via the communication circuit 2112. The imaging conditions include the information of, for example, an accumulation time, a read range corresponding to an irradiation range, and a frame rate. Accordingly, the imaging conditions are set in the X-ray detector 2106. According to transmission of the imaging conditions and according signal transmitted together with the imaging conditions, the X-ray detector 2106 starts power supply to the sensor array and periodical output processing of dark current data.

The imaging control unit 2405 notifies the X-ray control unit 2104 of the information of irradiation conditions corresponding to the designated imaging technique via the communication circuit 2112. The X-ray control unit 2104 sets the irradiation conditions.

Note that according to the designation of the imaging technique, the imaging control unit 2405 may transmit a predetermined signal to the moving mechanism control unit 21051 as well. The moving mechanism control unit 21051 moves the X-ray generation apparatus 2102 and the X-ray detector 2106 to reference positions in accordance with the reception of the signal. The reference position is a position at which, for example, the imaging angle (projection angle) is 0°.

The display control unit 2409 also cause the display unit 2109 to display that preparation for irradiation is underway. The display unit 2109 switches the display of a status region 2803 on the imaging screen 2801. The imaging control unit 2405 performs the display switching upon receiving, via the communication circuit 2112, a notification representing that imaging condition setting in the X-ray detector 2106 and the X-ray control unit 2104 is completed. Alternatively, the display switching may be done upon receiving, from the moving mechanism control unit 21051, a notification representing that the X-ray generation apparatus 2102 and the X-ray detector 2106 have moved to the reference positions, in addition to or in place of the notification. When the display of the status region 2803 is switched in this way, information representing the presence/absence of a setting error can be notified to the user.

In addition, the display control unit 2409 causes the display unit to display a thumbnail region 2811 that displays a captured image or a reconstructed image in the imaging technique region 2809 on the imaging screen 2801. The thumbnail region 2811 is displayed as a region enclosed in a box. When the display of the status region 2803 and the imaging technique region 2809 is switched in this way, it is possible to easily discriminate the irradiation enable state and the imaging technique to add an image in the next irradiation. Note that the procedure of manually designating an imaging technique has been described above. However, the imaging technique may automatically be designated when the next imaging preparation can be done at the start of a test or at the end of irradiation. In this case, when the next imaging preparation can be done, the test control unit 2406 acquires imaging technique information with a status "yet to be captured" out of the execution-scheduled imaging technique information included in the execution-scheduled test information. The statuses of imaging technique information include "imaging underway" and "imaging completed" in addition to "yet to be captured". The test control unit 2406 designates the imaging technique registered first in the pieces of imaging technique information of "yet to be captured". The subsequent processing is the same as described above. This saves the operator the time of manually designating the next imaging technique every time imaging is performed, and reduce the workflow. Which one of automatic designation and manual designation should be executed may be switched by a setting.

In step S2705, the imaging control unit 2405 selects a reconstruction method based on information included in the imaging technique information. In one embodiment, the information of a reconstruction method is included in the imaging technique information, and a reconstruction method according to the imaging technique is selected. This is implemented by setting reconstruction conditions executable within restrictions such as a memory limitation of the GPU while ensuring matching with other conditions such as the imaging conditions. When the information of the reconstruction method is included in the imaging technique information in advance, reconstruction under appropriate reconstruction conditions can be implemented without causing an error or the like.

If the imaging control unit 2405 has changed some or all of the conditions included in the imaging technique according to, for example, an operation input depending on the situation, that is, if a new condition is designated, the imaging control unit 2405 selects appropriate reconstruction conditions based on the newly designated condition. For example, assume that 2×2 binning is designated as an imaging condition of projected images by the X-ray detector 2106, and the imaging condition is changed not to execute the binning.

In one embodiment, three-dimensional texture limitation determination is executed at the timing of setting the imaging condition, thereby notifying the operator or limiting the imaging condition if the imaging condition set before imaging exceeds the three-dimensional texture limitation. According to redesignation of the imaging condition, the 3D determination unit 2401 determines whether the size of three-dimensional volume data exceeds the threshold of memory limitation when the three-dimensional texture limitation determination is reconstructed under the set reconstruction conditions based on projected images obtained under the imaging conditions after the change. Every time an imaging condition is changed or redesignated, matching with the reconstruction conditions is confirmed, thereby easily prompting the user to change the imaging condition.

If the imaging technique information does not include the information of a reconstruction method, the 3D determination unit 2401 may appropriately execute the determination in accordance with the designation of imaging conditions by the imaging control unit 2405.

Upon determining that the size exceeds the threshold, for example, the display control unit 2409 causes the display unit 2109 to do display to notify that a determination result representing that the size exceeds the threshold is obtained. Alternatively, the display unit 2109 is caused to display not the determination result itself but information representing that matching occurs between various conditions such as the imaging conditions and reconstruction conditions based on the determination result. Otherwise, reconstruction under the current reconstruction conditions is impossible unless the imaging condition is changed. Upon determining that the size does not exceed the threshold, a notification that matching between the conditions is ensured may be displayed. The notification based on the determination result may be prohibited. The notification need not always be done by display, and a sound or the like may be used.

In addition, for example, the imaging control unit 2405 changes at least some of the designated imaging conditions or reconstruction conditions in accordance with the determination by the 3D determination unit 2401. For example, consider a case in which an operation input to extend the reconstruction region in the direction parallel to the top plate 2200 is done. In this case, the imaging control unit 2405 changes the reconstruction region included in the reconstruction conditions. Accordingly, the 3D determination unit 2401 determines whether the data size of three-dimensional volume data determined by the reconstruction conditions exceeds the three-dimensional memory limitation of the GPU. In this case, the imaging control unit 2405 changes, for example, the reconstruction conditions and reduces the pixel pitch of the three-dimensional volume data to ½. Alternatively, the imaging control unit 2405 changes the imaging conditions to capture projected images by 2×2 binning. Otherwise, in a case in which 2×2 binning is designated, if the imaging conditions are changed not to execute binning, and the 3D determination unit 2401 determines that the size exceeds the memory limitation, the imaging control unit 2405 changes the reconstruction conditions and selects the second reconstruction method. In this way, priority is given to the imaging condition changed or redesignated by the user, and the original imaging conditions are changed, matching between the conditions can be ensured.

The imaging control unit 2405 need not always immediately change the imaging conditions or reconstruction conditions in accordance with the determination. The display control unit 2409 causes the display unit to display a candidate of an imaging condition after change derived by the imaging control unit 2405, a first icon that accepts an operation input to approve the candidate, and a second icon that accepts an operation input to reject the candidate. When the input detection unit 2407 detects an operation input to the first icon, the imaging control unit 2405 changes the condition. This can reduce a condition change undesired by the user. In addition, the display unit may be caused to display a list to input an imaging condition or reconstruction condition desired by the user, and one of the conditions may be selected by an operation input.

Furthermore, for example, when selecting an imaging technique in step S2702, the following display control may be executed. When at least some of imaging conditions or reconstruction conditions are designated by the imaging control unit 2405, the display control unit 2409 limits the range inputtable via the operation unit 2108 concerning imaging conditions or reconstruction conditions different from those designated. For example, consider a case in which the binning condition is set to 1×1, that is, a setting to prohibit binning is done, and the first reconstruction method of reconstructing three-dimensional volume data is selected. In this case, the display control unit 2409 displays a partial region of 2048×2048×2048 pixels that is the memory limiting value with respect to the isocenter as the center and regions smaller than this region as choices of reconstruction regions represented by three-dimensional volume data. As another example, consider a case in which the first reconstruction method is selected, and a cuboid region whose bottom surface is formed from a rectangle of the same size as the detection region of the detector is designated as the reconstruction region. In this case, the display control unit 2409 displays 2×2 analog binning and 3×3 digital binning as choices of the imaging conditions of projected images, but does not display a setting of 1×1 binning (binning prohibition) to prohibit selection by an operation input. This processing is attained when the 3D determination unit 2401 sequentially determines, from a candidate group, an imaging condition or reconstruction condition that matches selected or designated conditions, and outputs only matching conditions to the display control unit 2409. This makes it possible to select only matching choices and facilitate the setting of the imaging conditions or reconstruction conditions.

In the above-described example, the setting of 1×1 binning (binning prohibition) is not displayed. However, another display form may be used. For example, the display control unit 2409 can do the display corresponding to this setting in a so-called disabled state so that the setting is displayed but made unselectable by an operation input from the operation unit 2108, thereby explicitly showing the unusable choice to the user and supporting user's determination.

Alternatively, the setting of 1×1 binning (binning prohibition) is displayed and made selectable. At the same time, the display control unit 2409 may cause the display unit to display character information representing a warning upon selection and an icon to accept an operation input to select whether to approve the setting concerning the selection. Accordingly, the setting of binning prohibition is limited if the user does not approve it.

With the above processing, the reconstruction method is appropriately selected.

Subsequently, the subject is arranged. Subject arrangement is executed by the operator or a person in charge of test execution. The subject arrangement may be done almost simultaneously with steps S2701 to S2705.

In step S2706, the imaging control unit 2405 sets the isocenter that is the central position of reconstruction. Mainly the operator or the person in charge of test execution measures the central position (to be referred to as the isocenter hereinafter) based on a region of interest of the subject, and inputs the isocenter from the operation unit 2108. When the input of the isocenter is determined, the input detection unit 2407 transmits the information of the isocenter to the imaging control unit 2405 via the test control unit 2406. Upon receiving the information of the isocenter, the imaging control unit 2405 sets the received isocenter information in position information included in the selected imaging technique information.

In step S2707, the subject is aligned using X-ray fluoroscopy. Particularly in tomosynthesis image capturing, the influence of artifacts is largely concerned depending on the irradiation direction of X-rays to the subject. Hence, to confirm the arrangement of the subject, X-ray fluoroscopy is performed to confirm whether the arrangement position of the subject is correct. When the X-ray irradiation switch 2103 is pressed, the X-ray generation apparatus 2102 starts X-ray irradiation. Accordingly, the X-ray control unit 2104 transmits an irradiation start notification to the test control unit 2406 via the communication circuit 2112. Upon receiving the irradiation start notification, the test control unit 2406 updates the status of the imaging technique for which irradiation has started out of the imaging technique information included in the execution-scheduled test information to "imaging underway". The test control unit 2406 transmits the irradiation start notification to the display control unit 2409. The display control unit 2409 causes the display unit 2109 to display the status of the imaging technique, and also causes the display unit 2109 to display an X-ray moving image obtained by X-ray fluoroscopy.

Note that if the top plate 2200 of the imaging table 2105 is movable with respect to the guide portion 2203, alignment may be done by moving the top plate 2200 or by moving the column 2201 with respect to the top plate 2200. In addition, alignment in a direction perpendicular to the body axis of the subject may be done by changing the position of the X-ray generation apparatus 2102. These methods can reduce the movement of the subject and reduce the burden on the subject. Note that when one point or region in the X-ray moving image obtained by the X-ray fluoroscopy and displayed on the display unit 2109 is designated via the operation unit 2108, the imaging control unit 2405 acquires the designated position. In addition, the moving amounts of the top plate 2200, the X-ray generation apparatus 2102, and the like necessary for setting the position at the center of the imaging region are calculated and transmitted to the moving mechanism control unit 21051 as parameters. The moving mechanism control unit 21051 changes the position of the imaging system in accordance with the parameters such that the position is set at the center of the imaging region. This can facilitate alignment by designating a position in the X-ray moving image. Even the position of the isocenter S2706 in the plane direction of the top plate may be changed in accordance with designation of a position in the image obtained by the X-ray fluoroscopy by the operation unit 2108, as in the alignment of the subject.

After that, when the X-ray irradiation switch 2103 is released, the X-ray generation apparatus 2102 stops X-ray irradiation. The X-ray control unit 2104 then transmits an irradiation end notification and an imaging execution condition notification to the imaging control unit 2405 via the communication circuit 2112. Note that the imaging execution condition includes imaging execution conditions and position information. Upon receiving the irradiation end notification and the imaging execution condition notification, the imaging control unit 2405 transmits the irradiation end notification and the imaging execution condition notification to which the selected imaging technique information is added to the test control unit 2406. Upon receiving the irradiation end notification, the test control unit 2406 updates the status of an imaging technique for which irradiation has ended out of the imaging technique information included in the execution-scheduled test information to "imaging completed". Additionally, upon receiving the irradiation execution condition notification, the test control unit 2406 inputs the irradiation execution condition to an imaging technique for which irradiation has ended out of the imaging technique information included in the execution-scheduled test information. Simultaneously, the test control unit 2406 transmits the irradiation end notification and the imaging execution condition notification to the display control unit 2409. Upon receiving the irradiation end notification and the imaging execution condition notification, the display control unit 2409 switches the display of the status region 2803 on the imaging screen 2801 displayed on the display unit 2109.

Upon receiving the imaging execution condition notification, the display control unit 2409 updates a corresponding display annotation on an image region 2802. Note that the imaging execution conditions may be notified in real time during irradiation or transmitted after the end of irradiation at a timing different from the irradiation end notification. The control at the start and end of irradiation is the same in both X-ray fluoroscopy and projected image capturing.

In step S2708, tomosynthesis image capturing, that is, projected images to be used for tomosynthesis are captured. The X-ray detector 2106 acquires a plurality of projected images by imaging. The communication circuit 2112 of the control unit 2111 acquires the plurality of projected images by data reception from the X-ray detector 2106. The X-ray control unit 2104 controls X-ray irradiation. The imaging control unit 2405 controls projected image capturing by the X-ray detector 2106. The moving mechanism control unit 21051 controls the movement of the X-ray generation apparatus 2102 and the X-ray detector 2106 in synchronism with the X-ray irradiation and the projected image capturing. The imaging control unit 2405 stores, in the test storage unit 2403, the plurality of X-ray image data from the X-ray detector 2106 and position information corresponding to each X-ray image data from the moving mechanism control unit 21051.

In step S2709, the image processing unit 2110 performs reconstruction processing of tomosynthesis images. If the first reconstruction method is selected in step S2705, the image processing unit 2110 reconstructs three-dimensional volume data. If the second reconstruction method is selected in step S2705, the image processing unit 2110 reconstructs a plurality of two-dimensional tomographic images, for example, coronal images along the detection plane of the X-ray detector 2106 at different position in the direction of the thickness of the object. If the second reconstruction method is selected, oblique images may also be reconstructed. For example, if an oblique section is designated in advance, the oblique image of the cross section is reconstructed. Alternatively, for example, a plurality of oblique cross-sectional images may be reconstructed through the isocenter at a predetermined pitch.

If no reconstruction method is selected, a reconstruction method is selected based on information such as a projected image size and the reconstruction conditions, as will be described later.

The imaging control unit 2405 acquires the information of the selected reconstruction method from the test storage unit 2403, and controls processing performed by the image processing unit 2110, thereby performing reconstruction according to the reconstruction method.

The information input to the image processing unit 2110 includes, for example, imaging technique information, X-ray image data, position information, three-dimensional voxel data pixel density after reconstruction, and three-dimensional voxel data region after reconstruction.

When the imaging control unit 2405 triggers the start of reconstruction processing, the display control unit 2409 causes the display unit 2109 to display image data representing a reconstruction screen 3301 and a progress bar representing that reconstruction processing is being executed on a tomographic image region 3302. On the other hand, upon receiving a reconstruction request notification, the image processing unit 2110 executes reconstruction processing using the default reconstruction parameters of the imaging technique information, the position information, and the X-ray image data. When the reconstruction processing is completed, the image processing unit 2110 transmits a reconstruction completion notification to the imaging control unit 2405. Note that generated tomosynthesis images, the reconstruction parameters, and the image processing parameters are also transmitted together with the reconstruction completion notification.

In step S27091, the display control unit 2409, accordingly, the display control unit 2409 hides the progress bar displayed in the tomographic image region 3302. When the first reconstruction method is selected, and three-dimensional volume data is generated, the image processing unit 2110 performs coronal image generation processing based on the three-dimensional volume data. When the first reconstruction method is selected, the display control unit 2409 causes the display unit to display two-dimensional tomographic images along the detection plane of the X-ray detector 2106 which are generated based on the three-dimensional volume data.

On the other hand, when the second reconstruction method is selected, the display unit 2109 is caused to display two-dimensional tomographic images directly reconstructed from the projected images by the image processing unit 2110 in step S2709. The two-dimensional tomographic images directly reconstructed by the image processing unit 2110 include two-dimensional tomographic images along the detection planes and oblique cross-sectional images crossing the detection plane.

The above-described processing is performed appropriately in accordance with, for example, switching of the display target cross section by the operation unit 2108. Since three-dimensional volume data is reconstructed, generation and display processing can respond to an operation input to the operation unit 2108 at a high speed.

When the first reconstruction method is selected, and three-dimensional volume data is reconstructed, the display control unit 2409 specifies the image processing unit 2110 to generate a cross-sectional image in accordance with designation of a display target cross section. The image processing unit 2110 generates the two-dimensional tomographic image of the designated cross section from the three-dimensional volume data. The two-dimensional tomographic images generated here include two-dimensional tomographic images (for example, coronal images) along the detection plane of the X-ray detector 2106 and the oblique images of cross sections crossing the detection plane. As the generation method, for example, voxel interpolation processing is performed, as described with reference to FIGS. 26A and 26B.

In step S27092, the imaging control unit 2405 determines whether a specification to select an oblique image as the display target is input. As for this specification, for example, whether a specific operation input by the operation unit 2108 is done is determined. Upon determining that the specification is input (YES in step S27092), the imaging control unit 2405 determines in step S27093 whether the first reconstruction method is selected. This determination may be replaced with determining whether three-dimensional volume data is reconstructed.

Upon determining that the first reconstruction method is selected (YES in step S27093), in step S27094, the image processing unit 2110 generates an oblique image from the three-dimensional volume data based on the position of the cross section designated by the operation input. The display control unit 2409 causes the display unit 2109 to display the generated oblique image (step S27095). On the other hand, if the first reconstruction method is not selected (NO in step S27093), the display control unit 2409 causes the display unit 2109 to display an oblique cross-sectional image reconstructed by the second reconstruction method in step S2709.

Note that if the second reconstruction method is selected (NO in step S27093), but no oblique image is generated, the image processing unit 2110 may reconstruct the desired oblique cross-sectional image from projected images.

In step S27096, the imaging control unit 2405 determines whether an operation input to end image browsing is done. The determination of step S27092 is performed again until the operation input to end image browsing is done. An input to switch the display section of the coronal image of the oblique section may be accepted here.

Next, in step S2710, the image processing unit 2110 performs post-processing of the tomosynthesis images. The post-processing of the tomosynthesis images includes cutout region editing, tomosynthesis image parallel display (multi view), re-imaging processing, and a process for an image of mis-exposure.

For example, when performing tomosynthesis image capturing for another part, the process from step S2702 is repeated.

When all execution-scheduled imaging techniques are completed, and after the post-processing of the tomosynthesis images, an operation input to the operation unit 2108 is done to specify the end of the test, test end processing is executed in step S2711. The test control unit 2406 transmits a test end notification to the test storage unit 2403 and the display control unit 2409. Note that the test end notification includes the execution-scheduled test information. At the same time, the test control unit 2406 transmits an image output notification to the image output control unit 2408. Note that the image output notification includes the execution-scheduled test information. Upon receiving the test end notification, the test storage unit 2403 searches the registered test information for the execution-scheduled test information and acquires it. The test storage unit 2403 updates the test status of the acquired test information to "ended". Upon receiving the test end notification, the display control unit 2409 makes a transition to a subject information input screen. Note that even when the operation unit 2108 accepts an operation input to suspend the test, the same procedure as when ending the test is performed. In this case, however, the test storage unit 2403 updates the test status of the acquired test information to "suspended".

Next, in step S2712, image output is executed. Upon receiving the image output notification, the image output control unit 2408 executes image output to an output device 2409 via the communication circuit 2112.

An example of the imaging screen 2801 displayed in step S2703 of FIG. 27A will be described next with reference to FIG. 28. The imaging screen 2801 is formed from the image region 2802, the status region 2803, a single view icon 2804, a multi view icon 2805, a frame view icon 2806, a subject information region 2807, a test information region 2808, the imaging technique region 2809, a reconstruction icon 2810, the thumbnail region 2811, a WL input region 2812, a WW input region 2813, a suspend icon 2814, an output icon 2815, an end icon 2816, an annotation icon 2817, a right rotation icon 2818, a left rotation icon 2819, a lateral inversion icon 2820, a vertical inversion icon 2821, a black/white inversion icon 2822, an L mark icon 2823, an R mark icon 2824, a cutout icon 2825, a mask icon 2826, a re-image icon 2827, a mis-exposure image process icon 2828, an undo icon 2829, and a reset specifying portion 2830. The image region 2802 preview-displays a captured image after still image capturing or a tomosynthesis image after reconstruction processing. During moving image capturing, a captured image is preview-displayed in real time. If preview selection is switched after imaging, a captured image selected for preview is preview-displayed. Additionally, subject information, test information, irradiation conditions, and the like are displayed as annotations based in settings. In the initial state immediately after the start of a test, no image is displayed. The status region 2803 is a region that displays a status notified from the X-ray control unit 2104 or the X-ray detector 2106 using a different color or characters so as to allow the operator to easily discriminate it. The imaging control unit 2405 that has received a status notification for the X-ray control unit 2104 or the X-ray detector 2106 via the communication circuit 2414 notifies the test control unit 2406 of a status change. The test control unit 2406 determines the display contents by the combination of the statuses of the X-ray control unit 2104 and the X-ray detector 2106, and transmits a status display switching specification to the display control unit 2409. For example, if the X-ray control unit 2104 cannot perform X-ray irradiation, or the X-ray detector 2106 cannot perform X-ray detection, "Not Ready" is displayed on the sensor status. If the X-ray control unit 2104 can perform X-ray irradiation, or the X-ray detector 2106 can perform X-ray detection, "Ready" is displayed on the sensor status, and the background color is changed to a color that can easily be discriminated from that in the display of "Not Ready". The single view icon 2804 is a button used for switching to single view that displays one frame of the image selected for preview in the image region 2802. In a case of images of a plurality of frames, another frame can be displayed by operating the keyboard or mouse during preview display, and moving image reproduction is also possible. The multi view icon 2805 is a button used for switching to multi view that divides the image region 2802 into a plurality of display regions in a matrix and in parallel displays images captured in a test under execution. Until two or more images are captured in a test under execution, the button is disabled, and multi view is impossible. The frame view icon 2806 is a button used for switching to frame view that divides the image region 2802 into a plurality of display regions in a matrix and in parallel displays the frame images of a moving image selected for preview. If the image selected for preview is not a moving image, the button is disabled, and frame view is impossible. The subject information region 2807 is a region where subject information such as a subject name and a subject ID is displayed. In the test information region 2808, test information such as a test ID and a test description is displayed. Imaging techniques selected for a test are arranged and displayed in the imaging technique region 2809. The imaging technique region 2809 includes the reconstruction icon 2810 and the thumbnail 2811. In the imaging technique region 2809, imaging technique information such as an imaging technique name is displayed. The reconstruction icon 2810 is a button used to specify execution of reconstruction processing for a tomosynthesis image capturing technique including an image selected for preview. If a plurality of tomosynthesis image capturing techniques are displayed, the button is disabled for all techniques other than the tomosynthesis image capturing technique including an image selected for preview. By giving a specification by the reconstruction icon 2810, it is possible to re-execute reconstruction for a tomosynthesis image capturing technique for which reconstruction processing was performed once. In the imaging technique region 2809 selected for the next irradiation schedule, the imaging-scheduled thumbnail 2811 is displayed in a blank state at a portion scheduled to add a thumbnail at the next irradiation time. When the irradiation schedule selection state is canceled, the imaging-scheduled thumbnail 2811 is hidden. The WL input region 2812 and the WW input region 2813 are portions where a Window Level and a Window Width for an image selected for preview are edited. When a displayed value in an editing box is changed, or a mouse drag is performed on the image region 2802, the editing is applied to an image under preview display. The suspend icon 2814 is a button used to specify to suspend a test under execution. The test control unit 2406 executes test suspending processing. The output icon 2815 is a button used to specify image output of a captured image included in a test under execution. The procedure of processing when image output is specified is the same as image output processing at the end of a test shown in FIG. 27B. The end icon 2816 is a button used to specify an end of a test under execution. The test control unit 2406 executes test end processing. The annotation icon 2817 is a button used to switch between display and hiding of an annotation to be displayed on the image region 2802. The right rotation icon 2818 is a button used to rotate a captured image under preview display clockwise. The left rotation icon 2819 is a button used to rotate a captured image under preview display counterclockwise. The lateral inversion icon 2820 is a button used to invert a captured image under preview display in the lateral direction. The vertical inversion icon 2821 is a button used to invert a captured image under preview display in the vertical direction. The black/white inversion icon 2822 is a button used to invert the Window values of a captured image under preview display. The L mark icon 2823 is a button used to arrange a laterality marker "L" on a captured image under preview display. The button can be turned on/off, and arranges "L" in an ON state and deletes "L" in an OFF state. The R mark icon 2824 is a button used to arrange a laterality marker "R" on a captured image under preview display. The button can be turned on/off, and arranges "R" in an ON state and deletes "R" in an OFF state. The cutout icon 2825 is a button used to specify a cutout setting of a region of interest for a captured image under preview display. The mask icon 2826 is a button used to specify mask processing for a captured image under preview display. The re-image icon 2827 is a button used to specify re-imaging for an imaging technique including an image selected for preview. Re-imaging here indicates processing of executing a process for an image of mis-exposure for an image specified to re-imaging and newly adding the same imaging technique. The mis-exposure image process icon 2828 is a button used to specify a process for an image of mis-exposure for an image selected for preview. When the process for an image of mis-exposure is executed, a mis-exposure image process setting included in image information is switched to ON. The undo icon 2829 is a button used to specify Undo processing of returning the history of processes for an image selected for preview in reverse chronological order. The reset specifying portion 2830 is a button used to specify reset processing of discarding all processes for an image selected for preview and returning to the state immediately after imaging.

Figure 29:
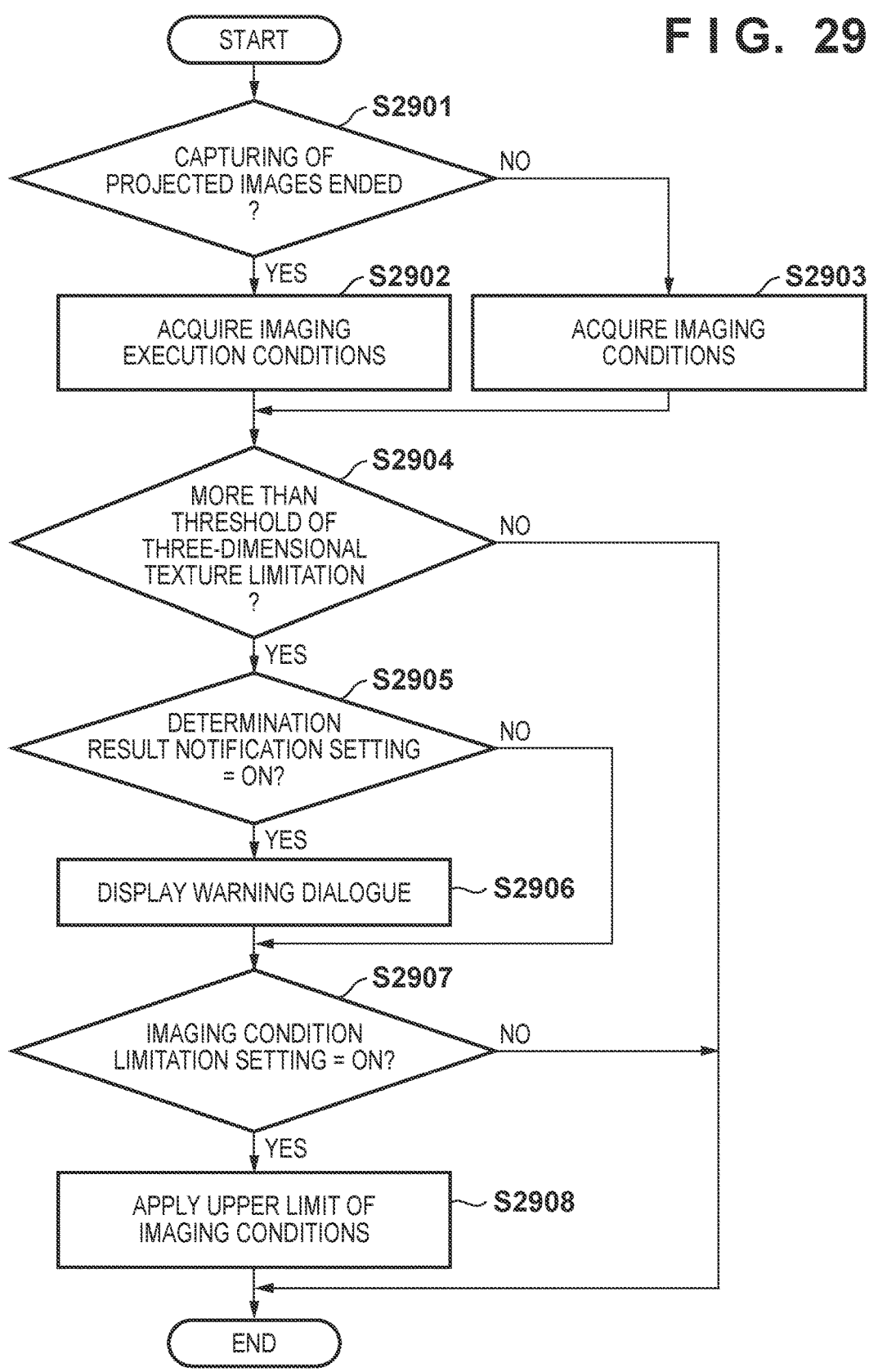
FIG. 29 is a flowchart showing the procedure of processing from three-dimensional texture limitation determination processing to execution of limitations of imaging conditions according to the embodiment of the present invention.

Processing from three-dimensional texture limitation determination processing to execution of imaging condition limitation according to the embodiment of the present invention will be described here with reference to the flowchart of FIG. 29. This processing corresponds to an example of the process performed in step S2703 or S2709 shown in FIG. 27A.

In step S2901, the imaging control unit 2405 determines whether capturing of projected images of a tomosynthesis image capturing technique as a determination target when executing three-dimensional texture limitation determination processing has ended. If capturing of the projected images of the tomosynthesis image capturing technique as the determination target has ended, the process transitions to step S2902. If capturing has not ended, the process transitions to step S2903. In step S2902, the imaging control unit 2405 acquires imaging execution conditions included in the imaging technique information of the tomosynthesis image capturing technique as the determination target, and transmits a three-dimensional texture limitation determination request notification to the 3D determination unit 2401. Note that the three-dimensional texture limitation determination request notification includes at least the imaging technique information, imaging conditions, three-dimensional texture limitation determination setting information, and reconstruction conditions. On the other hand, in step S2903, the imaging control unit 2405 acquires imaging conditions included in the imaging technique information of the tomosynthesis image capturing technique as the determination target, and transmits a three-dimensional texture limitation determination request notification to the 3D determination unit 2401. Upon receiving the three-dimensional texture limitation determination request notification, the 3D determination unit 2401 executes three-dimensional texture limitation determination. The 3D determination unit 2401 calculates the two-dimensional data size of a projected image based on a binning size included in the imaging conditions and the information of a sensor read region, and acquires values in the vertical and horizontal directions. Note that the pieces of information to be used are not particularly limited as long as the two-dimensional data size can be calculated. Then, a height when three-dimensional voxel data is generated is acquired from the slice pitch and the slice count included in the reconstruction conditions. The vertical, horizontal, and height values when reconstructing three-dimensional voxel data are compared with the thresholds of the vertical, horizontal, and height values of a three-dimensional texture limitation included in the three-dimensional texture limitation determination setting information. If at least one of the acquired values is larger than the threshold, it is determined that the size exceeds the limiting value. If all the acquired values are smaller than the thresholds, it is determined that the size is smaller than the limiting value. Upon determining that the size exceeds the limiting value, concerning the imaging conditions used to calculate the two-dimensional data size, a corrected imaging condition close to the imaging condition that is notified and closest out of the imaging conditions smaller than the limiting value is obtained. When the three-dimensional texture limitation determination is executed, the 3D determination unit 2401 transmits a three-dimensional texture limitation determination result notification to the imaging control unit 2405. Note that the three-dimensional texture limitation determination result notification includes at least the determination result and the corrected imaging condition. Next, in step S2904, the imaging control unit 2405 confirms the three-dimensional texture limitation determination result. If the three-dimensional texture limitation determination result is less than the limitation, it is determined that reconstruction is possible, and the processing ends. On the other hand, if the three-dimensional texture limitation determination result exceeds the limitation, in step S2905, it is confirmed whether to notify the determination result. If a determination result notification enable/disable setting included in the three-dimensional texture limitation determination setting information is ON, the imaging control unit 2405 displays a warning dialogue in step S2906. The imaging control unit 2405 transmits a determination result display request notification to the display control unit 2409 via the test control unit 2406. Upon receiving the determination result display request notification, the display control unit 2409 displays a warning dialogue 3001 shown in FIG. 30 on the display unit 2109. After that, when the input detection unit 2407 detects the pressing of an OK button 3002, the display control unit 2409 closes the warning dialogue via the display unit 2109. In addition, the input detection unit 2407 transmits a determination result hiding completion notification to the imaging control unit 2405 via the test control unit 2406. With this processing, even if an imaging condition more than a limiting value is set, the operator is notified of it, thereby changing the imaging condition to a correct imaging condition before imaging. If the determination result hiding completion notification is received, or if the determination result notification enable/disable setting is OFF, the process transitions to step S2907. Next, in step S2907, the imaging control unit 2405 confirms whether to limit the imaging conditions. If an imaging condition limitation enable/disable setting included in the three-dimensional texture limitation determination setting information is OFF, the imaging control unit 2405 ends the processing. On the other hand, if the imaging condition limitation enable/disable setting is ON, the process transitions to step S2908. Next, in step S2908, the upper limit of the limiting condition is applied to the imaging condition. The imaging control unit 2405 updates the imaging condition included in the imaging technique information of the determination target tomosynthesis image capturing technique to the corrected imaging condition included in the three-dimensional texture limitation determination result notification, and ends the processing. Accordingly, even if an imaging condition more than a limiting value is set, the imaging condition is automatically corrected to be less than the limiting value. It is therefore possible to prevent imaging from being performed under wrong imaging conditions.

Figure 28:
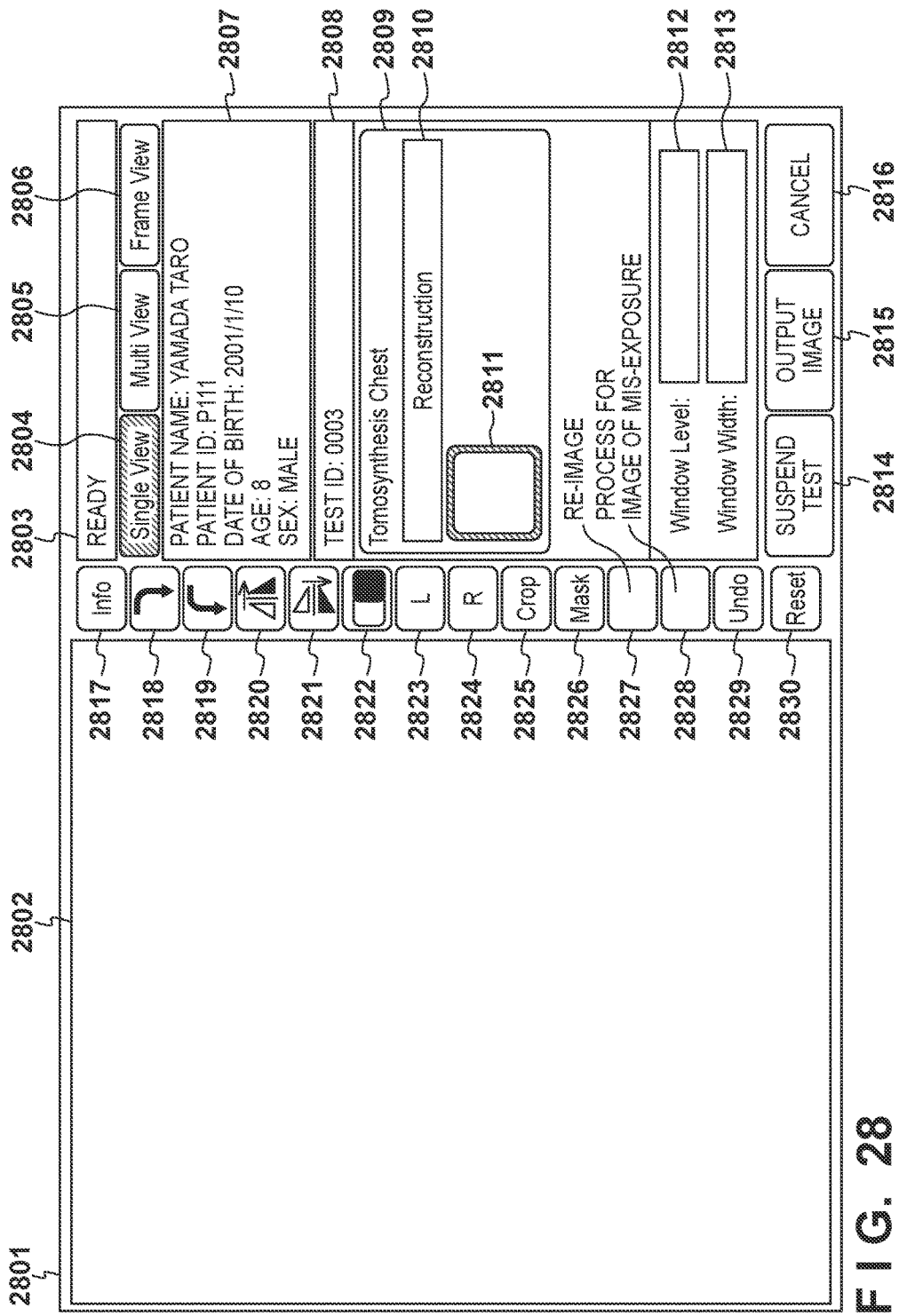
FIG. 28 is a view showing an imaging screen before imaging according to the embodiment of the present invention.
Figure 30:
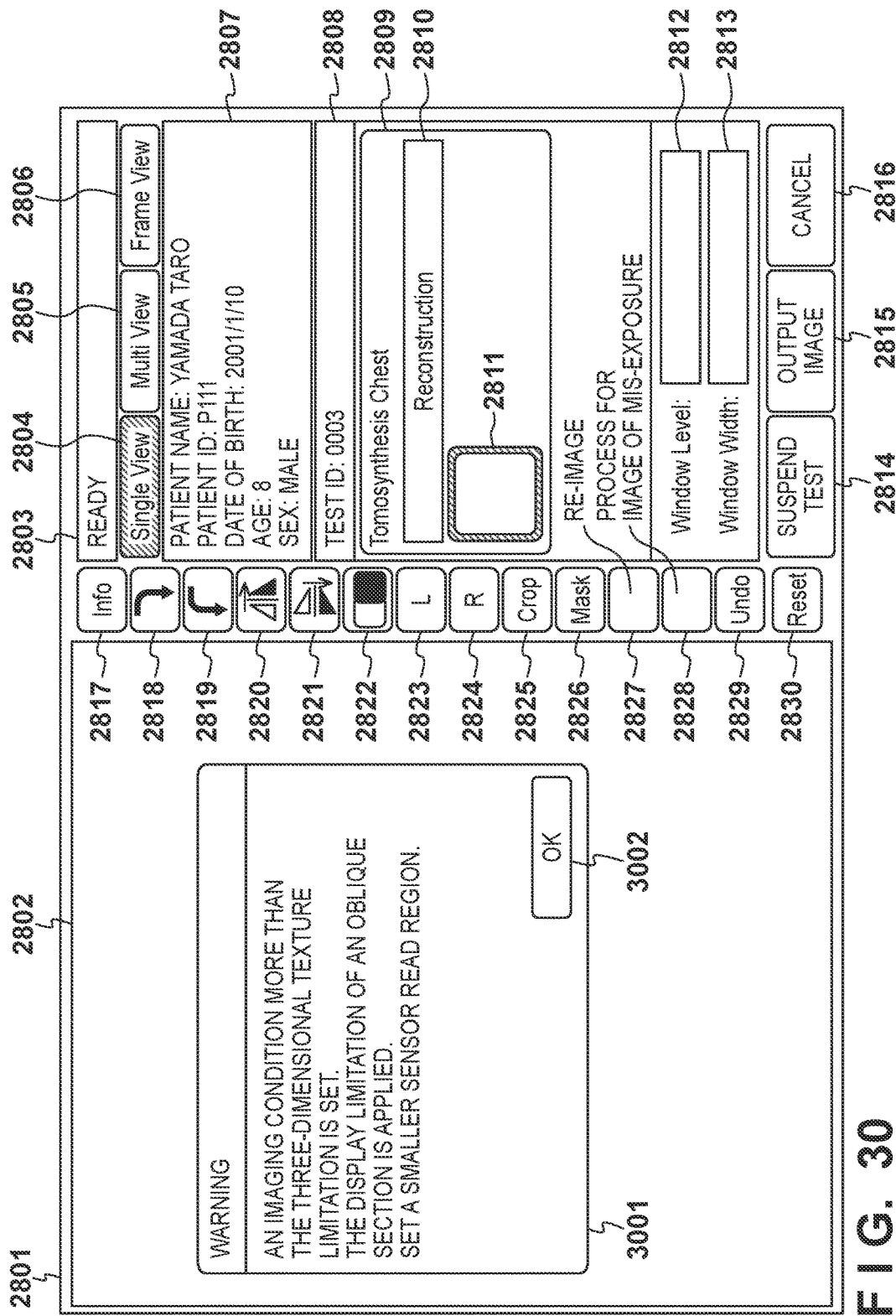
FIG. 30 is a view showing an imaging screen in a case in which a three-dimensional texture limitation determination result is notified according to the embodiment of the present invention.

FIG. 30 shows a state in which the warning dialogue 3001 is displayed in the imaging screen 2801 shown in FIG. 28 by the process of step S2906. The warning dialogue 3001 is a display used to notify information based on the result of determination by the 3D determination unit 2401. The warning dialogue 3001 displays a text "An imaging condition more than the three-dimensional texture limitation is set. The display limitation of an oblique section is applied. Set a smaller sensor read region". The contents of the text to be displayed are not limited to these, and it is only necessary to display information representing the determination result, information representing that reconstruction of three-dimensional volume data is limited or impossible, or information for recommending to change an imaging condition.

Figure 31:
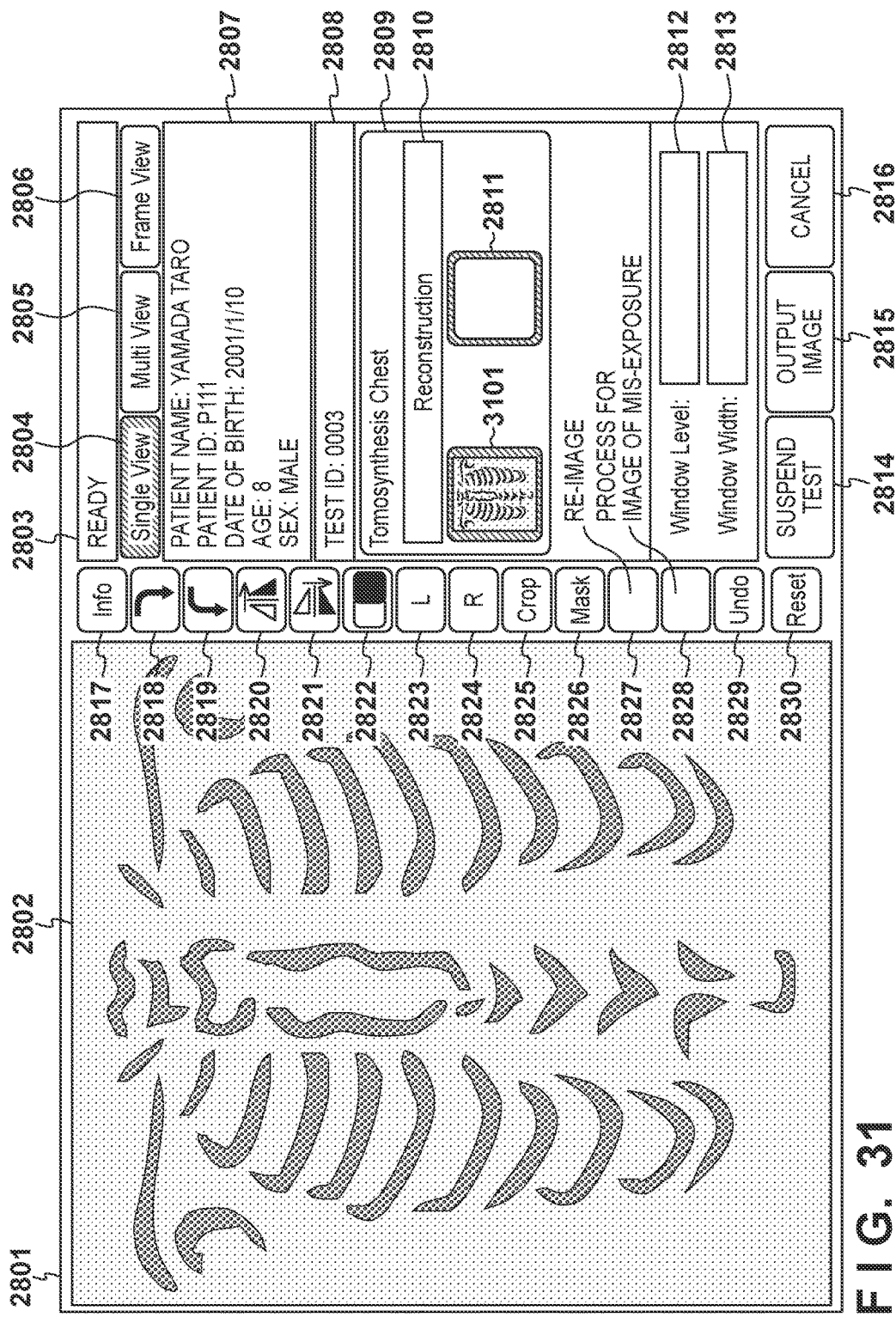
FIG. 31 is a view showing an imaging screen after imaging according to the embodiment of the present invention.

An example of the imaging screen 2801 immediately after projected image capturing in step S2708 of FIG. 27A or immediately after reconstruction processing determination in step S2709 will be described next with reference to FIG. 31. When projected image capturing ends, a captured image thumbnail 3101 corresponding to an acquired projected image or a tomographic image of determined reconstruction processing is displayed in the imaging technique region 2809 of the tomosynthesis image capturing technique. A thumbnail image corresponding to a projected image, an imaging type mark, a similarity mark, and a mis-exposure image process mark are displayed on the captured image thumbnail 3101. The imaging type mark is a mark capable of making a distinction between imaging types, that is, a still image, fluoroscopy, cine, and tomosynthesis image. For example, "C" is used for cine, and "T" is used for a tomosynthesis image. However, the mark is not limited to this as long as it can make a distinction between imaging types. When the captured image thumbnail 3101 is selected, the preview display is switched. The imaging screen 2801 having the above-described arrangement is displayed.

Figure 32A:
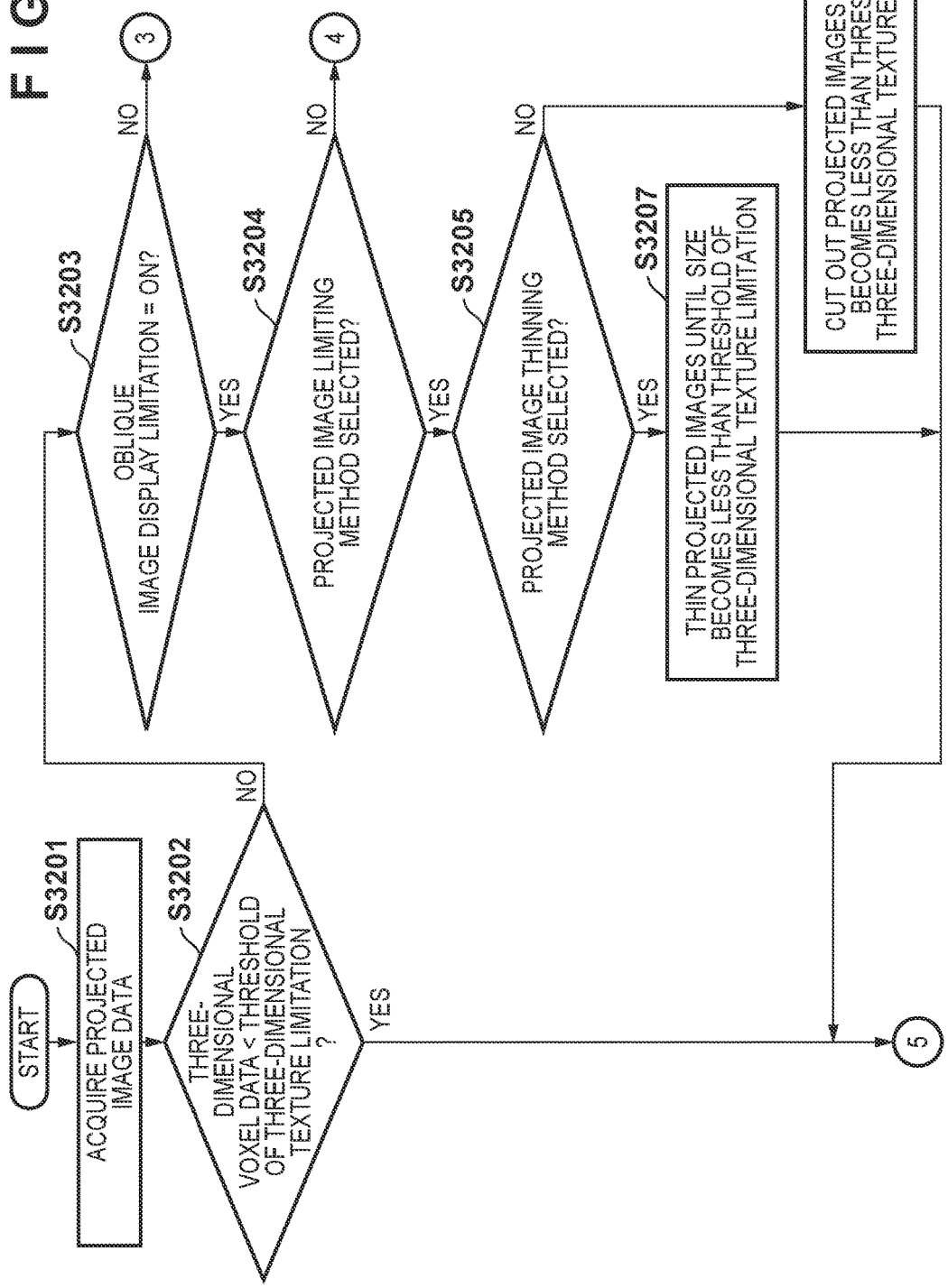
FIGS. 32A and 32B are flowcharts showing the procedure of processing from three-dimensional texture limitation determination processing to execution of limitations of oblique cross-sectional image display according to the embodiment of the present invention.
Figure 32B:
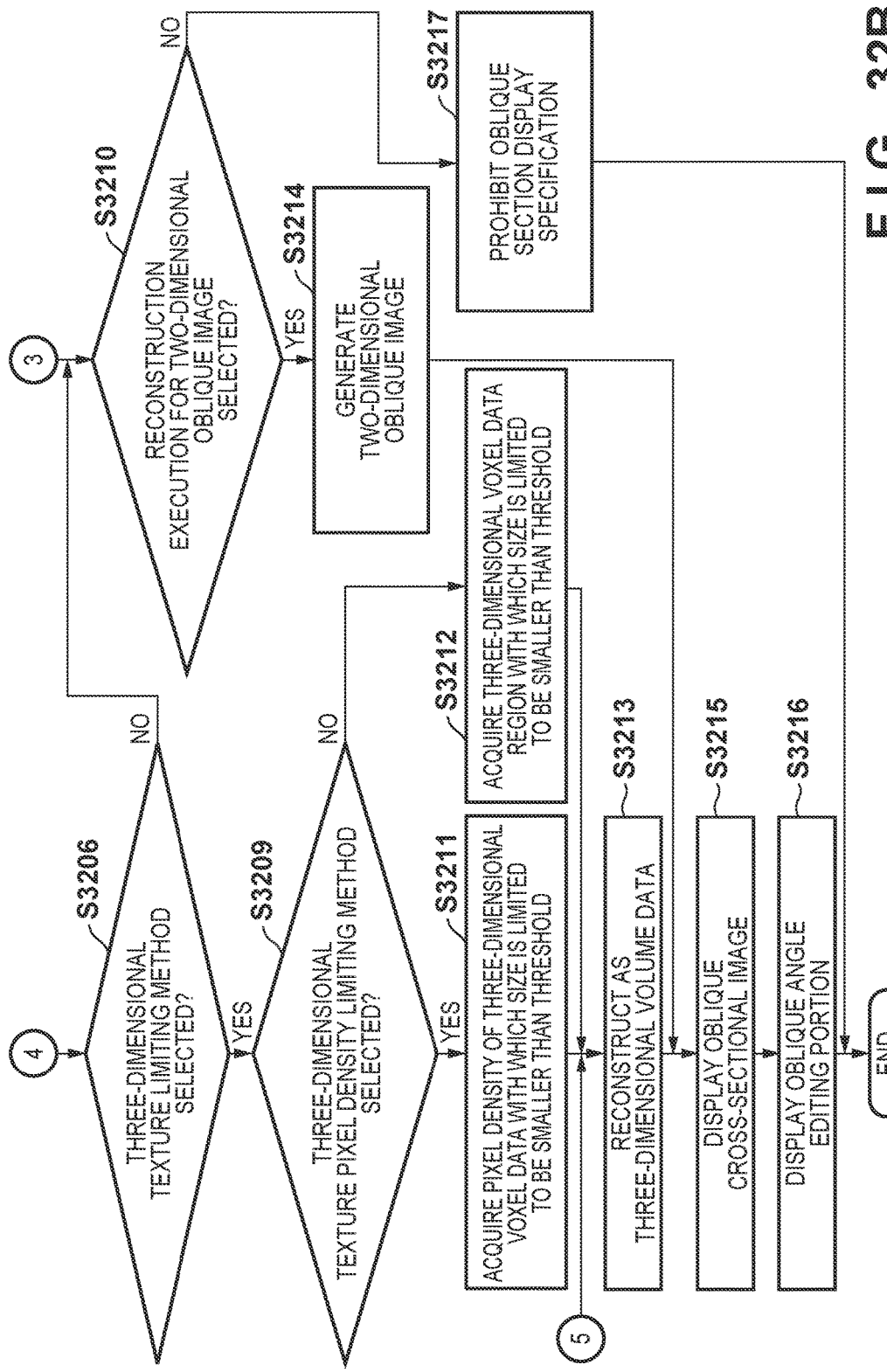

An example of the procedure of processing from three-dimensional texture limitation determination processing to execution of oblique cross-sectional image display limitation according to the present invention will be described here with reference to FIGS. 32A and 32B. First, in step S3201, the imaging control unit 2405 acquires the X-ray image data of projected images used for reconstruction processing concerning a tomosynthesis image capturing technique as a reconstruction target. Next, in step S3202, three-dimensional texture limitation determination processing is executed. The imaging control unit 2405 transmits a three-dimensional texture limitation determination request notification to the 3D determination unit 2401. Upon receiving the three-dimensional texture limitation determination request notification, the 3D determination unit 2401 executes three-dimensional texture limitation determination. Additionally, the 3D determination unit 2401 refers to an oblique section display limiting method included in the imaging technique information. If an oblique section display limitation application enable/disable setting is ON, the selected display limiting method is added to a three-dimensional texture limitation determination result notification. If "reduce the pixel size of three-dimensional voxel data" is selected, the 3D determination unit 2401 calculates the maximum pixel size for three-dimensional voxel data of a size smaller than the limitation. The pixel size is added to the three-dimensional texture limitation determination result notification as a corrected three-dimensional voxel data pixel size. If "reduce the three-dimensional voxel data size" is selected, the 3D determination unit 2401 calculates the maximum data size for three-dimensional voxel data of a size smaller than the limitation, and adds the data size to the three-dimensional texture limitation determination result notification as a corrected three-dimensional voxel data size. When the three-dimensional texture limitation determination is executed, the 3D determination unit 2401 transmits the three-dimensional texture limitation determination result notification to the imaging control unit 2405. The imaging control unit 2405 confirms the three-dimensional texture limitation determination result. If the three-dimensional texture limitation determination result is less than the limitation, it is determined that the data can be reconstructed as three-dimensional volume data, and the process transitions to step S3213. On the other hand, if the three-dimensional texture limitation determination result exceeds the limitation, the process transitions to step S3203. Next, in step S3203, it is confirmed whether to execute oblique image display limitation. The imaging control unit 2405 refers to the oblique section display limiting method included in the three-dimensional texture limitation determination result notification. If any method is selected as the oblique section display limiting method, it is determined that the oblique image display limitation is ON, and the process transitions to step S3204. If no method is selected, it is determined that the oblique image display limitation is OFF, and the process transitions to step S3210. Next, in step S3204, it is determined whether a projected image limiting method is selected. The imaging control unit 2405 refers to the oblique section display limiting method included in the three-dimensional texture limitation determination result notification. If "thin projected images" or "cut out projected images" is selected as the oblique section display limiting method, the process transitions to step S3205. If a method other than those described above is selected, the process transitions to step S3206. Next, in step S3205, it is determined whether a projected image thinning method is selected. If "thin projected images" is selected as the oblique section display limiting method, the process transitions to step S3207. On the other hand, if "cut out projected images" is selected, the process transitions to step S3208. Next, in step S3207, the projected image data is thinned until its size becomes less than the threshold of the three-dimensional texture limitation. The imaging control unit 2405 transmits a projected image thinning request notification to the image processing unit 2110. Note that the projected image thinning request notification includes at least the imaging technique information, the X-ray image data, and thinning information. Thinning information here is information used to reduce the data size by thinning X image data, like a pinning size. Upon receiving the projected image thinning request notification, the image processing unit 2110 applies the thinning information to the X-ray image data and generates thinned X-ray image data. After that, the image processing unit 2110 transmits a projected image thinning completion notification to the imaging control unit 2405. Note that the projected image thinning completion notification includes at least the imaging technique information and the thinned X-ray image data. Upon receiving the projected image thinning completion notification, the imaging control unit 2405 transmits a reconstruction request notification to the image processing unit 2110, and the process transitions to step S3213. At this time, thinned image data is input to the X-ray image data included in the reconstruction request notification, and the pixel size and the data size of the thinned image data are input to the three-dimensional voxel data pixel size and the three-dimensional voxel data size. On the other hand, in step S3208, the imaging control unit 2405 cuts out the projected image data until its size becomes less than the threshold of the three-dimensional texture limitation. The imaging control unit 2405 transmits a projected image cutout request notification to the image processing unit 2110. Note that the projected image cutout request notification includes at least the imaging technique information, the X-ray image data, and cutout information. Cutout information here is coordinate information used to cut out a two-dimensional region from X image data. Upon receiving the projected image cutout request notification, the image processing unit 2110 applies the cutout information to the X-ray image data and generates cutout X-ray image data. After that, the image processing unit 2110 transmits a projected image cutout completion notification to the imaging control unit 2405. Note that the projected image thinning completion notification includes at least the imaging technique information and the cutout X-ray image data. Upon receiving the projected image thinning completion notification, the imaging control unit 2405 transmits a reconstruction request notification to the image processing unit 2110, and the process transitions to step S3213. At this time, cutout image data is input to the X-ray image data included in the reconstruction request notification, and the pixel size and the data size of the thinned image data are input to the three-dimensional voxel data pixel size and the three-dimensional voxel data size. On the other hand, if a method other than "thin projected images" or "cut out projected images" is selected as the oblique section display limiting method, it is determined in step S3206 whether a three-dimensional texture limiting method is selected. The imaging control unit 2405 refers to the oblique section display limiting method included in the three-dimensional texture limitation determination result notification. If "reduce the pixel size of three-dimensional voxel data or" reduce "the three-dimensional voxel data size" is selected as the oblique section display limiting method, the process transitions to step S3209. If a method other than those described above is selected, the process transitions to step S3210. Next, in step S3209, it is determined whether a three-dimensional pixel density limiting method is selected. If "reduce the pixel size of three-dimensional voxel data" is selected as the oblique section display limiting method, the process transitions to step S3211. On the other hand, if "reduce the three-dimensional voxel data size" is selected, the process transitions to step S3212. Next, in step S3211, the imaging control unit 2405 acquires corrected three-dimensional voxel data pixel size included in the three-dimensional texture limitation determination result notification. The imaging control unit 2405 transmits a reconstruction request notification to the image processing unit 2110, and the process transitions to step S3213. At this time, the acquired X image data is directly input to the X-ray image data included in the reconstruction request notification, and the data size of the X image data is input to the three-dimensional voxel data size. In addition, the acquired corrected three-dimensional voxel data pixel size is input to the three-dimensional voxel data pixel size. The process transitions to step S3213. On the other hand, in step S3212, the imaging control unit 2405 acquires a corrected three-dimensional voxel data size included in the three-dimensional texture limitation determination result notification. The imaging control unit 2405 transmits a reconstruction request notification to the image processing unit 2110, and the process transitions to step S3213. At this time, the acquired X image data is directly input to the X-ray image data included in the reconstruction request notification, and the pixel size of the X image data is input to the three-dimensional voxel data pixel size. In addition, the acquired corrected three-dimensional voxel data size is input to the three-dimensional voxel data size. Next, in step S3213, reconstruction of three-dimensional volume data is executed. The imaging control unit 2405 transmits a reconstruction request notification to the image processing unit 2110. Upon receiving the reconstruction request notification, the image processing unit 2110 executes reconstruction processing using the default reconstruction parameters of the imaging technique information, the position information, the X-ray image data, and the pixel size and the data size of the three-dimensional voxel data. When the reconstruction processing is completed, the image processing unit 2110 transmits a reconstruction completion notification to the imaging control unit 2405. Upon receiving the reconstruction completion notification, the imaging control unit 2405 transmits an oblique cross-sectional image acquisition notification to the image processing unit 2110. Upon receiving the oblique cross-sectional image acquisition notification, the image processing unit 2110 acquires an oblique cross-sectional image having a designated oblique section central position and oblique section angle from the three-dimensional voxel data, and transmits it to the imaging control unit 2405 as an oblique cross-sectional image notification. Upon receiving the oblique cross-sectional image notification, the imaging control unit 2405 adds the image information of the acquired oblique cross-sectional image to the oblique cross-sectional image notification, and transmits the oblique cross-sectional image notification to the display control unit 2409 via the test control unit 2406. By executing control for projected images used to reconstruct an oblique section or control for three-dimensional voxel data to be reconstructed, three-dimensional voxel data can be reconstructed even if projected images that exceed the three-dimensional texture limitation are captured. It a three-dimensional texture limiting method is not selected in step S3206, it is determined in step S3210 whether reconstruction execution for a two-dimensional oblique image is selected. The imaging control unit 2405 refers to the oblique section display limiting method included in the three-dimensional texture limitation determination result notification. If the oblique image display limitation is OFF, or "reconstruct an oblique section by two-dimensional data" is selected, the process transitions to step S3214. Next, in step S3214, reconstruction processing of a two-dimensional oblique cross-sectional image is executed. The imaging control unit 2405 transmits a two-dimensional oblique cross-sectional image reconstruction request notification to the image processing unit 2110. Note that the two-dimensional oblique cross-sectional image reconstruction request notification includes at least the imaging technique information, the X-ray image data, the position information, the oblique section isocenter, and the oblique section angle. Upon receiving the two-dimensional oblique cross-sectional image reconstruction request notification, the image processing unit 2110 executes reconstruction processing using the default reconstruction parameters of the imaging technique information, the position information, and the X-ray image data, and generates a two-dimensional oblique cross-sectional image. When the reconstruction processing is completed, the image processing unit 2110 transmits a two-dimensional oblique image reconstruction completion notification to the imaging control unit 2405. Note that the two-dimensional oblique image reconstruction completion notification includes at least the generated oblique cross-sectional image, the reconstruction parameters, the image processing parameters, the oblique section central position, and the oblique section angle. Upon receiving the two-dimensional oblique image reconstruction completion notification, the imaging control unit 2405 adds imaging technique information including the image information of the acquired two-dimensional oblique cross-sectional image to the two-dimensional oblique image reconstruction completion notification, and transmits the two-dimensional oblique image reconstruction completion notification to the display control unit 2409 via the test control unit 2406. Next, in step S3215, the oblique cross-sectional image is displayed. Upon receiving the reconstruction completion notification or two-dimensional oblique image reconstruction completion notification, the display control unit 2409 preview-displays the tomosynthesis image in a tomographic image region 3302 displayed on the display unit 2109, and updates the displayed annotation. Next, in step S3217, an oblique angle editing portion is displayed. After executing the preview display of the oblique cross-sectional image, the display unit 2109 hides a cross section display 3322, and displays an oblique angle editing portion 3401. After that, the display angle of a guideline image 3406 included in the oblique angle editing portion 3401 is updated to the same display angle as the preview-displayed oblique cross-sectional image, and the processing ends. On the other hand, if "prohibit oblique section display" is selected in step S3210, specification of oblique section display is prohibited in step S3218. The imaging control unit 2405 transmits an oblique section display prohibition notification to the display control unit 2409 via the test control unit 2406. The display control unit 2409 disables an oblique icon 3306 in a reconstruction screen 3301 displayed on the display unit 2109, prohibits oblique section display, and ends the processing.

Figure 35:
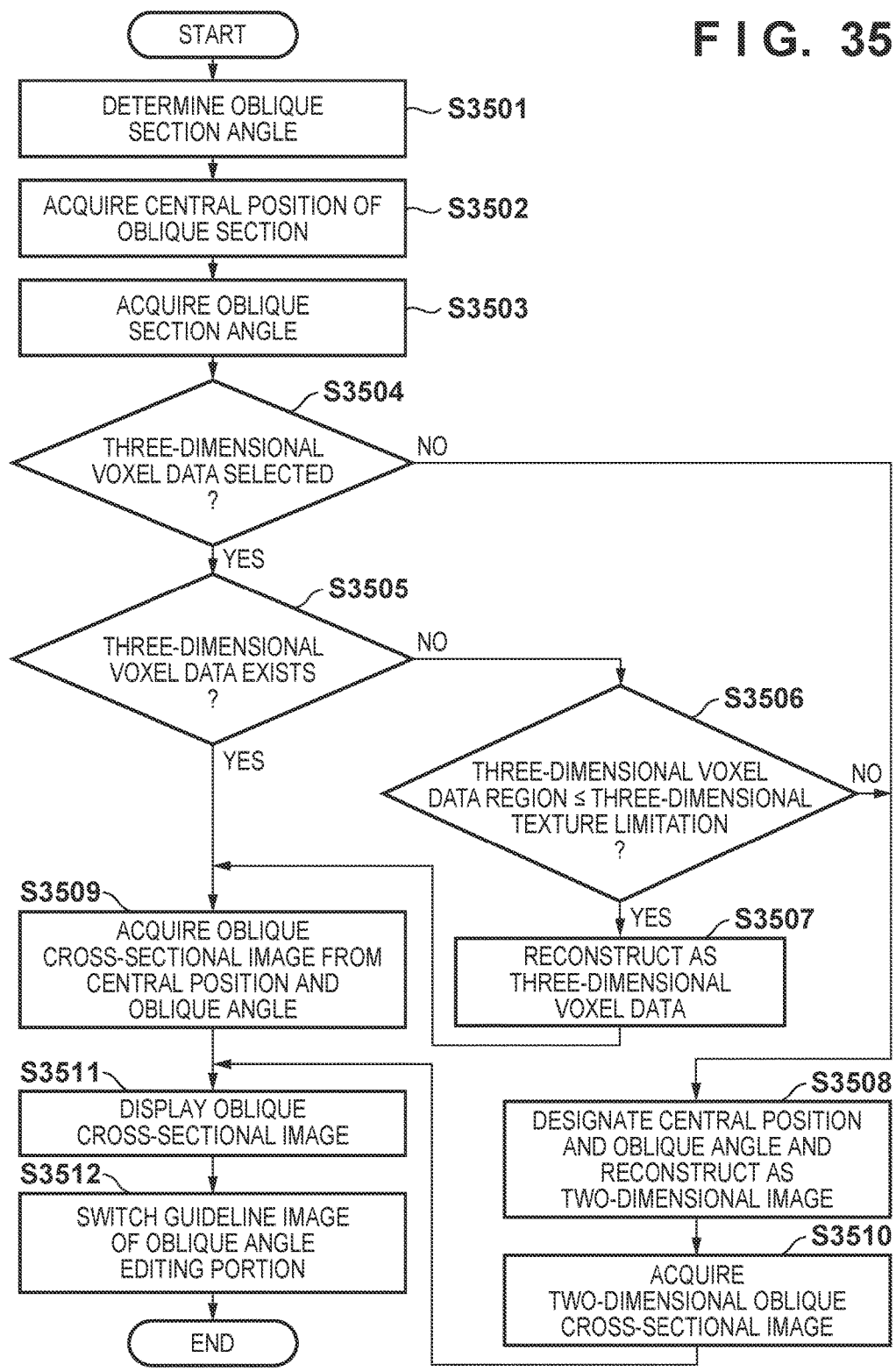
FIG. 35 is a flowchart showing the procedure of processing from the start to the end of oblique section angle change according to the embodiment of the present invention.

An example of the reconstruction screen 3301 at the time of coronal cross-sectional image display, which is displayed in step S2709 of FIG. 27A, will be described next with reference to FIG. 33. On the reconstruction screen 3301, Window processing, reproduction processing, or re-execution of reconstruction processing by editing the reconstruction parameters is performed for a tomosynthesis image. In addition, a coronal cross-sectional image with high image accuracy or an oblique cross-sectional image at an arbitrary angle can selectively be displayed. At this time, in the present invention, an oblique section can be displayed by a limiting method set for each imaging technique even using projected image data that exceed the three-dimensional texture limitation. Furthermore, when editing the angle of an oblique section, the angle switching method is branched by the oblique section display limiting method, thereby smoothly switching the display (FIG. 35).

Figure 33:
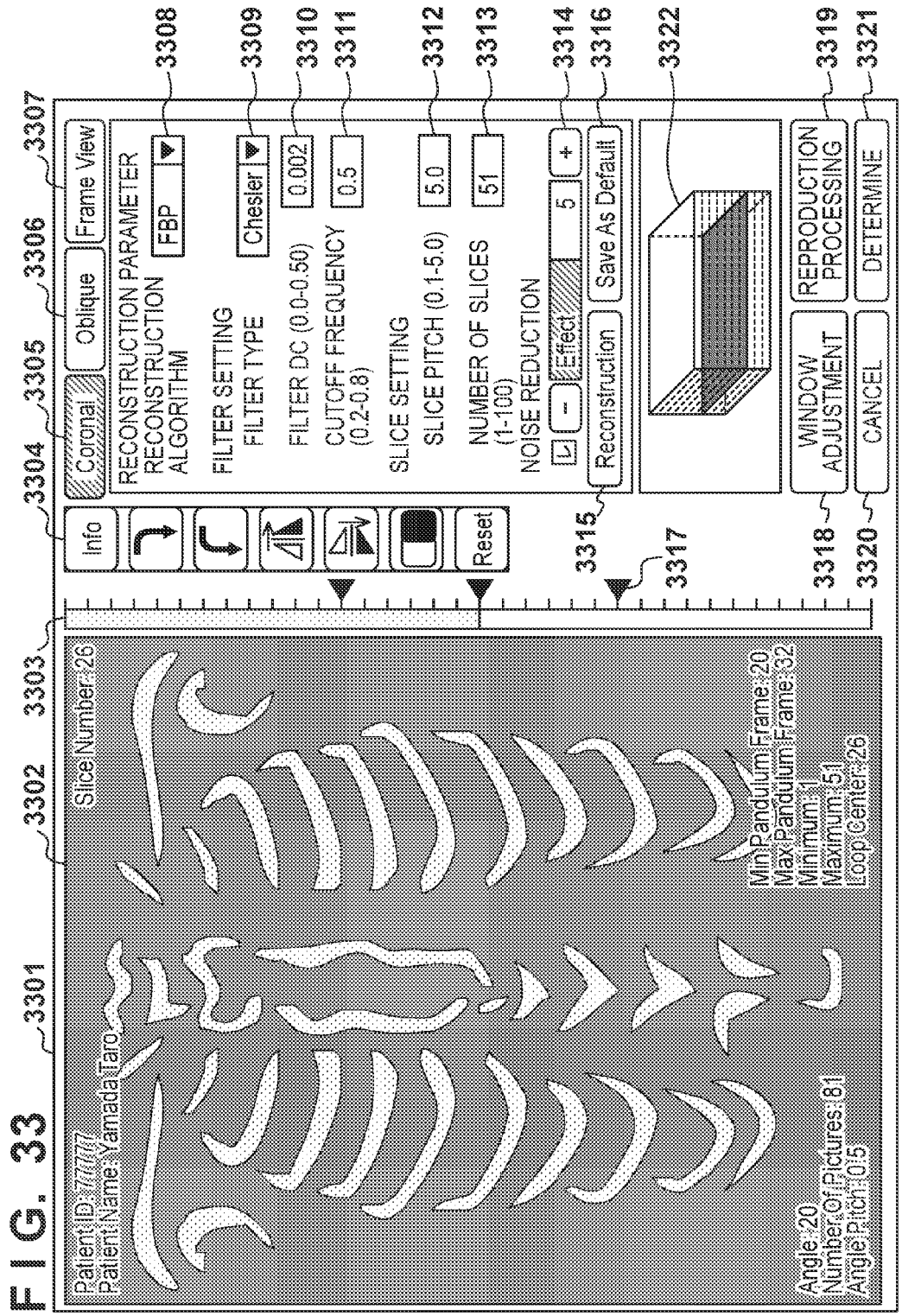
FIG. 33 is a view showing a reconstruction screen in a case in which a coronal cross-sectional image is displayed according to the embodiment of the present invention.

The reconstruction screen 3301 shown in FIG. 33 is formed from the tomographic image region 3302, a frame slider 3303, an image tool bar 3304, a coronal icon 3305, the oblique icon 3306, a frame view icon 3307, an algorithm input region 3308, a filter input region 3309, a DC input region 3310, a cutoff input region 3311, a pitch input region 3312, a slice count input region 3313, a noise process input region 3314, a reconstruction button 3315, a default setting icon 3316, a reproduction range icon 3317, a W adjustment icon 3318, a reproduction icon 3319, a cancel button 3320, a determination button 3321, and the cross section display 3322. The tomographic image region 3302 preview-displays a tomosynthesis image after reconstruction processing. During execution of reconstruction processing, a progress bar that notifies the user that reconstruction processing is underway is displayed, and the tomosynthesis image is displayed at the same time as completion of the reconstruction processing. The frame slider 3303 confirms or switches a displayed frame image in the tomosynthesis image under preview display. At the same time as the preview display of the tomosynthesis image, scales corresponding to all valid frames of the tomosynthesis image under preview display are uniformly displayed on a side of the slider from the upper end to the lower end. Control is performed to enable designation of only valid frames, thereby eliminating the risk to erroneously display an invalid frame. A frame of a number corresponding to a scale selected by selecting or dragging on the frame slider 3303 is displayed in the tomographic image region 3302. The image tool bar 3304 arranges controls to specify processing for the tomosynthesis image under preview display. The arranged controls are the same as the buttons 2717 to 2730 on the imaging screen 2801. The coronal icon 3305 is a button used to specify to display the tomosynthesis image displayed in the tomographic image region 3302 as a coronal section. The oblique icon 3306 is a button used to specify to display the tomosynthesis image displayed in the tomographic image region 3302 as an oblique section. The frame view icon 3307 is a button used for switching to frame view that divides the tomographic image region 3302 into a plurality of display regions in a matrix and in parallel displays frame images of the tomosynthesis image under preview display. During oblique section display, the button is disabled, and frame view display is impossible. The algorithm input region 3308 is a control that selects a reconstruction method such as FBP (Filter Back Projection) or shift-and-add method. The filter input region 3309 is a control that selects a filter type used when performing reconstruction processing. The DC input region 3310 is a control that edits the DC parameter of a filter used when performing reconstruction processing. The cutoff input region 3311 is a control that edits the cutoff frequency of a filter used when performing reconstruction processing. The pitch input region 3312 is a control that edits the thickness between frames when performing reconstruction processing. The slice count input region 3313 is a control that edits the total number of frames when performing reconstruction processing. The noise process input region 3314 includes a control that switches whether to apply a noise reduction process when performing reconstruction processing and a control that edits the degree of influence when applying. The reconstruction button 3315 is a button that specifies execution of reconstruction processing. Reconstruction is executed again using reconstruction parameters input at the time of the pressing of the button. At this time, the same projected images as those for the tomosynthesis image under preview display are used. The default setting icon 3316 is a button that specifies to change the default reconstruction parameters of the tomosynthesis image capturing technique under preview display. When the button is pressed, the imaging control unit 2405 transmits a reconstruction parameter change notification to the test control unit 2406 together with the reconstruction parameters under display. The test control unit 2406 updates the reconstruction parameters of the tomosynthesis image capturing technique of the reconstruction parameter target, and transmits a "registration/updating" processing request to the imaging technique list storage unit 2402. The reproduction range icon 3317 is a control that designates the reproduction range at the time of reciprocal reproduction of range designation. The control includes controls to designate the minimum frame number, the central frame number, and the maximum frame numbers. By moving the controls, the range from the designated minimum frame number to the maximum frame number is designated as the reproduction range. The W adjustment icon 3318 is a button that switches between display and hiding of a Window adjustment control. When the W adjustment icon 3318 is switched to ON, a Window adjustment portion is displayed in the display region of the cross section display 3322 to enable adjustment of a Window value. When the W adjustment icon 3318 is switched to OFF, the Window adjustment portion is hidden, and the cross section display 3322 is displayed. The reproduction icon 3319 is a button that switches between display and hiding of a reproduction processing control. When the reproduction icon 3319 is switched to ON, a reproduction processing portion is displayed in the display region of the cross section display 3322 to enable continuous reproduction/frame advance/frame back of the frames of tomographic images. When the reproduction icon 3319 is switched to OFF, the reproduction processing portion is hidden, and the cross section display 3322 is displayed. The cancel button 3320 is a button that specifies to discard the tomosynthesis image under preview. When reconstruction cancel is specified, step S2709 is completed without storing the tomosynthesis image and image information, and the screen transitions to the imaging screen 2801. On the imaging screen 2801, the image previewed before the reconstruction screen display is continuously selected for preview. The determination button 3321 is a button that specifies storage determination of the tomosynthesis image under preview. When storage determination is specified, the tomosynthesis image under preview is stored in the HDD 2505. After that, step S2709 is completed, and the screen transitions to the imaging screen 2801. On the imaging screen 2801, the captured image thumbnail 3101 of the stored tomographic image is added to the imaging technique region 2809 of the tomosynthesis image capturing technique including the tomographic image for which the reconstruction processing is determined and selected for preview. The cross section display 3322 is a control that 3D-displays a pseudo frame of the generated tomosynthesis image and designates a display frame. Ruled lines that relatively indicate the positional relationships of the frames of tomosynthesis images are displayed on the cross section display 3322, and a reduced image is displayed at the position of the same frame number as the displayed frame image. By selecting a ruled line on the cross section display 3322 or performing a mouse drag, the display frame can easily be switched. Ruled lines corresponding to only valid frames of the tomosynthesis image are displayed on the cross section display 3322. In addition, the positional relationship of the frames of tomosynthesis images after reconstruction processing is overlaid on the current state and preview-displayed in synchronism with editing of the slice pitch or slice count. The reconstruction screen 3301 having the above-described arrangement is displayed.

Figure 34A:
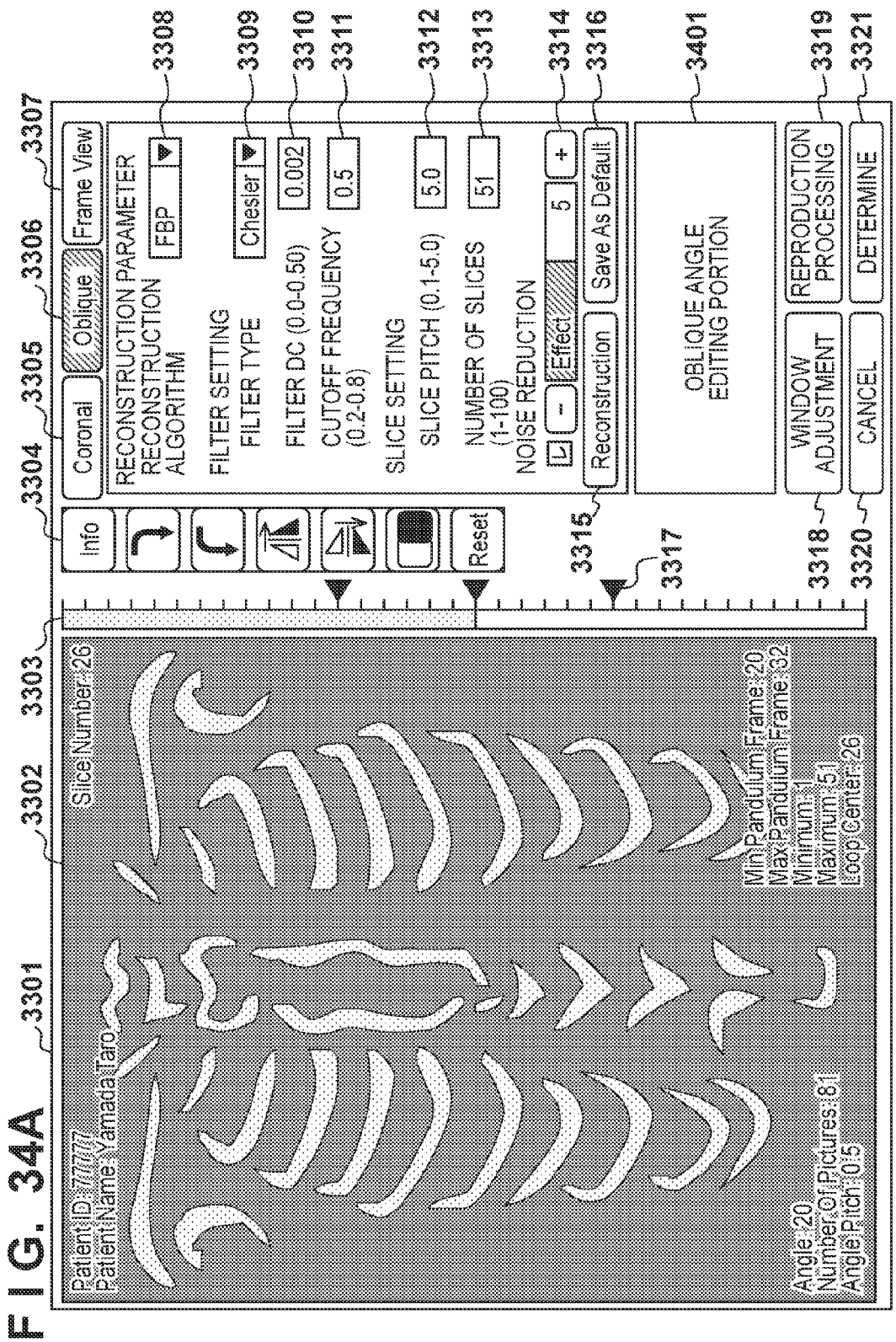
FIGS. 34A and 34B are views showing a reconstruction screen in a case in which an oblique cross-sectional image is displayed according to the embodiment of the present invention.
Figure 34B:
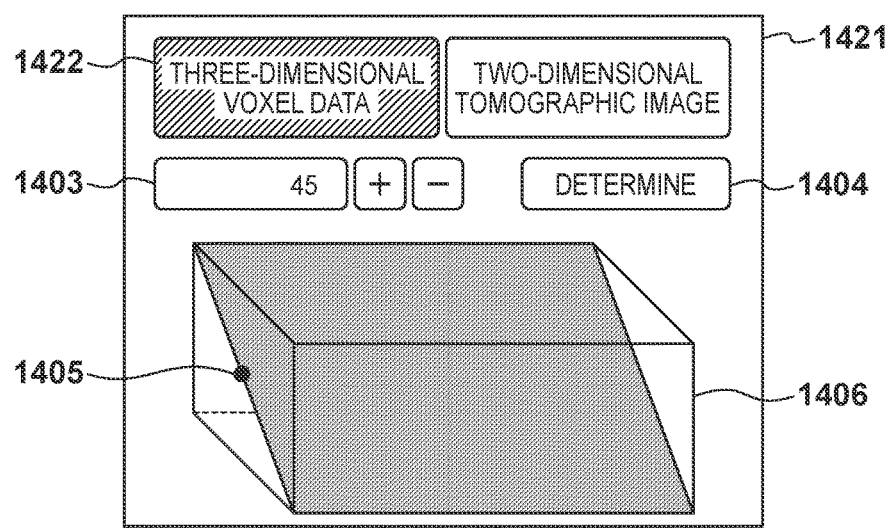

The reconstruction screen 3301 at the time of oblique section display, which is displayed in step S2709 of FIG. 27A, will be described next with reference to FIGS. 34A and 34B. On the reconstruction screen 3301 shown in FIG. 34A, the elements from the tomographic image region 3302 to the determination button 3321 are the same as in FIG. 33. When the reconstruction oblique icon 3306 is pressed, the cross section of the tomosynthesis image displayed in the tomographic image region 3302 changes from a coronal section to an oblique section. During oblique section display, frame designation by the frame slider 3303 or a reproduction specification from a reproduction processing portion 3901 is neglected. In addition, the frame view icon 3307 is disabled, and frame view is impossible. When the reconstruction oblique icon 3306 is being selected, the cross section display 3322 is hidden, and an oblique angle editing portion 1421 shown in FIG. 34B is displayed. The oblique angle editing portion 1421 is formed from an oblique image reconstruction method specifying portion 1422, an oblique angle specifying portion 1403, an oblique angle determination specifying portion 1404, an oblique section center specifying portion 1405, and a guideline image display portion 1406. The oblique image reconstruction method specifying portion 1422 is an icon used to switch whether to reconstruct an oblique cross-sectional image as three-dimensional voxel data or a two-dimensional oblique image. This makes it possible to selectively display the reconstruction method of the oblique section later in accordance with the purpose irrespective of the default reconstruction method. The oblique angle specifying portion 1403 is a region to edit the oblique angle of the oblique cross-sectional image to be displayed. It is possible to not only increase/decrease the angle by pressing the + and − buttons but also edit the angle by free input via a keyboard or touch panel or using a mouse wheel. The oblique angle determination specifying portion 1404 determines the edited oblique angle, and specifies display switching of the oblique section. The oblique section center specifying portion 1405 can be moved to an arbitrary position in the guideline image, and designates the center of the oblique section. The guideline image display portion 1406 is a region to display a reduced image obtained by applying the currently designated position of the center and the currently designated oblique angle to the displayed pseudo three-dimensional voxel region. Note that the oblique angle can also be edited even on the guideline image display portion 1406 by operating the mouse wheel or the like. The reconstruction screen 3301 at the time of oblique section display with the above-described arrangement is displayed.

The display control unit 2409 changes the operation method for designating the oblique section as the display target between a case in which three-dimensional volume data (three-dimensional voxel data) is reconstructed, and an oblique cross-sectional image is generated based on this in the oblique angle editing portion 3401 and a case in which the image processing unit 2110 reconstructs an oblique cross-sectional image based on the plurality of projected images. For example, in a case in which three-dimensional volume data is not reconstructed, designation of a cross section according to an operation on the mouse wheel or oblique image generation according to a swipe operation on the touch panel is disabled. This is because in a case in which three-dimensional volume data is absent, there may be stress on the operator if it is difficult to generate an oblique image in quick response to designation of a cross section by the mouse wheel operation or swipe operation. If the generation speed is sufficient, such an operation method change is not always necessary, as a matter of course.

In one embodiment, the display control unit 2409 causes an oblique angle specifying portion 3403 to display the angle of an oblique cross-sectional image concerning past tomosynthesis. For example, the imaging control unit 2405 determines whether the information of an oblique cross-sectional image in tomosynthesis image capturing performed for the same subject under the same imaging conditions is stored in the imaging control apparatus 2107 or the PACS 2115. If the information is stored, the display control unit 2409 causes the oblique angle specifying portion 3403 to display the angle of the oblique cross-sectional image. This facilitates observing the same cross section as an oblique image obtained by previously performed tomosynthesis.

An example of the procedure of processing from the start to the end of oblique section angle change executed in step S2709 of FIG. 27A will be described here with reference to FIG. 35. First, in step S3501, an oblique section angle is determined. Determination of the oblique section angle is done, for example, at the timing when the oblique angle is edited by the oblique angle specifying portion 1403, at the timing when the oblique angle determination specifying portion 1404 is pressed, or at the timing when the angle of the guideline image is edited by the guideline image display portion 1406. When the oblique section angle is determined, the operation unit 2108, the input detection unit 2407 acquires the central position of the determined oblique section, the oblique section angle, and the oblique image reconstruction method in steps S3502 and S3503. The input detection unit 2407 transmits an oblique section information acquisition notification to the display control unit 2409. Upon receiving the oblique section information acquisition notification, the display control unit 2409 acquires the oblique section central position and the value of the oblique section angle designated in the oblique angle editing portion 1421 displayed on the reconstruction screen 3301, and transmits an oblique section information notification to the imaging control unit 2405. Note that the oblique section information notification includes at least the oblique section central position, the oblique section angle, and the oblique image reconstruction method. In step S3504, the imaging control unit 2405 confirms based on the oblique image reconstruction method included in the oblique section information whether to reconstruct three-dimensional voxel data. To reconstruct three-dimensional voxel data, the process transitions to step S3505. Next, in step S3505, the imaging control unit 2405 confirms based on the image information of tomographic images specified to display an oblique section whether three-dimensional voxel data is already reconstructed. If three-dimensional voxel data is already reconstructed, the process transitions to step S3509. Next, in step S3509, the imaging control unit 2405 transmits an oblique cross-sectional image acquisition notification to the image processing unit 2110. Note that the oblique cross-sectional image acquisition notification includes at least the three-dimensional voxel data, the oblique section central position, and the oblique section angle. Upon receiving the oblique cross-sectional image acquisition notification, the image processing unit 2110 acquires an oblique cross-sectional image with the designated oblique section central position and oblique section angle from the three-dimensional voxel data, and transmits an oblique cross-sectional image notification to the imaging control unit 2405. Note that the oblique cross-sectional image notification includes at least oblique cross-sectional image data, the oblique section central position, and the oblique section angle. Upon receiving the oblique cross-sectional image notification, the imaging control unit 2405 adds imaging technique information including the image information of the acquired oblique cross-sectional image to the oblique cross-sectional image notification, and transmits the oblique cross-sectional image notification to the display control unit 2409 via the test control unit 2406. On the other hand, if three-dimensional voxel data is not reconstructed in step S3505, the process transitions to step S3506. Next, in step S3506, three-dimensional texture limitation determination processing is executed. The imaging control unit 2405 transmits a three-dimensional texture limitation determination request notification to the 3D determination unit 2401. Upon receiving the three-dimensional texture limitation determination request notification, the 3D determination unit 2401 executes three-dimensional texture limitation determination, and transmits a three-dimensional texture limitation determination result notification to the imaging control unit 2405. Upon receiving the three-dimensional texture limitation determination result notification, the imaging control unit 2405 confirms the three-dimensional texture limitation determination result. If the three-dimensional texture limitation determination result is less than the limitation, three-dimensional voxel data is reconstructed in step S3507. The imaging control unit 2405 transmits a reconstruction request notification to the image processing unit 2110. Upon receiving the reconstruction request notification, the image processing unit 2110 executes reconstruction processing using the default reconstruction parameters of the imaging technique information, the position information, and the X-ray image data. When the reconstruction processing is completed, the image processing unit 2110 transmits a reconstruction completion notification to the imaging control unit 2405. Upon receiving the reconstruction completion notification, the imaging control unit 2405 transitions to step S3509. Next, in step S3509, the imaging control unit 2405 transmits an oblique cross-sectional image acquisition notification to the image processing unit 2110. Upon receiving the oblique cross-sectional image acquisition notification, the image processing unit 2110 acquires an oblique cross-sectional image having a designated oblique section central position and oblique section angle from the three-dimensional voxel data, and transmits it to the imaging control unit 2405 as an oblique cross-sectional image notification. Upon receiving the oblique cross-sectional image notification, the imaging control unit 2405 adds the image information of the acquired oblique cross-sectional image to the oblique cross-sectional image notification, and transmits the oblique cross-sectional image notification to the display control unit 2409 via the test control unit 2406. On the other hand, if two-dimensional oblique image reconstruction is selected in step S3504, or if the three-dimensional texture limitation determination result exceeds the limitation in step S3506, the process transitions to step S3508. In step S3508, reconstruction processing of a two-dimensional oblique cross-sectional image is executed. The imaging control unit 2405 transmits a two-dimensional oblique cross-sectional image reconstruction request notification to the image processing unit 2110. Upon receiving the two-dimensional oblique cross-sectional image reconstruction request notification, the image processing unit 2110 executes reconstruction processing using the default reconstruction parameters of the imaging technique information, the position information, and the X-ray image data, and generates a two-dimensional oblique cross-sectional image. When the reconstruction processing is completed, the image processing unit 2110 transmits a two-dimensional oblique image reconstruction completion notification to the imaging control unit 2405 in step S3510. Upon receiving the two-dimensional oblique image reconstruction completion notification, the imaging control unit 2405 adds imaging technique information including the image information of the acquired two-dimensional oblique cross-sectional image to the two-dimensional oblique image reconstruction completion notification, and transmits the two-dimensional oblique image reconstruction completion notification to the display control unit 2409 via the test control unit 2406. Next, in step S3511, the oblique cross-sectional image is displayed. Upon receiving the reconstruction completion notification or two-dimensional oblique image reconstruction completion notification, the display control unit 2409 preview-displays the tomosynthesis image in the tomographic image region 3302 displayed on the display unit 2109, and updates the displayed annotation. Next, in step S3512, display of the guideline image in the oblique angle editing portion is updated. After executing the preview display of the oblique cross-sectional image, the display unit 2109 corrects the display angle of the guideline image in the oblique angle editing portion to the same display angle as the preview-displayed oblique cross-sectional image, updates the display, and ends the processing.

An example of an imaging technique setting screen 3601 will be described next with reference to FIG. 36. The imaging technique setting screen 3601 is a screen that sets conditions concerning imaging and process contents in advance at once as imaging technique information. The imaging technique setting screen 3601 is formed from a protocol name region 3602, a series description region 3603, a comment region 3604, a laterality marker setting 3605, a DICOM attribute setting region 3606, an oblique limitation setting region 3607, a cancel button 3608, and a determination button 3609. However, other settings may be included if the setting items concern an imaging technique. The protocol name region 3602 is a region to set the name of an imaging technique. The series description region 3603 is a region to set a series description for each imaging technique. The comment region 3604 is a region to set an arbitrary character string as a comment to an imaging technique. The laterality marker setting 3605 is a region to individually set the arrangement of a laterality marker to an imaging technique. The laterality marker setting 3605 includes at least the setting of a position to arrange each marker by default and an ON/OFF setting to set whether to automatically arrange a laterality marker immediately after imaging. Other settings concerning the laterality markers may be included. The DICOM attribute setting region 3606 is a region to set a DICOM attribute decided by the layer of an imaging technique. The DICOM attribute setting region 3606 includes at least the settings of a test part, a subject method, a field position, and a laterality. Other settings of the DICOM attribute included in the layer of an imaging technique may be included. The oblique limitation setting region 3607 is a region to set a method of limiting oblique section display in a case in which imaging is performed under imaging conditions that exceed the three-dimensional texture limitation for each imaging technique. The oblique limitation setting region 3607 includes at least an oblique section display limitation application enable/disable setting and a display limiting method setting. If the oblique section display limitation application enable/disable setting is ON, display of an oblique cross-sectional image is limited by a selected display limiting method in a case in which the image size of projected images exceeds the three-dimensional texture limitation. If the oblique section display limitation application enable/disable setting is OFF, display of an oblique cross-sectional image is impossible in a case in which the image size of projected images exceeds the three-dimensional texture limitation. The display limiting method is selectable from at least "thin projected images", "cut out projected images", "reduce the pixel size of three-dimensional voxel data", "reduce the three-dimensional voxel data size", "prohibit oblique section display", and "reconstruct an oblique section by two-dimensional data". When "reconstruct an oblique section by two-dimensional data" is selected, default placement of an oblique angle is possible. As described above, when the oblique section display limitation application enable/disable setting and the display limiting method setting are settable for each imaging technique, the oblique section display limitation can be switched in accordance with a requirement such as an image accuracy, imaging procedure, or purpose of diagnosis for an imaging technique. The cancel button 3608 is a button that specifies to discard the editing contents on the imaging technique setting screen 3601. The determination button 3609 is a button that specifies to determine the editing contents on the imaging technique setting screen 3601. The imaging technique setting screen 3601 having the above-described arrangement is displayed.

Figure 37:
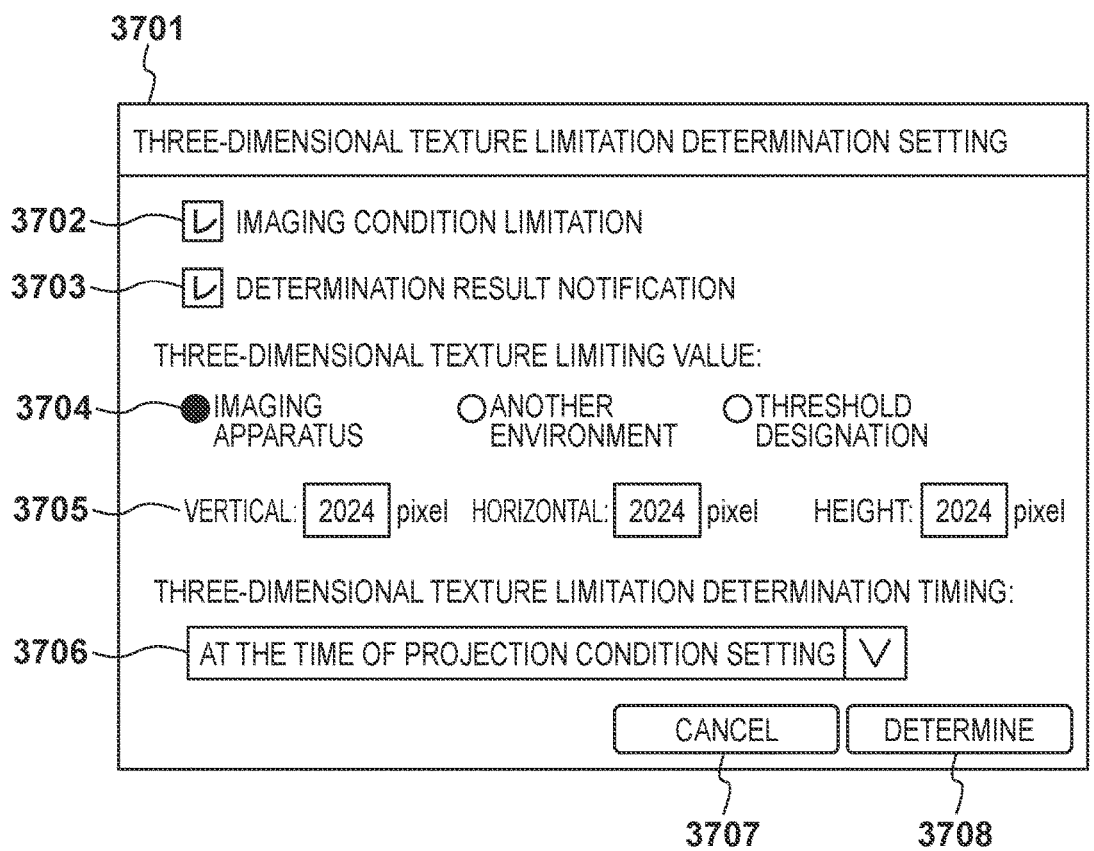
FIG. 37 is a view showing a three-dimensional texture limitation determination setting screen according to the embodiment of the present invention.

An example of a three-dimensional texture limitation determination setting 3701 will be described next with reference to FIG. 37. The three-dimensional texture limitation determination setting 3701 is a screen that sets, in advance, execution of determining whether a size exceeds the three-dimensional texture limitation when tomosynthesis image capturing is performed by the X-ray imaging system and a control operation based on a determination result. The 3D limitation setting screen 3701 is formed from a condition limitation setting region 3702, a notification setting region 3703, an acquisition destination setting region 3704, a limiting value input region 3705, a determination timing setting region 3706, a cancel button 3707, and a determination button 3708. The condition limitation setting region 3702 is a region to select whether to limit imaging conditions set at the time of imaging in a case in which it is determined as the result of three-dimensional texture limitation determination that the image size exceeds the threshold. If the imaging condition limitation enable/disable setting is ON, the settings of imaging conditions are discarded at the timing of determining as the result of three-dimensional texture limitation determination that the image size exceeds the threshold. When the settings are discarded, default imaging conditions or conditions of maximum values out of conditions that make the size fall within the three-dimensional texture limitation are automatically set. If the imaging condition limitation enable/disable setting is OFF, the imaging conditions are not limited in the X-ray imaging system irrespective of the determination result. The notification setting region 3703 is a region to select whether to perform notification if it is determined as the result of three-dimensional texture limitation determination that the image size exceeds the threshold. If the determination result notification is ON, a warning dialogue is displayed at the timing of determining as the result of three-dimensional texture limitation determination that the image size exceeds the threshold. If the determination result notification is OFF, the warning dialogue is not displayed even if it is determined as the result of three-dimensional texture limitation determination that the image size exceeds the threshold. The acquisition destination setting region 3704 is a region to select a destination to acquire the threshold to apply the three-dimensional texture limitation. The destination is selectable from at least "imaging apparatus", "another environment", and "threshold designation". When "imaging apparatus" is selected, the three-dimensional texture limiting value of the GPU included in the imaging apparatus is acquired. When "another environment" is selected, the three-dimensional texture limiting value of a GPU in another environment (for example, a workstation dedicated to reconstruction processing) connected to the imaging apparatus is acquired. When "threshold designation" is selected, vertical, horizontal, and height values designated in the limiting value input region 3705 are acquired as thresholds. The limiting value input region 3705 is a region to display the acquired three-dimensional texture limiting values and edit the thresholds designated as the limiting values. When "threshold designation" is selected in the acquisition destination setting region 3704, the limiting value input region 3705 can be edited. If another setting is selected, the limiting value input region 3705 displays the automatically acquired thresholds, and cannot be edited. The determination timing setting region 3706 is a region to select the timing at which determination processing of determining whether the image size exceeds the three-dimensional texture limitation is executed. The timing is selectable from at least "imaging condition setting time", "end of imaging", and "oblique section display execution time". The cancel button 3707 is a button that specifies to discard the editing contents on the 3D limitation setting screen 3701. The determination button 3708 is a button that specifies to determine the editing contents on the 3D limitation setting screen 3701. The three-dimensional texture limitation determination setting 3701 having the above-described arrangement is displayed.

As described above, according to one embodiment of the present invention, the imaging control apparatus 2107 that controls tomosynthesis image capturing mainly by the X-ray detector 2106 receives projected images from the X-ray detector 2106 and reconstructs them into three-dimensional volume data or two-dimensional tomographic images. This makes it possible to display a tomosynthesis image quickly after tomosynthesis image capturing and take advantage of the tomosynthesis image capturing as a simple computed tomography apparatus. When the first reconstruction method of reconstructing three-dimensional volume data is selected, an oblique cross-sectional image can be generated in quick response to a user operation. When the second reconstruction method of reconstructing two-dimensional tomographic images is selected, two-dimensional tomographic images of a high resolution can quickly be reconstructed. Both methods can perform quick reconstruction, generation, and display processing by taking advantage of simple tomosynthesis image capturing.

In the above-described embodiment, the imaging control apparatus 2107 is a single apparatus. However, the present invention is not limited to this, and a control system including a plurality of apparatuses may distributively execute processing. For example, the image processing unit 2110 may be a server apparatus that communicates an apparatus having the function of the control unit 2111 via a network. In this case, a plurality of control units 2111 can share the function of the image processing unit 2110, and efficiency increases. Such a server apparatus need not always exist in the same country as the control unit 2111. Alternatively, some of the functions of the control unit 2111 may be executed by an external apparatus.

In the above-described embodiment, an example in which the X-ray imaging system 2101 formed from a plurality of apparatuses or units executes tomosynthesis has been described. However, an integrated X-ray imaging apparatus may be used. For example, the communication circuit 2112 is connected to an intra-hospital network on which the PACS 2115 and the like exist, and the X-ray detector 2106 is directly connected to the control unit 2111. For example, the X-ray control unit 2104 and the moving mechanism control unit 21051 may be the same unit as the control unit 2111. The X-ray detector 2106 and the imaging control apparatus 2107 may be called an X-ray imaging apparatus together. Alternatively, they may be called an X-ray imaging apparatus, including the X-ray generation apparatus 2102 or imaging table 2105.

In the above-described embodiments, the image processing unit 2110 of the imaging control apparatus 2107 executes processing according to the present invention. However, the present invention is not limited to this, and an image processing apparatus such as a PACS or workstation connected to an X-ray imaging system for performing tomosynthesis image capturing may execute the processing. In this case, the image processing apparatus has the functions of, for example, the image processing unit 2110, the control unit 2111, and the communication circuit 2112 according to the embodiment of the present invention, and performs reconstruction processing or oblique cross-sectional image generation processing. When reconstruction processing or oblique cross-sectional image generation processing is performed in the server apparatus in a PACS, the functions of the display control unit 2409 are provided on the side of the viewer apparatus of the PACS. For example, in this case, the present invention is implemented not as a single image processing apparatus but as an image processing system.

Variations of the embodiments of the present invention have been described above. However, the present invention is not limited to the above-described examples.

In addition, the present invention is also implemented by executing the following processing. That is, software (program) that implements the functions of the above-described embodiments is supplied to a system or apparatus via a network or various kinds of storage media, and the computer (or CPU or MPU) of the system or apparatus reads out and executes the program.

The present invention is not limited to the above embodiments, and various changes and modifications can be made within the spirit and scope of the present invention. Therefore, to apprise the public of the scope of the present invention, the following claims are made.

The invention claimed is:

1. An information processing apparatus comprising:
   a storage unit adapted to store tomographic images;
   a determination unit adapted to determine whether a dimension of a plurality of tomographic images acquired from a single object is not more than a predetermined size;
   a storage control unit adapted to, upon determining that the dimension of the plurality of tomographic images is not more than the predetermined size, store the plurality of tomographic images as three-dimensional voxel data in the storage unit, and upon determining that the dimension of the plurality of tomographic images is more than the predetermined size, store the plurality of tomographic images as a plurality of two-dimensional data in the storage unit;
   a decision unit adapted to decide a cross-sectional image of a cross-sectional surface specified on the three-dimensional voxel data in the case where the storage control unit stores the plurality of tomographic images as three-dimensional voxel data in the storage unit, and to decide a tomographic image in accordance with one of the plurality of two-dimensional data as a cross-sectional image in the case where the storage control unit stores the plurality of tomographic images as a plurality of two-dimensional data in the storage unit; and
   a display control unit adapted to cause a display unit to display the decided cross-sectional image,
   wherein if the plurality of tomographic images are stored as the three-dimensional voxel data in the storage unit, the decision unit decides the cross-sectional image, in an arbitrary direction that is not a plane direction of the plurality of tomographic images, by interpolating pixel values of the three-dimensional voxel data.

2. The information processing apparatus according to claim 1, wherein if the plurality of tomographic images are stored as the two-dimensional data in the storage unit, the decision unit decides the cross-sectional image in accordance with index information of the two-dimensional data.

3. The information processing apparatus according to claim 1, wherein upon determining that the dimension is more than the predetermined size, the storage control unit stores a partial region of the plurality of tomographic images as the three-dimensional voxel data in the storage unit.

4. The information processing apparatus according to claim 3, wherein the storage control unit decides the partial region based on a specification from a user.

5. The information processing apparatus according to claim 1, wherein the decision unit decides a plurality of cross-sectional images as the cross-sectional image of the display target, and the display control unit causes the display unit to display a plurality of cross-sectional images decided as the decided cross-sectional image.

6. The information processing apparatus according to claim 5, wherein if the plurality of tomographic images are stored as the three-dimensional voxel data in the storage unit, the decision unit decides a plurality of cross-sectional images as the cross-sectional image of the display target.

7. The information processing apparatus according to claim 1, wherein the plurality of tomographic images are images collected by tomosynthesis image capturing.

8. The information processing apparatus according to claim 1, wherein if both a height and a width of the plurality of tomographic images are not more than a predetermined height and width, the determination unit determines that the dimension is not more than the predetermined size.

9. The information processing apparatus according to claim 1, wherein each of the plurality of tomographic images has associated therewith a plurality of measurements, each of the plurality of measurements being measured in a number of pixels, and the determination unit determines that the dimension is not more than the predetermined size in accordance with a measurement of the plurality of measurements.

10. The information processing apparatus according to claim 1, wherein each of the plurality of tomographic images has associated therewith a plurality of measurements, each of the plurality of measurements being measured in a number of pixels, and the determination unit determines that the dimension is not more than the predetermined size in accordance with the plurality of measurements.

11. The information processing apparatus according to claim 10, wherein the plurality of measurements include a height measurement and a width measurement of a tomographic image of the plurality of tomographic images.

12. An information processing method executed by an information processing apparatus comprising a storage unit adapted to store tomographic images, the information processing method comprising:
    determining whether a dimension of a plurality of tomographic images acquired from a single object is not more than a predetermined size;
    upon determining that the dimension of the plurality of tomographic images is not more than the predetermined size, storing the plurality of tomographic images as three-dimensional voxel data in the storage unit, and, upon determining that the dimension of the plurality of tomographic images is more than the predetermined size, storing the plurality of tomographic images as a plurality of two-dimensional data in the storage unit;
    deciding a cross-sectional image of a cross-sectional surface specified on the three-dimensional voxel data in the case where the plurality of tomographic images are stored as three-dimensional voxel data in the storage unit, and deciding a tomographic image in accordance with one of the plurality of two-dimensional data as a cross-sectional image in the case where the plurality of tomographic images are stored as a plurality of two-dimensional data in the storage unit; and
    causing a display unit to display the decided cross-sectional image, wherein if the plurality of tomographic images are stored as the three-dimensional voxel data in the storage unit, the deciding decides the cross-sectional image, in an arbitrary direction that is not a plane direction of the plurality of tomographic images, by interpolating pixel values of the three-dimensional voxel data.

13. The information processing method according to claim 12, wherein if the plurality of tomographic images are stored as the two-dimensional data in the storage unit, the cross-sectional image is decided, in the deciding, in accordance with index information of the two-dimensional data.

14. The information processing method according to claim 12, wherein upon determining that the dimension is more than the predetermined size, a partial region of the plurality of tomographic images is stored, in the storing, as the three-dimensional voxel data in the storage unit.

15. The information processing method according to claim 14, wherein the partial region is decided based on a specification from a user.

16. The information processing method according to claim 12, wherein a plurality of cross-sectional images are decided, in the deciding, as the cross-sectional image of the display target, and, in the causing the display unit to display, the display unit is caused to display a plurality of cross-sectional images decided as the decided cross-sectional image.

17. The information processing method according to claim 16, wherein if the plurality of tomographic images are stored as the three-dimensional voxel data in the storage unit, a plurality of cross-sectional images are decided, in the deciding, as the cross-sectional image of the display target.

18. The information processing method according to claim 12, wherein the plurality of tomographic images are images collected by tomosynthesis image capturing.

19. The information processing method according to claim 12, wherein if both a height and a width of the plurality of tomographic images are not more than a predetermined height and width, it is determined, in the determining, that the dimension is not more than the predetermined size.

20. The information processing method according to claim 12, wherein each of the plurality of tomographic images has associated therewith a plurality of measurements, each of the plurality of measurements being measured in a number of pixels, and the determining determines that the dimension is not more than the predetermined size in accordance with the plurality of measurements.

* * * * *